US011530255B2

(12) United States Patent
Kyratsous et al.

(10) Patent No.: US 11,530,255 B2
(45) **Date of Patent: *Dec. 20, 2022**

(54) HUMAN ANTIBODIES TO EBOLA VIRUS GLYCOPROTEIN

(71) Applicant: REGENERON PHARMACEUTICALS, INC., Tarrytown, NY (US)

(72) Inventors: Christos Kyratsous, Irvington, NY (US); William Olson, Yorktown Heights, NY (US); Peter Mason, Somerville, MA (US); Neil Stahl, Carmel, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 10 days.

This patent is subject to a terminal disclaimer.

(21) Appl. No.: 17/039,557

(22) Filed: Sep. 30, 2020

(65) Prior Publication Data

US 2021/0024617 A1 Jan. 28, 2021

Related U.S. Application Data

(60) Continuation of application No. 16/663,261, filed on Oct. 24, 2019, now Pat. No. 10,829,544, which is a continuation of application No. 16/108,096, filed on Aug. 22, 2018, now Pat. No. 10,501,526, which is a continuation of application No. 15/688,474, filed on Aug. 28, 2017, now Pat. No. 10,081,670, which is a division of application No. 15/005,334, filed on Jan. 25, 2016, now Pat. No. 9,771,414.

(60) Provisional application No. 62/245,703, filed on Oct. 23, 2015, provisional application No. 62/161,356, filed on May 14, 2015, provisional application No. 62/107,581, filed on Jan. 26, 2015.

(51) Int. Cl.
| | |
|---|---|
| *C07K 16/10* | (2006.01) |
| *A61K 39/395* | (2006.01) |
| *A61K 39/00* | (2006.01) |

(52) U.S. Cl.
CPC .......... *C07K 16/10* (2013.01); *A61K 39/3955* (2013.01); *A61K 2039/507* (2013.01); *C07K 2317/21* (2013.01); *C07K 2317/33* (2013.01); *C07K 2317/565* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,596,541 | B2 | 7/2003 | Murphy et al. |
| 6,630,144 | B1 | 10/2003 | Hart et al. |
| 6,875,433 | B2 | 4/2005 | Hart et al. |
| 7,335,356 | B2 | 2/2008 | Hart et al. |
| 7,582,298 | B2 | 9/2009 | Stevens et al. |
| 8,246,995 | B2 | 8/2012 | Dai et al. |
| 8,257,740 | B1 | 9/2012 | Sung et al. |
| 8,409,838 | B2 | 4/2013 | Chen et al. |
| 8,513,391 | B2 | 8/2013 | Jones et al. |
| 8,586,713 | B2 | 11/2013 | Davis et al. |
| 9,097,713 | B2 | 8/2015 | Dye et al. |
| 9,145,454 | B2 | 9/2015 | Jones et al. |
| 9,249,214 | B2 | 2/2016 | Jones et al. |
| 9,346,875 | B2 | 5/2016 | Lai et al. |
| 10,081,670 | B2 | 9/2018 | Kyratsous et al. |
| 10,501,526 | B2 | 12/2019 | Kyratsous et al. |
| 2004/0101920 | A1 | 5/2004 | Radziejewski et al. |
| 2010/0331527 | A1 | 12/2010 | Davis et al. |
| 2016/0151492 | A1 | 6/2016 | Jones et al. |
| 2016/0215040 | A1 | 7/2016 | Kyratsous et al. |
| 2020/0148751 | A1 | 5/2020 | Kyratsous et al. |

FOREIGN PATENT DOCUMENTS

| | | | |
|---|---|---|---|
| WO | 2004/018649 | A2 | 3/2004 |
| WO | 2005/103081 | A2 | 11/2005 |
| WO | 2009/094755 | A1 | 8/2009 |
| WO | 2010/048615 | | 4/2010 |
| WO | 2011/071574 | | 6/2011 |
| WO | 2015/127136 | | 8/2015 |

(Continued)

OTHER PUBLICATIONS

Alazard-Dany et al. (2006) "Ebola virus glycoprotein GP is not cytotoxic when expressed constitutively at a moderate level," J. Gen. Virol., 87:1247-1257.
Al-Lazikani et al. (1997) "Standard Conformations for the Canonical Structures of Immunoglobulins," J. Mol. Biol., 273:927-948.

Altschul et al. (1990) "Basic Local Alignment Search Tool", J. Mol. Biol.,215: 403-410.

Arruebo, et al. 2009 "Antibody-conjugated nanoparticles for biomedical applications," in J. Nanomat. vol. 2009, Article ID 439389, 24 pages.

(Continued)

*Primary Examiner* — Benjamin P Blumel

(74) *Attorney, Agent, or Firm* — FisherBroyles, LLP; Cara L. Crowley-Weber; Gabriele Amodeo

(57) ABSTRACT

The present invention provides monoclonal antibodies, or antigen-binding fragments thereof, that bind to Ebola virus glycoproteins, pharmaceutical compositions comprising the antibodies and methods of use. The antibodies of the invention are useful for inhibiting or neutralizing Ebola virus activity, thus providing a means of treating or preventing Ebola virus infection in humans. In some embodiments, the invention provides for use of one or more antibodies that bind to the Ebola virus for preventing viral attachment and/or entry into host cells. The antibodies of the invention may be used prophylactically or therapeutically and may be used alone or in combination with one or more other anti-viral agents or vaccines.

18 Claims, 2 Drawing Sheets

Specification includes a Sequence Listing.

(56) References Cited

FOREIGN PATENT DOCUMENTS

| WO | 2015/200522 | 12/2015 |
|---|---|---|
| WO | 2016/028503 | 2/2016 |
| WO | 2016/054598 | 4/2016 |
| WO | 2016/061504 | 4/2016 |

OTHER PUBLICATIONS

Audet et. al. (2014) "Molecular Characterization of the Monoclonal Antibodies Composing ZMAb: A Protective Cocktail Against Ebola Virus," Scientific Reports 4:6881.
Chen et.al. (2014) "Synthetic Antibodies with a Human Framework That Protect Mice from Lethal Sudan Ebolavirus Challenge," ACS Chem Biol. 9(10):2263-2273.
Cote et al. (2011) "Small molecule inhibitors reveal Niemann-Pick C1 is essential for ebolavirus infection," Nature, 477(7364):344-348.
Dondelinger, et al. (2018) "Understanding the Significance and Implications of Antibody Numbering and Antigen-Binding Surface/Residue Definition", Frontiers in Immunology, 9(Article 2278):1-15.
Dolnik et al., (2004) "Ectodomain shedding of the glycoprotein GP of Ebola virus," EMBO J 23:2175-2184.
Dye et al. (2012) "Postexposure antibody prophylaxis protects nonhuman primates from filovirus disease," Proc Natl Acad Sci USA 109(13):5034-5039.
Ehring (1999) "Hydrogen Exchange/Electrospray Ionization Mass Spectrometry Studies of Structural Features of Proteins and Protein/Protein Interactions," Analytical Biochemistry 267:252-259.
Engen and Smith (2001) "The Basics of Ion Chromatography," Anal. Chem. 73: 256A-265A.
Escuerdo-Perez et al. (2014) "Shed GP of Ebola Virus Triggers Immune Activation and Increased Vascular Permeability," PLOS Pathogens, vol. 10, Issue 11:1-17.
Falzarano et al. (2006) "Structure-function analysis of the soluble glycoprotein, sGP, of Ebola virus," Chembiochem, 7:1605-1611.
Feldman, et al. (1992) "Marburg virus, a filovirus: messenger RNAs, gene order, and regulatory elements of the replication cycle," Virus Res. 24, 1-19.
Feldman, et al. (2007) "Effective Post-Exposure Treatment of Ebola Infection," PLos Pathog 3(1):e2.
Geisbert et al. (2006) "Postexposure Protection of Guinea Pigs against a Lethal Ebola Virus Challenge Is Conferred by RNA Interference," J. Infect Dis. 3(12):1650-1657.
Geisbert et al. (2010) "Postexposure protection of non-human primates against a lethal Ebola virus challenge with RNA interference: a proof-of-concept study," Lancet 375(9729):1896-1905.
GenBank AHX24649.1.
GenBank KJ660346.2, Zaire 2014.
Gonnet et al. (1992) "Exhaustive Matching of the Entire Protein Sequence Database," Science 256: 1443 45.
Good et al., (1991) "Historic Aspects of Intravenous Immunoglobulin Therapy," Cancer 68: 1415-1421.
Johansen et al. (2013) "FDA-approved selective estrogen receptor modulators inhibit Ebola virus infection," Sci Transl Med 5(190):190ra179.
Kazane et al. (2013) "Self-Assembled Antibody Multimers through Peptide Nucleic Acid Conjugation,"J. Am. Chem. Soc. 135(1): 340-346.
Klein et al. (2012) "Progress in overcoming the chian association issue in bispecific heterodimeric IgG antibodies," mAbs 4:6, 1-11.
Koellhoffer et.al. (2012) "Two Synthetic Antibodies that Recognize and Neutralize Distinct Proteolytic Forms of the Ebola Virus Envelope Glycoprotein," Chembiochem Nov. 26; 13(17):2549-57.
Kufer et al. (2004) "A revival of bispecific antibodies," Trends Biotechnol. 22:238-244.
Langer (1990) "New Methods of Drug Delivery," Science 249:1527-1533.
Lonberg, et al. (2008) "Fully human antibodies from transgenic mouse and phage display platforms," Current Dpinion in Immunology, Elsevier 20:450-459.
Marasco et al (2007) "The growth and potential of human antiviral monoclonal antibody therapeutics," Nature Biotechnology 25: 1421-1434.
Martin et al. (1989) "Modeling antibody hypervariable loops: A combined algorithm," Proc. Natl. Acad. Sci. USA 86:9268-9272 (1989).
Martinez, et al. (2011) "Impact of Ebola Mucin-Like Domain on Antiglycoprotein Antibody Responses Induced by Ebola Virus-Like Particles," Journal of Infectious Diseases, 204(3):S825-S832.
Maruyama et al. (1999) "Ebola Virus Can Be Effectively Neutralized by Antibody Produced in Natural Human Infection," J. Virol 73, 6024-6030.
Mikhailov (1994), "[The evaluation in hamadryas baboons of the possibility for the specific prevention of Ebola fever]" (in Russian) Vopr. Virusol 39(2): 82-84.
Morris (1996) "Epitope Mapping of Protein Antigens by Competition ELISA," In:"The Protein Protocols Handbook," Humana Press, Totowa, NJ pp. 595-600.
Murin, et al. (2014) "Structures of protective antibodies reveal sites of vulnerability on Ebola virus," Proc Natl Acad Sci USA, 111(48):17182-17187.
Murphy (2009) "VelocImmune: Immunoglobulin Variable Region Humanized Mice," Recombinant Antibodies for Immunotherapy, Cambridge University Press, GB pp. 100-107.
Murphy (2014) "Mice with megabase humanization of their immunoglobulin genes generate antibodies as efficiently as normal mice", PNAS, 111(14):5153-5158.
Padlan et al. (1995) "Identification of specificity-determining residues in antibodies," FASEB J. 9:133-139.
Pascal et al. (2018) "Development of Clinical-Stage Human Monoclonal Antibodies That Treat Advanced Ebola Virus Disease in Nonhuman Primates", J. Infectious Disease, 218(S5):S612-S626.
Pearson (1994) "Using the FASTA Program to Search Protein and DNA Sequence Databses," Methods Mol. Biol. 24: 307-331.
Peters and Leduc (1999) "An Introduction to Ebola: The Virus and the Disease," J. Infect. Dis. 179 Suppl 1.
Powell et al. (1998) "Compendium of excipients for parenteral formulations," PDA J Pharm Sci Technol 52:238-311.
Qiu et al. (2014) "Antibody therapy for Ebola, Is the tide turning around?"Hum. Vaccin. Immunother. 10(4):964-967.
Qiu et al. (2014) "Reversion of advanced Ebola virus disease in nonhuman primates with Zmapp,™" Nature 514 (7520):47-53.
Qiu, et al. (2011) "Charaterization of Zaire ebolavirus glycoprotein-specific monoclonal antibodies," Clinical Immunology 141(2):218-227.
Qiu, et al. (2012) "Ebola GP-Specific Monoclonal Antibodies Protect Mice and Guinea Pigs from Lethal Ebola Virus nfection," PLOS Neglected Tropical Diseases, 6(3):e1575.
Qui, et al. (2012) "Successful Treatment of Ebola Virus-Infected Cynomolgus Macaques with Monoclonal Antibodies," Science Translation Medicine 4(138):138ra81.
Reddy et al. (2000) "Elimination of Fc Receptor-Dependent Effector Functions of a Modified IgG4 Monoclonal Antibody to Human CD4," J. Immunol. 164:1925-1933.
Reineke (2004) "Antibody Epitope Mapping Using Arrays of Synthetic Peptides," Methods Mol. Biol. 248: 443-63.
Baize, et al. (2014) "Emergence of Zaire Ebola Virus Disease in Guinea", The New England Journal of Medicine, 371 (15):1418-1425.
Gershoni, et al. (2007) "Epitope Mapping The First Step in Developing Epitope-Based Vaccines", Biodrugs, Adis International LTD, NZ, 21(3): 145-156.
Sanchez et al. (1996) "The virion glycoproteins of Ebola viruses are encoded in two reading frames and are expressed through transcriptional editing," Proc Natl Acad Sci USA, 93:3602-3607.
Sanchez et al. (1998) "Biochemical Analysis of the Secreted and Virion Glycoproteins of Ebola Virus," J. Virol. 72:6442-6447.
Sanchez et al. (1999) "Detection and molecular characterization of Ebola viruses causing disease in human and nonhuman primates," J. Infect. Dis. 179 (suppl. 1, S164).

(56) References Cited

OTHER PUBLICATIONS

Saphire (2013) "An update on the use of antibodies against the filoviruses," Immunotherapy, 5(11):1221-1233.

Sela-Culang, et al. (2013) "The structural basis of antibody-antigen recognition", Frontiers in Immunology, 4(Article 302):1-13.

Sivapalasingam et al. (2018) "Safety, Pharmacokinetics, and Immunogenicity fo a Co-Formulated Cocktail of Three Human Monoclonal Antibodies Targeting Ebola Virus Glycoprotein in Healthy Adults: A Randomised, First-In-Human Phase 1 Study", Lancet Infect Dis, 18(8):884-893.

Sekine (2009) "The Current State an the Issue of Antibody Drugs", Science & Technology Trends, Quaterly Review No. 35, 14 pages.

Sekine (2010) "The Current State an the Issue of Antibody Drugs", Science & Technology Trends, Quaterly Review No. 35, 14 pages.

Shields et al. (2002) "Lack of Fucose on Human IgG1 N-Linked Oligosaccharide Improves Binding to Human Fc RIII and Antibody-dependent Cellular Toxicity," JBC 277:26733-26740.

Shingarova, et al. (2007) "Recombinant Full-Size Human Antiobdy to Ebola Virus," Russian Journal of Bioorganic Chemistry, 33(6):554-561.

Sobarzo, et al. (2013) "Profile and Persistence of the Virus-Specific Neutrazling Humoral Immune Response in Human Survivors of Sudan Ebolavirus (Gulu),"Journal of Infectious Diseases 208:299-309.

Tomer (2000) "Characterization of a discontinuous epitope of the human immunodeficiency virus (HIV) core protein p24 by epitope excision and differential chemical modification followed by mass spectrometric peptide mapping analysis," Prot. Sci. 9: 487-496.

Tutt et al. (1991) "Trispecific F(ab')3 Derivatives That use Cooperative Signaling via The TCR/CD3 Complex and CD2 to Activate and Redirect Resting Cytotoxic T Cells," J. Immunol. 147:60-69.

Vajdos, et al. (2002) "Comprehensive Functional Maps of the Antigen-binding Site of an Anti-ErbB2 Antibody Obtained with Shotgun Scanning Mutagenesis," J Mol Biol 320:415-428.

Volchkova et al. (1995) "GP mRNA of Ebola virus is edited by the Ebola virus polymerase and by T7 and vaccinia virus polymerases," Virology 214:421-430.

Volchkova et al. (1998) "The nonstructural small glycoprotein sGP of Ebola virus is secreted as an antiparallel-orientated homodimer," Virology 250:408-414.

Volchkova et al.(1998) "Processing of the Ebola virus glycoprotein by the proprotein convertase furin," Proc Natl Acad Sci USA 95:5762-5767.

Warren et al. (2014) "Protection against filovirus diseases by a novel broad-spectrum nucleoside analogue BCX4430," Nature, 508(7496):402-405.

Wong et al. (2014) "Post-exposure therapy of filovirus infections," Trends Microbiol. 22(8):456-463.

Wu et al. (1987) "Receptor-mediated in Vitro Gene Transformation by a Soluble DNA Carrier System," J. Biol. Chem. 262:4429-4432.

Xu et al. (1998) "Immunization for Ebola virus infection," Nature Med. 4:37.

International Search Report and Written Opinion for PCT/US2016/014720 dated Jun. 21, 2016.

International Preliminary Report on Patentability for PCT/US2016/14720, dated Dec. 19, 2016.

Altschul et al. (1997) "Gapped BLAST and PSI-BLAST: a new generation of protein database search programs," Nucleic Acids Res. 25:3389-3402.

SEQUENCE LISTING

<160> NUMBER OF SEQ ID NOS: 318

<210> SEQ ID NO 1
<211> LENGTH: 342
<212> TYPE: DNA
<213> ORGANISM: Artificial Sequence
<220> FEATURE:
<223> OTHER INFORMATION: synthetic

<400> SEQUENCE: 1

```
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatgatgg ggacacctac     180 tacaaccgt ccctcaagag tcgagtcacc atatccgtag acacgtccaa gaaccagttc     240
tccctgaggc tgagctctgt gaccgccgca gacacggcag tgtattactg tgcgagacag     300
tttgactact ggggccaggg aaccctggtc accgtctcct ca                         342
```

<210> SEQ ID NO 2
<211> LENGTH: 114
<212> TYPE: PRT
<213> ORGANISM: Artificial Sequence
<220> FEATURE:
<223> OTHER INFORMATION: synthetic

<400> SEQUENCE: 2

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45
```

```
Trp Ile Gly Ser Ile Tyr Tyr Asp Gly Asp Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Arg Leu Ser Ser Val Thr Ala Ala Asp Thr Ala Val Tyr Tyr
                85                  90                  95
Cys Ala Arg Gln Phe Asp Tyr Trp Gly Gln Gly Thr Leu Val Thr Val
            100                 105                 110
Ser Ser
```

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
ggtggctcca tcagcagtag tagttactac                                    30

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

```
Gly Gly Ser Ile Ser Ser Ser Ser Tyr Tyr
1               5                   10
```

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
atctattatg atggggacac c                                             21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

```
Ile Tyr Tyr Asp Gly Asp Thr
1               5
```

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
gcgagacagt ttgactac                                                 18

<210> SEQ ID NO 8

<211> LENGTH: 6
<212> TYPE: PRT
<213> ORGANISM: Artificial Sequence
<220> FEATURE:
<223> OTHER INFORMATION: synthetic

<400> SEQUENCE: 8

Ala Arg Gln Phe Asp Tyr
1               5

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gaaatagtga tgacgcagtc tccagccacc ctgtctgtgt ctccagggga aagagccacc    60
ctctcctgca gggccagtca gagtgttagt agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataaaaact ggccgatcac cttcggccaa   300
gggacacgac tggagattaa a                                             321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Asn Trp Pro Ile
                85                  90                  95

Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagtgtta gtagcaac                                                  18

<210> SEQ ID NO 12
<211> LENGTH: 6

```
<212> TYPE: PRT
<213> ORGANISM: Artificial Sequence
<220> FEATURE:
<223> OTHER INFORMATION: synthetic

<400> SEQUENCE: 12

Gln Ser Val Ser Ser Asn
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 ggtgcatcc                                                                 9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Gly Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
cagcagtata aaaactggcc gatcacc                                            27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr Lys Asn Trp Pro Ile Thr
1               5

<210> SEQ ID NO 17
<211> LENGTH: 354
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tgggggaggc ttggtacagc ctggggggtc cctgagactc        60
tcctgtgcag cctctggatt caccttcagt agctacgaca tgcactgggt ccgccaagct       120
acaggaaaag gtctggagtg ggtctcagct attggtactg ctggtgacac atactatcca       180
ggctccgtga aggccgatt caccatctcc agagaaaatg ccaaaaactc cttgtatctt       240
caaatgaaca gcctgagagc cggggacacg gctgtgtatt actgtgcaag aacatggttc       300
```
ggggagcttt actttgacta ctggggccag ggaaccctgg tcaccgtctc ctca        354

<210> SEQ ID NO 18
<211> LENGTH: 118
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Thr Trp Phe Gly Glu Leu Tyr Phe Asp Tyr Trp Gly Gln Gly Thr
            100                 105                 110

Leu Val Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtagcta cgac        24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Asp
1               5

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
attggtactg ctggtgacac a        21

<210> SEQ ID NO 22
<211> LENGTH: 7
<212> TYPE: PRT
<213> ORGANISM: Artificial Sequence
<220> FEATURE:
<223> OTHER INFORMATION: synthetic

<400> SEQUENCE: 22

Ile Gly Thr Ala Gly Asp Thr
1               5

<210> SEQ ID NO 23
<211> LENGTH: 36
<212> TYPE: DNA
<213> ORGANISM: Artificial Sequence
<220> FEATURE:
<223> OTHER INFORMATION: synthetic

<400> SEQUENCE: 23
gcaagaacat ggttcgggga gctttacttt gactac                              36

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Arg Thr Trp Phe Gly Glu Leu Tyr Phe Asp Tyr
1               5                   10

<210> SEQ ID NO 25
<211> LENGTH: 339
<212> TYPE: DNA
<213> ORGANISM: Artificial Sequence
<220> FEATURE:
<223> OTHER INFORMATION: synthetic

<400> SEQUENCE: 25
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagaatt cactctcacc   240
atcaccagcc tgcaggctga agatgtggca gtttattact gtcagcaata ttatagtagt   300
ccgctcactt tcggcggagg gaccaaggtg gagatcaaa                          339

<210> SEQ ID NO 26
<211> LENGTH: 113
<212> TYPE: PRT
<213> ORGANISM: Artificial Sequence
<220> FEATURE:
<223> OTHER INFORMATION: synthetic

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

-continued

```
Ile Thr Ser Leu Gln Ala Glu Asp Val Ala Val Tyr Tyr Cys Gln Gln
             85                  90                  95
Tyr Tyr Ser Ser Pro Leu Thr Phe Gly Gly Gly Thr Lys Val Glu Ile
        100                 105                 110
Lys

<210> SEQ ID NO 27
<211> LENGTH: 36
<212> TYPE: DNA
<213> ORGANISM: Artificial Sequence
<220> FEATURE:
<223> OTHER INFORMATION: synthetic

<400> SEQUENCE: 27
cagagtgttt tatacagctc caacaataag aactac                              36

<210> SEQ ID NO 28
<211> LENGTH: 12
<212> TYPE: PRT
<213> ORGANISM: Artificial Sequence
<220> FEATURE:
<223> OTHER INFORMATION: synthetic

<400> SEQUENCE: 28

Gln Ser Val Leu Tyr Ser Ser Asn Asn Lys Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 tgggcatct                                                             9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Trp Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
cagcaatatt atagtagtcc gctcact                                        27

<210> SEQ ID NO 32
<211> LENGTH: 9
<212> TYPE: PRT
<213> ORGANISM: Artificial Sequence
<220> FEATURE:
<223> OTHER INFORMATION: synthetic
```

<400> SEQUENCE: 32

Gln Gln Tyr Tyr Ser Ser Pro Leu Thr
1               5

<210> SEQ ID NO 33
<211> LENGTH: 375
<212> TYPE: DNA
<213> ORGANISM: Artificial Sequence
<220> FEATURE:
<223> OTHER INFORMATION: synthetic

<400> SEQUENCE: 33

```
gaggtgcagc tggtggagtc tgggggaggc ttggtacagc ctggggggtc cctgagactc      60
tcctgtgcag cctctggatt cacctttagc agctatgcca tgacctgggt ccgccaggct     120
ccagggaagg gcctggagtg gtctcaagt attagtggta gtggtactag cacatactac      180
gcagactccg tgaagggccg gttcaccatc tccagagaca attccaagaa cacactgtat     240
ctgcaaatga acagcctgcg agccgaggac acggccctat attactgttc gagagatata     300
tatacctgga acttcctctc actaattggc ggtatggacg tctggggcca agggaccacg     360
gtcaccgtct cctca                                                      375
```

<210> SEQ ID NO 34
<211> LENGTH: 125
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ser Arg Asp Ile Tyr Thr Trp Asn Phe Leu Ser Leu Ile Gly Gly Met
            100                 105                 110

Asp Val Trp Gly Gln Gly Thr Thr Val Thr Val Ser Ser
        115                 120                 125

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct ttagcagcta tgcc                                             24

<210> SEQ ID NO 36
<211> LENGTH: 8
<212> TYPE: PRT

<213> ORGANISM: Artificial Sequence
<220> FEATURE:
<223> OTHER INFORMATION: synthetic

<400> SEQUENCE: 36

Gly Phe Thr Phe Ser Ser Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagtggta gtggtactag caca                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Gly Ser Gly Thr Ser Thr
1               5

<210> SEQ ID NO 39
<211> LENGTH: 54
<212> TYPE: DNA
<213> ORGANISM: Artificial Sequence
<220> FEATURE:
<223> OTHER INFORMATION: synthetic

<400> SEQUENCE: 39
tcgagagata tatacctg gaacttcctc tcactaattg gcggtatgga cgtc            54

<210> SEQ ID NO 40
<211> LENGTH: 18
<212> TYPE: PRT
<213> ORGANISM: Artificial Sequence
<220> FEATURE:
<223> OTHER INFORMATION: synthetic

<400> SEQUENCE: 40

Ser Arg Asp Ile Tyr Thr Trp Asn Phe Leu Ser Leu Ile Gly Gly Met
1               5                   10                  15

Asp Val

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcaagtca gggcattaga attgatttag gctggtatca gcagaaacca   120
gggaaagccc ctaaccgcct gatctatgct gcatccagtt tgcaaggtgg gtcccatca    180 aggttcagcg gcagtggatc tgggacagaa ttcactctca caatcagcag cctgcagcct   240

```
gaagattttg caacttatta ctgtctacag caaaatagtt acccgtggac gttcggccaa    300
gggaccaagg tggaaatcaa a                                              321
```

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Ile Asp
            20                  25                  30

Leu Gly Trp Tyr Gln Lys Pro Gly Lys Ala Pro Asn Arg Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Gln Asn Ser Tyr Pro Trp
                85                  90                  95

Thr Phe Gly Gln Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43

```
cagggcatta gaattgat                                                  18
```

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Gly Ile Arg Ile Asp
1               5
```

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45

```
gctgcatcc                                                             9
```

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
ctacagcaaa atagttaccc gtggacg                                             27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Leu Gln Gln Asn Ser Tyr Pro Trp Thr
1               5

<210> SEQ ID NO 49
<211> LENGTH: 387
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggaggc ttggtacagc ctggggggtc cctgagactc         60
tcctgtgcag cctctggatt cacctttagc agctatgcca tgaactgggt ccgccaggct        120
ccagggaagg ggctggagtg ggtctcagtt attagtggta gtggtggttg gagaaactac        180
gcagactccg tgaagggccg gatcaccatc tccagagaca attccaagaa cacgctgtat        240
ctgcaaatga acaacctgag agccgaggac acggccgtat attattgtgc gaaagatcgg        300
ggtgcgactt ttggagtggt tattttggga cccccctatt acggtatgga cgtctggggc        360
caagggacca cggtcaccgt ctcctca                                            387

<210> SEQ ID NO 50
<211> LENGTH: 129
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Gly Trp Arg Asn Tyr Ala Asp Ser Val
    50                  55                  60

Lys Gly Arg Ile Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Asp Arg Gly Ala Thr Phe Gly Val Val Ile Leu Gly Pro Pro
            100                 105                 110

Tyr Tyr Gly Met Asp Val Trp Gly Gln Gly Thr Thr Val Thr Val Ser
        115                 120                 125

Ser

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct ttagcagcta tgcc                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Ser Ser Tyr Ala
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagtggta gtggtggttg gaga                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Gly Ser Gly Gly Trp Arg
1               5

<210> SEQ ID NO 55
<211> LENGTH: 66
<212> TYPE: DNA
<213> ORGANISM: Artificial Sequence
<220> FEATURE:
<223> OTHER INFORMATION: synthetic

<400> SEQUENCE: 55
gcgaaagatc ggggtgcgac ttttggagtg gttattttgg acccccccta ttacggtatg   60
gacgtc                                                              66

<210> SEQ ID NO 56
<211> LENGTH: 22

<212> TYPE: PRT
<213> ORGANISM: Artificial Sequence
<220> FEATURE:
<223> OTHER INFORMATION: synthetic

<400> SEQUENCE: 56

Ala Lys Asp Arg Gly Ala Thr Phe Gly Val Val Ile Leu Gly Pro Pro
1               5                   10                  15
Tyr Tyr Gly Met Asp Val
            20

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57

```
gacatccaga tgacccagtc tccatcctcc ctgtctgcat ctgtaagaga cagagtcacc    60
atcacttgcc gggcaagtca gagcattagc acttatttaa attggtatca gcagaaacca   120
gggaaagccc ctaagctcct gatctatgct gcatccagtt tgcaaagtgg ggtcccatca   180
aggttcagtg gcagtggatc tgggacaggt ttcactctca ccatcagcag tctgcaacct   240
gaagattttg caacttacta ctgtcaacag agttacagta tcccgtacac ttttggccag   300
gggaccaagc tggagatcaa a                                             321
```

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Arg
1               5                   10                  15
Asp Arg Val Thr Ile Thr Cys Arg Ala Ser Gln Ser Ile Ser Thr Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Gly Phe Thr Leu Thr Ile Ser Ser Leu Gln Pro
65                  70                  75                  80
Glu Asp Phe Ala Thr Tyr Tyr Cys Gln Gln Ser Tyr Ser Ile Pro Tyr
                85                  90                  95
Thr Phe Gly Gln Gly Thr Lys Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagagcatta gcacttat                                                  18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Ser Ile Ser Thr Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                                  9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacagagtt acagtatccc gtacact                                             27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ser Tyr Ser Ile Pro Tyr Thr
1               5

<210> SEQ ID NO 65
<211> LENGTH: 354
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtacagc ctggggggtc cctgagactc         60
tcctgtgcag cctctggatt cacctctagc agctatgcca tgaactgggt ccgccaggct        120
ccagggaagg ggctggagtg ggtctcaaca attagtggta tgggtggtag cacatactac        180
gcagactccg tgaagggccg gttcaccatc tccagagaca attccaagaa cacgctgtat        240
ctgcaaatga acagcctgag agccgaggac acggccgtat attactgtgc gaaaagggga    300
tatccccatt cttttgatat ctggggccaa gggacaatgg tcaccgtctc ttca          354

<210> SEQ ID NO 66
<211> LENGTH: 118
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Met Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Tyr Pro His Ser Phe Asp Ile Trp Gly Gln Gly Thr
            100                 105                 110

Met Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct ctagcagcta tgcc                                           24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Ser Ser Ser Tyr Ala
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attagtggta tgggtggtag caca                                           24

<210> SEQ ID NO 70
<211> LENGTH: 8

```
<212> TYPE: PRT
<213> ORGANISM: Artificial Sequence
<220> FEATURE:
<223> OTHER INFORMATION: synthetic

<400> SEQUENCE: 70

Ile Ser Gly Met Gly Gly Ser Thr
1               5

<210> SEQ ID NO 71
<211> LENGTH: 33
<212> TYPE: DNA
<213> ORGANISM: Artificial Sequence
<220> FEATURE:
<223> OTHER INFORMATION: synthetic

<400> SEQUENCE: 71
gcgaaaaggg gatatcccca ttcttttgat atc                                  33

<210> SEQ ID NO 72
<211> LENGTH: 11
<212> TYPE: PRT
<213> ORGANISM: Artificial Sequence
<220> FEATURE:
<223> OTHER INFORMATION: synthetic

<400> SEQUENCE: 72

Ala Lys Arg Gly Tyr Pro His Ser Phe Asp Ile
1               5                   10

<210> SEQ ID NO 73
<211> LENGTH: 318
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc      60
atcacttgcc gggcaagtca gagcattagc agcttttta attggtatca gcagaaacca     120
gggaaagccc ctaaactcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccctcacctt cggccaaggg     300
acacgactgg agattaaa                                                  318

<210> SEQ ID NO 74
<211> LENGTH: 106
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Thr
                85                  90                  95

Phe Gly Gln Gly Thr Arg Leu Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagagcatta gcagcttt                                                 18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Ser Ile Ser Ser Phe
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 24
<212> TYPE: DNA
<213> ORGANISM: Artificial Sequence
<220> FEATURE:
<223> OTHER INFORMATION: synthetic

<400> SEQUENCE: 79
caacagagtt acagtaccct cacc                                          24

<210> SEQ ID NO 80
<211> LENGTH: 8
<212> TYPE: PRT
<213> ORGANISM: Artificial Sequence
<220> FEATURE:
<223> OTHER INFORMATION: synthetic

<400> SEQUENCE: 80

Gln Gln Ser Tyr Ser Thr Leu Thr
1               5

<210> SEQ ID NO 81
<211> LENGTH: 354
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tgggggaggc ttggtacagc ctgggggtc cctgagactc      60 tcctgtgcag cctctgaatt cacctttagc agctatgcca tgagctgggt ccgccaggct    120
ccagggaagg gctggagtg gtctcagct attagtggta gtagtggtag cacatactac      180
gcagactccg tgaagggccg gttcaccatc tccagagaca attccaaaaa gacgctgtat    240
ctacaaatga acagcctgag agtcgaggac acggccgtat attactgtgc gaaaggggg    300 taccccatt cttttgatat ctggggccat gggacaatgg tcaccgtctc ttca          354

<210> SEQ ID NO 82
<211> LENGTH: 118
<212> TYPE: PRT
<213> ORGANISM: Artificial Sequence
<220> FEATURE:
<223> OTHER INFORMATION: synthetic

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ser Gly Ser Thr Tyr Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Val Glu Asp Thr Ala Val Tyr Tyr Cys
                85                  90                  95

Ala Lys Gly Gly Tyr Pro His Ser Phe Asp Ile Trp Gly His Gly Thr
            100                 105                 110

Met Val Thr Val Ser Ser
        115

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
gaattcacct ttagcagcta tgcc                                            24

<210> SEQ ID NO 84
<211> LENGTH: 8
<212> TYPE: PRT
<213> ORGANISM: Artificial Sequence
<220> FEATURE:

<223> OTHER INFORMATION: synthetic

<400> SEQUENCE: 84

Glu Phe Thr Phe Ser Ser Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
attagtggta gtagtggtag caca                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Gly Ser Ser Gly Ser Thr
1               5

<210> SEQ ID NO 87
<211> LENGTH: 33
<212> TYPE: DNA
<213> ORGANISM: Artificial Sequence
<220> FEATURE:
<223> OTHER INFORMATION: synthetic

<400> SEQUENCE: 87
gcgaaagggg ggtaccccca ttcttttgat atc                                33

<210> SEQ ID NO 88
<211> LENGTH: 11
<212> TYPE: PRT
<213> ORGANISM: Artificial Sequence
<220> FEATURE:
<223> OTHER INFORMATION: synthetic

<400> SEQUENCE: 88

Ala Lys Gly Gly Tyr Pro His Ser Phe Asp Ile
1               5                   10

<210> SEQ ID NO 89
<211> LENGTH: 318
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcctcc ctgtctgcat ctgtaggaga cagagtcacc    60
atcacttgcc gggcaagtca gagcattagc agcttttaa attggtatca gcagaaacca   120
gggaaagccc ctaaactcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagtt ccatcacctt cggccaaggg   300
acacgactgg agattaaa                                                318

<210> SEQ ID NO 90
<211> LENGTH: 106
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ile Thr
                85                  90                  95

Phe Gly Gln Gly Thr Arg Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagcatta gcagcttt                                              18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Ser Ile Ser Ser Phe
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctgcatcc                                                         9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Ala Ser

<210> SEQ ID NO 95
<211> LENGTH: 24
<212> TYPE: DNA
<213> ORGANISM: Artificial Sequence
<220> FEATURE:
<223> OTHER INFORMATION: synthetic

<400> SEQUENCE: 95
caacagagtt acagttccat cacc         24

<210> SEQ ID NO 96
<211> LENGTH: 8
<212> TYPE: PRT
<213> ORGANISM: Artificial Sequence
<220> FEATURE:
<223> OTHER INFORMATION: synthetic

<400> SEQUENCE: 96

Gln Gln Ser Tyr Ser Ser Ile Thr
1               5

<210> SEQ ID NO 97
<211> LENGTH: 375
<212> TYPE: DNA
<213> ORGANISM: Artificial Sequence
<220> FEATURE:
<223> OTHER INFORMATION: synthetic

<400> SEQUENCE: 97
caggtgcagc tggtggagtc tgggggaggc gtggtccagc ctggggaggtc cctgagactc     60 tcctgtgcag cgtctggatt caccttcagt agttatggca tccactgggt ccgccaggct    120
ccaggcaagt ggctggagtg ggtggcattt atatggtttg atggaagtaa taaatactat    180
gcagactccg tgaagggccg attcaccatc tccagagacg attccaagaa cacgctgtat    240
ctgcaaatga acagcctgag agccgaggac acggctgttt attactgtgc gagagatgga    300 gagattttg gagtgcttat ttcctctgat gcttttgata tctggggcca agggacaatg    360
gtcaccgtct cttca                                                    375

<210> SEQ ID NO 98
<211> LENGTH: 125
<212> TYPE: PRT
<213> ORGANISM: Artificial Sequence
<220> FEATURE:
<223> OTHER INFORMATION: synthetic

<400> SEQUENCE: 98

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Trp Leu Glu Trp Val
        35                  40                  45

Ala Phe Ile Trp Phe Asp Gly Ser Asn Lys Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Glu Ile Phe Gly Val Leu Ile Ser Ser Asp Ala Phe
            100                 105                 110

Asp Ile Trp Gly Gln Gly Thr Met Val Thr Val Ser Ser
        115                 120                 125

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggattcacct tcagtagtta tggc                                           24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Phe Thr Phe Ser Ser Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atatggtttg atggaagtaa taaa                                           24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Trp Phe Asp Gly Ser Asn Lys
1               5

<210> SEQ ID NO 103
<211> LENGTH: 54
<212> TYPE: DNA
<213> ORGANISM: Artificial Sequence
<220> FEATURE:
<223> OTHER INFORMATION: synthetic

<400> SEQUENCE: 103
gcgagagatg gagagatttt tggagtgctt atttcctctg atgcttttga tatc          54

<210> SEQ ID NO 104
<211> LENGTH: 18
<212> TYPE: PRT
<213> ORGANISM: Artificial Sequence
<220> FEATURE:
<223> OTHER INFORMATION: synthetic

<400> SEQUENCE: 104

Ala Arg Asp Gly Glu Ile Phe Gly Val Leu Ile Ser Ser Asp Ala Phe

Asp Ile

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105

```
gacatccaga tgacccagtc tccatcctcc ctgtctgcat ctgtaggaga cagagtcacc      60
atcacttgcc gggcaagtcg gggcattaga aatgatttag gctggtttca gcagaaacca     120
gggaaagccc ctaagcgcct gatctatgtt gcatccaatt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgatcac cttcggccaa     300
gggacacgac tggagattaa a                                               321
```

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Asn Asp
            20                  25                  30

Leu Gly Trp Phe Gln Gln Lys Pro Gly Lys Ala Pro Lys Arg Leu Ile
        35                  40                  45

Tyr Val Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Ile
                85                  90                  95

Thr Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cggggcatta gaaatgat                                                    18
```

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

```
Arg Gly Ile Arg Asn Asp
1               5
```

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gttgcatcc                                                                 9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

```
Val Ala Ser
1
```

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
ctacagcata atagttaccc gatcacc                                             27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

```
Leu Gln His Asn Ser Tyr Pro Ile Thr
1               5
```

<210> SEQ ID NO 113
<211> LENGTH: 354
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc tgggggaggc ttggtacagc ctgggggggtc cctgagactc      60 tcctgtgcag cctctggatt caccttcaga agctacgaca tgcactgggt ccgccaaggt      120
tcaggaaaag gtctggagtg ggtctcagct attggtactg ctggtgacac atactattta      180
ggctccgtga agggccgatt caccatctcc agagaaaatg ccaagaactc cttgtatctt      240
caaatgaaca gcctgagagc cggggacacg gctgtgtatt actgtgcaag agcgtggttc      300
ggggacgtat tcctggacta ctggggccag ggaaccctgg tcaccgtctc ctca            354

<210> SEQ ID NO 114
<211> LENGTH: 118
<212> TYPE: PRT

```
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Asp Met His Trp Val Arg Gln Gly Ser Gly Lys Gly Leu Glu Trp Val
        35                  40                  45

Ser Ala Ile Gly Thr Ala Gly Asp Thr Tyr Tyr Leu Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Trp Phe Gly Asp Val Phe Leu Asp Tyr Trp Gly Gln Gly Thr
            100                 105                 110

Leu Val Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggattcacct tcagaagcta cgac                                          24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Phe Thr Phe Arg Ser Tyr Asp
1               5

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117
attggtactg ctggtgacac a                                             21

<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Gly Thr Ala Gly Asp Thr
1               5
```

<210> SEQ ID NO 119
<211> LENGTH: 36
<212> TYPE: DNA
<213> ORGANISM: Artificial Sequence
<220> FEATURE:
<223> OTHER INFORMATION: synthetic

<400> SEQUENCE: 119
gcaagagcgt ggttcgggga cgtattcctg gactac        36

<210> SEQ ID NO 120
<211> LENGTH: 12
<212> TYPE: PRT
<213> ORGANISM: Artificial Sequence
<220> FEATURE:
<223> OTHER INFORMATION: synthetic

<400> SEQUENCE: 120

Ala Arg Ala Trp Phe Gly Asp Val Phe Leu Asp Tyr
1               5                   10

<210> SEQ ID NO 121
<211> LENGTH: 318
<212> TYPE: DNA
<213> ORGANISM: Artificial Sequence
<220> FEATURE:
<223> OTHER INFORMATION: synthetic

<400> SEQUENCE: 121
gaaatagtga tgacgcagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catatatggt gcatccacca gggccactgg tatcccagcc       180
aggttcagtg gcagtgggtc tgggacagag ttcactctca ccatcagcag cctgcagtct       240
gaagattttg caggctatta ctgtcagcag tataataaca ggctgacttt cggcggaggg       300
accaaggtgg agatcaaa                                                     318

<210> SEQ ID NO 122
<211> LENGTH: 106
<212> TYPE: PRT
<213> ORGANISM: Artificial Sequence
<220> FEATURE:
<223> OTHER INFORMATION: synthetic

<400> SEQUENCE: 122

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Gly Tyr Tyr Cys Gln Gln Tyr Asn Asn Arg Leu Thr
                85                  90                  95

Phe Gly Gly Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123
cagagtgtta gcagcaac                                                 18

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

Gln Ser Val Ser Ser Asn
1               5

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 ggtgcatcc                                                            9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Gly Ala Ser
1

<210> SEQ ID NO 127
<211> LENGTH: 24
<212> TYPE: DNA
<213> ORGANISM: Artificial Sequence
<220> FEATURE:
<223> OTHER INFORMATION: synthetic

<400> SEQUENCE: 127
cagcagtata ataacaggct gact                                          24

<210> SEQ ID NO 128
<211> LENGTH: 8
<212> TYPE: PRT
<213> ORGANISM: Artificial Sequence
<220> FEATURE:
<223> OTHER INFORMATION: synthetic

<400> SEQUENCE: 128

Gln Gln Tyr Asn Asn Arg Leu Thr
1               5

<210> SEQ ID NO 129
<211> LENGTH: 381
<212> TYPE: DNA

<213> ORGANISM: Artificial Sequence
<220> FEATURE:
<223> OTHER INFORMATION: synthetic

<400> SEQUENCE: 129

```
gaggtgcagc tggtggagtc tgggggaggc ttggtccagc ctggagggtc cctgagactc    60
tcctgtgcag cctctggatt caccttcagt gaccactaca tggtctgggt ccgccaggct   120
ccagggaagg ggctggagtg ggttggccgt actagaaaca agctaatag  ttatagcaca   180
gaatatgccg cgtctgtgaa aggcagattc accatctcaa gagatgattc aaagaagtca   240
ctgtatctgc aaatgaacag cctgaaaacc gaggacacgg ccgtgtatta ctgtgctaga   300
ggggggaaa  cactatggtt cggggagtcc aactacggta tggacgtctg gggccaaggg   360
accacggtca ccgtctcctc a                                             381
```

<210> SEQ ID NO 130
<211> LENGTH: 127
<212> TYPE: PRT
<213> ORGANISM: Artificial Sequence
<220> FEATURE:
<223> OTHER INFORMATION: synthetic

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Val Trp Val Arg Gln Ala Pro Gly Lys Gly Leu Glu Trp Val
        35                  40                  45

Gly Arg Thr Arg Asn Lys Ala Asn Ser Tyr Ser Thr Glu Tyr Ala Ala
    50                  55                  60

Ser Val Lys Gly Arg Phe Thr Ile Ser Arg Asp Asp Ser Lys Lys Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Gly Glu Thr Leu Trp Phe Gly Glu Ser Asn Tyr
            100                 105                 110

Gly Met Asp Val Trp Gly Gln Gly Thr Thr Val Thr Val Ser Ser
        115                 120                 125
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
ggattcacct tcagtgacca ctac                                           24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

```
Gly Phe Thr Phe Ser Asp His Tyr
1               5
```

<210> SEQ ID NO 133
<211> LENGTH: 30
<212> TYPE: DNA
<213> ORGANISM: Artificial Sequence
<220> FEATURE:
<223> OTHER INFORMATION: synthetic

<400> SEQUENCE: 133
actagaaaca aagctaatag ttatagcaca                                       30

<210> SEQ ID NO 134
<211> LENGTH: 10
<212> TYPE: PRT
<213> ORGANISM: Artificial Sequence
<220> FEATURE:
<223> OTHER INFORMATION: synthetic

<400> SEQUENCE: 134

Thr Arg Asn Lys Ala Asn Ser Tyr Ser Thr
1               5                   10

<210> SEQ ID NO 135
<211> LENGTH: 54
<212> TYPE: DNA
<213> ORGANISM: Artificial Sequence
<220> FEATURE:
<223> OTHER INFORMATION: synthetic

<400> SEQUENCE: 135
gctagagggg gggaaacact atggttcggg gagtccaact acggtatgga cgtc            54

<210> SEQ ID NO 136
<211> LENGTH: 18
<212> TYPE: PRT
<213> ORGANISM: Artificial Sequence
<220> FEATURE:
<223> OTHER INFORMATION: synthetic

<400> SEQUENCE: 136

Ala Arg Gly Gly Glu Thr Leu Trp Phe Gly Glu Ser Asn Tyr Gly Met
1               5                   10                  15

Asp Val

<210> SEQ ID NO 137
<211> LENGTH: 324
<212> TYPE: DNA
<213> ORGANISM: Artificial Sequence
<220> FEATURE:
<223> OTHER INFORMATION: synthetic

<400> SEQUENCE: 137
gaaattgtgt tgacgcagtc tccagacacc ctgtctttgt ctccagggga aagagccacc      60
ctctcctgca gggccagtca gagtgttagc agcacctact tagcctggta ccagcagaaa     120
cctggccagg ctcccagtct cctcatctat ggtgcatcca gcagggccac tggcatccca     180
gacaggttca gtggcagcgg gtctgggaca gacttcactc tcaccatcag cagactggag     240
cctgaagatt ttgcagtgta ttactgtcag cagtatggta ggtcacctct cactttcggc     300
ggagggacca aggtggagat caaa                                            324

<210> SEQ ID NO 138
<211> LENGTH: 108
<212> TYPE: PRT
<213> ORGANISM: Artificial Sequence
<220> FEATURE:
<223> OTHER INFORMATION: synthetic

<400> SEQUENCE: 138

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Leu Thr Phe Gly Gly Gly Thr Lys Val Glu Ile Lys
            100                 105

<210> SEQ ID NO 139
<211> LENGTH: 21
<212> TYPE: DNA
<213> ORGANISM: Artificial Sequence
<220> FEATURE:
<223> OTHER INFORMATION: synthetic

<400> SEQUENCE: 139
cagagtgtta gcagcaccta c                                          21

<210> SEQ ID NO 140
<211> LENGTH: 7
<212> TYPE: PRT
<213> ORGANISM: Artificial Sequence
<220> FEATURE:
<223> OTHER INFORMATION: synthetic

<400> SEQUENCE: 140

Gln Ser Val Ser Ser Thr Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 ggtgcatcc                                                         9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Gly Ala Ser
1

<210> SEQ ID NO 143
<211> LENGTH: 27

```
<212> TYPE: DNA
<213> ORGANISM: Artificial Sequence
<220> FEATURE:
<223> OTHER INFORMATION: synthetic

<400> SEQUENCE: 143
cagcagtatg gtaggtcacc tctcact                                           27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Tyr Gly Arg Ser Pro Leu Thr
1               5

<210> SEQ ID NO 145
<211> LENGTH: 348
<212> TYPE: DNA
<213> ORGANISM: Artificial Sequence
<220> FEATURE:
<223> OTHER INFORMATION: synthetic

<400> SEQUENCE: 145
caggtgcagc tggtggagtc tgggggaggc gtggtccagc ctggggaggtc cctgagactc        60 tcctgtgcag cgtctggctt caccttcaat aactatggca tgcactgggt ccgccaggct       120
ccaggcatgg ggctggagtg ggtggcagtt atatggcacg atggaagtga taaatactat       180
gcagactccg tgaagggccg attcaccatc tccagagaca attccaagaa cacgctgtat       240
ctgcaaatga acagcctgag agccgaggac acggctgtgt attactgtgc gagaaattgg       300
aacctctttg actactgggg ccagggaacc ctggtcactg tctcctca                    348

<210> SEQ ID NO 146
<211> LENGTH: 116
<212> TYPE: PRT
<213> ORGANISM: Artificial Sequence
<220> FEATURE:
<223> OTHER INFORMATION: synthetic

<400> SEQUENCE: 146

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Met Gly Leu Glu Trp Val
        35                  40                  45

Ala Val Ile Trp His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asn Leu Phe Asp Tyr Trp Gly Gln Gly Thr Leu Val
            100                 105                 110

Thr Val Ser Ser
        115
```

```
<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggcttcacct tcaataacta tggc                                             24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Phe Asn Asn Tyr Gly
1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atatggcacg atggaagtga taaa                                             24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Trp His Asp Gly Ser Asp Lys
1               5

<210> SEQ ID NO 151
<211> LENGTH: 27
<212> TYPE: DNA
<213> ORGANISM: Artificial Sequence
<220> FEATURE:
<223> OTHER INFORMATION: synthetic

<400> SEQUENCE: 151
gcgagaaatt ggaacctctt tgactac                                          27

<210> SEQ ID NO 152
<211> LENGTH: 9
<212> TYPE: PRT
<213> ORGANISM: Artificial Sequence
<220> FEATURE:
<223> OTHER INFORMATION: synthetic

<400> SEQUENCE: 152

Ala Arg Asn Trp Asn Leu Phe Asp Tyr
1               5

<210> SEQ ID NO 153
<211> LENGTH: 324
<212> TYPE: DNA
<213> ORGANISM: Artificial Sequence
```

<220> FEATURE:
<223> OTHER INFORMATION: synthetic

<400> SEQUENCE: 153

```
gacatccaga tgacccagtc tccatcctcc ctgtctgcat ctgtaggaga cagaatcacc    60
atcacttgcc gggcaagtca gagcatcagc acctatttac attggtatca gcagaaacca   120
gggaaagccc ctaagctcct gatctatgct gcatccactt tgcagagtgg ggtcccatca   180
aggttcagtg gcagtggatc tgggacagat ttcactctca ccatcagcag tctgcaacct   240
gaagattttg caacttacta ctgtcaacag agtttcagta cccctccgat aaacttcggc   300
caagggacca agctggagat caaa                                          324
```

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

```
Asp Ile Gln Met Thr Gln Ser Pro Ser Ser Leu Ser Ala Ser Val Gly
1               5                   10                  15
Asp Arg Ile Thr Ile Thr Cys Arg Ala Ser Gln Ser Ile Ser Thr Tyr
            20                  25                  30
Leu His Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Phe Ser Thr Pro Pro
                85                  90                  95
Ile Asn Phe Gly Gln Gly Thr Lys Leu Glu Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155

```
cagagcatca gcacctat                                                  18
```

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

```
Gln Ser Ile Ser Thr Tyr
1               5
```

<210> SEQ ID NO 157
<211> LENGTH: 9
<212> TYPE: DNA
<213> ORGANISM: Artificial Sequence
<220> FEATURE:

<223> OTHER INFORMATION: synthetic

<400> SEQUENCE: 157 gctgcatcc                                                                                              9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 30
<212> TYPE: DNA
<213> ORGANISM: Artificial Sequence
<220> FEATURE:
<223> OTHER INFORMATION: synthetic

<400> SEQUENCE: 159
caacagagtt tcagtacccc tccgataaac                                                                       30

<210> SEQ ID NO 160
<211> LENGTH: 10
<212> TYPE: PRT
<213> ORGANISM: Artificial Sequence
<220> FEATURE:
<223> OTHER INFORMATION: synthetic

<400> SEQUENCE: 160

Gln Gln Ser Phe Ser Thr Pro Pro Ile Asn
1               5                   10

<210> SEQ ID NO 161
<211> LENGTH: 384
<212> TYPE: DNA
<213> ORGANISM: Artificial Sequence
<220> FEATURE:
<223> OTHER INFORMATION: synthetic

<400> SEQUENCE: 161
gaggtgcagc tggtggagtc tgggggaggc ttggtccagc ctggggggtc cctgagactc       60
tcctgtgcag cctctaaatt cacctttgac acctttgcca tgagctgggt ccgccaggct      120
ccagggaagg ggttggaatg ggtctcattt attagtagtt ctggtggtcg cacagactat      180
gtagactccg tgaagggccg gttcaccatc tccagagaca attccaagaa cacccttgtat    240 ctgcaaatga acagcctgcg agccgaggac acggccgtat attactgtgc gaaagaacgg     300 acgattttg gagtgcttat tctgggcccc gacaactacg gtatggacgt ctggggccaa      360
gggaccacgg tcaccgtctc ctca                                            384

<210> SEQ ID NO 162
<211> LENGTH: 128
<212> TYPE: PRT
<213> ORGANISM: Artificial Sequence
<220> FEATURE:
<223> OTHER INFORMATION: synthetic

<400> SEQUENCE: 162

Glu Val Gln Leu Val Glu Ser Gly Gly Gly Leu Val Gln Pro Gly Gly

```
  1               5                  10                 15
Ser Leu Arg Leu Ser Cys Ala Ala Ser Lys Phe Thr Phe Asp Thr Phe
                 20                  25                 30

Ala Met Ser Trp Val Arg Gln Ala Pro Gly Lys Gly Leu Glu Trp Val
                 35                  40                 45

Ser Phe Ile Ser Ser Gly Gly Arg Thr Asp Tyr Val Asp Ser Val
         50                  55                  60

Lys Gly Arg Phe Thr Ile Ser Arg Asp Asn Ser Lys Asn Thr Leu Tyr
 65                  70                  75                 80

Leu Gln Met Asn Ser Leu Arg Ala Glu Asp Thr Ala Val Tyr Tyr Cys
                 85                  90                 95

Ala Lys Glu Arg Thr Ile Phe Gly Val Leu Ile Leu Gly Pro Asp Asn
                100                 105                110

Tyr Gly Met Asp Val Trp Gly Gln Gly Thr Thr Val Thr Val Ser Ser
                115                 120                125
```

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
aaattcacct tgacaccttt tgcc                                        24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Lys Phe Thr Phe Asp Thr Phe Ala
 1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
attagtagtt ctggtggtcg caca                                        24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Ser Ser Ser Gly Gly Arg Thr
 1               5

<210> SEQ ID NO 167
<211> LENGTH: 63
<212> TYPE: DNA
<213> ORGANISM: Artificial Sequence
<220> FEATURE:

<223> OTHER INFORMATION: synthetic

<400> SEQUENCE: 167
gcgaaagaac ggacgatttt tggagtgctt attctgggcc ccgacaacta cggtatggac    60
gtc                                                                 63

<210> SEQ ID NO 168
<211> LENGTH: 21
<212> TYPE: PRT
<213> ORGANISM: Artificial Sequence
<220> FEATURE:
<223> OTHER INFORMATION: synthetic

<400> SEQUENCE: 168

Ala Lys Glu Arg Thr Ile Phe Gly Val Leu Ile Leu Gly Pro Asp Asn
1               5                   10                  15

Tyr Gly Met Asp Val
            20

<210> SEQ ID NO 169
<211> LENGTH: 324
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcctcc ctgtctgcat ttgtaggaga cagagtcacc    60
atcacttgcc gggcaagtca gagcattagc acctatttaa attggtatca gcaaaaacca   120
gggaaagccc ctaaactcct gatctatgct gcatccagtt tgcaaagtgg ggtctcatca   180
aggttcagtg gcagtggatc tgggacagat ttcactctca ccatcagcag tctgcaacct   240
gaagattttg caacttacta ctgtcaacag agttacagtg cccctccgat caccttcggc   300
caagggacac gactggagat taaa                                          324

<210> SEQ ID NO 170
<211> LENGTH: 108
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Pro
                85                  90                  95

Ile Thr Phe Gly Gln Gly Thr Arg Leu Glu Ile Lys
            100                 105

<210> SEQ ID NO 171

```
<211> LENGTH: 18
<212> TYPE: DNA
<213> ORGANISM: Artificial Sequence
<220> FEATURE:
<223> OTHER INFORMATION: synthetic

<400> SEQUENCE: 171
cagagcatta gcacctat                                                     18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Ser Ile Ser Thr Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gctgcatcc                                                                9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
1

<210> SEQ ID NO 175
<211> LENGTH: 30
<212> TYPE: DNA
<213> ORGANISM: Artificial Sequence
<220> FEATURE:
<223> OTHER INFORMATION: synthetic

<400> SEQUENCE: 175
caacagagtt acagtgcccc tccgatcacc                                        30

<210> SEQ ID NO 176
<211> LENGTH: 10
<212> TYPE: PRT
<213> ORGANISM: Artificial Sequence
<220> FEATURE:
<223> OTHER INFORMATION: synthetic

<400> SEQUENCE: 176

Gln Gln Ser Tyr Ser Ala Pro Pro Ile Thr
1               5                   10

<210> SEQ ID NO 177
<211> LENGTH: 384
<212> TYPE: DNA
<213> ORGANISM: Artificial Sequence
<220> FEATURE:
```

<223> OTHER INFORMATION: synthetic

<400> SEQUENCE: 177

```
caggtacagc tgcagcagtc aggtccagga ctggtgaagc cctcgcagac cctctcactc      60
acctgtgcca tctccgggga cagtgtctct agcaacattc ctgcttggaa ctggatcagg     120
cagtcccctt cgagaggcct tgagtggctg ggaaggacat actacaggtc caagtggtat     180
aatgattatg cagtatctgt gaaaagtcga ataaccatca atccagacac atccaagaac     240
cacttctccc tgcagctgaa ctctgtgact cccgaggaca cggctgtgta ttactgtgca     300
agaggaaggg tctatgacag gtcttctagg tacttctacg ctatggacgt ctggggccaa     360
gggaccacgg tcaccgtctc ctca                                            384
```

<210> SEQ ID NO 178
<211> LENGTH: 128
<212> TYPE: PRT
<213> ORGANISM: Artificial Sequence
<220> FEATURE:
<223> OTHER INFORMATION: synthetic

<400> SEQUENCE: 178

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ile Pro Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

His Phe Ser Leu Gln Leu Asn Ser Val Thr Pro Glu Asp Thr Ala Val
                85                  90                  95

Tyr Tyr Cys Ala Arg Gly Arg Val Tyr Asp Arg Ser Ser Arg Tyr Phe
            100                 105                 110

Tyr Ala Met Asp Val Trp Gly Gln Gly Thr Thr Val Thr Val Ser Ser
        115                 120                 125

<210> SEQ ID NO 179
<211> LENGTH: 30
<212> TYPE: DNA
<213> ORGANISM: Artificial Sequence
<220> FEATURE:
<223> OTHER INFORMATION: synthetic

<400> SEQUENCE: 179

```
ggggacagtg tctctagcaa cattcctgct                                       30
```

<210> SEQ ID NO 180
<211> LENGTH: 10
<212> TYPE: PRT
<213> ORGANISM: Artificial Sequence
<220> FEATURE:
<223> OTHER INFORMATION: synthetic

<400> SEQUENCE: 180

Gly Asp Ser Val Ser Ser Asn Ile Pro Ala
1               5                   10

<210> SEQ ID NO 181

<211> LENGTH: 27
<212> TYPE: DNA
<213> ORGANISM: Artificial Sequence
<220> FEATURE:
<223> OTHER INFORMATION: synthetic

<400> SEQUENCE: 181
acatactaca ggtccaagtg gtataat        27

<210> SEQ ID NO 182
<211> LENGTH: 9
<212> TYPE: PRT
<213> ORGANISM: Artificial Sequence
<220> FEATURE:
<223> OTHER INFORMATION: synthetic

<400> SEQUENCE: 182

Thr Tyr Tyr Arg Ser Lys Trp Tyr Asn
1               5

<210> SEQ ID NO 183
<211> LENGTH: 54
<212> TYPE: DNA
<213> ORGANISM: Artificial Sequence
<220> FEATURE:
<223> OTHER INFORMATION: synthetic

<400> SEQUENCE: 183
gcaagaggaa gggtctatga caggtcttct aggtacttct acgctatgga cgtc        54

<210> SEQ ID NO 184
<211> LENGTH: 18
<212> TYPE: PRT
<213> ORGANISM: Artificial Sequence
<220> FEATURE:
<223> OTHER INFORMATION: synthetic

<400> SEQUENCE: 184

Ala Arg Gly Arg Val Tyr Asp Arg Ser Ser Arg Tyr Phe Tyr Ala Met
1               5                   10                  15

Asp Val

<210> SEQ ID NO 185
<211> LENGTH: 324
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcaacag agttacagta attatccgat caccttcggc       300
caagggacac gactggagat taaa                                              324

<210> SEQ ID NO 186
<211> LENGTH: 108
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Tyr Pro
                85                  90                  95

Ile Thr Phe Gly Gln Gly Thr Arg Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagagcatta gcagctat                                              18

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

Gln Ser Ile Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gctgcatcc                                                         9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Ala Ala Ser
1

<210> SEQ ID NO 191
<211> LENGTH: 30
<212> TYPE: DNA
<213> ORGANISM: Artificial Sequence
<220> FEATURE:
<223> OTHER INFORMATION: synthetic

<400> SEQUENCE: 191
caacagagtt acagtaatta tccgatcacc                                    30

<210> SEQ ID NO 192
<211> LENGTH: 10
<212> TYPE: PRT
<213> ORGANISM: Artificial Sequence
<220> FEATURE:
<223> OTHER INFORMATION: synthetic

<400> SEQUENCE: 192

Gln Gln Ser Tyr Ser Asn Tyr Pro Ile Thr
1               5                   10

<210> SEQ ID NO 193
<211> LENGTH: 357
<212> TYPE: DNA
<213> ORGANISM: Artificial Sequence
<220> FEATURE:
<223> OTHER INFORMATION: synthetic

<400> SEQUENCE: 193
gaggtgcagc tggtggagtc tgggggaggc ttggttcagc cggggggtc cctgagactc       60 tcctgtgcag cctctggatt caccttcaga acctacgaca tgcactgggt ccgccaagct     120
acaggaaaag gtctggagtg ggtctcagct attggtactg ctggtgacac atactatcca     180
ggctccgtga agggccgatt caccatctcc agagaaaatg ccaagaactc cttgtatctt     240
caaatgaaca gcctgagagc cggtgacacg gctgtgtatt actgtgcacg aacgattttt     300
ggagtggttc ttacctttga ctactggggc cagggaaccc tggtcaccgt ctcctca       357

<210> SEQ ID NO 194
<211> LENGTH: 119
<212> TYPE: PRT
<213> ORGANISM: Artificial Sequence
<220> FEATURE:
<223> OTHER INFORMATION: synthetic

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Thr Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Thr Ile Phe Gly Val Val Leu Thr Phe Asp Tyr Trp Gly Gln Gly
            100                 105                 110

Thr Leu Val Thr Val Ser Ser
        115

<210> SEQ ID NO 195
<211> LENGTH: 24

```
<212> TYPE: DNA
<213> ORGANISM: Artificial Sequence
<220> FEATURE:
<223> OTHER INFORMATION: synthetic

<400> SEQUENCE: 195
ggattcacct tcagaaccta cgac                                           24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gly Phe Thr Phe Arg Thr Tyr Asp
1               5

<210> SEQ ID NO 197
<211> LENGTH: 21
<212> TYPE: DNA
<213> ORGANISM: Artificial Sequence
<220> FEATURE:
<223> OTHER INFORMATION: synthetic

<400> SEQUENCE: 197
attggtactg ctggtgacac a                                              21

<210> SEQ ID NO 198
<211> LENGTH: 7
<212> TYPE: PRT
<213> ORGANISM: Artificial Sequence
<220> FEATURE:
<223> OTHER INFORMATION: synthetic

<400> SEQUENCE: 198

Ile Gly Thr Ala Gly Asp Thr
1               5

<210> SEQ ID NO 199
<211> LENGTH: 39
<212> TYPE: DNA
<213> ORGANISM: Artificial Sequence
<220> FEATURE:
<223> OTHER INFORMATION: synthetic

<400> SEQUENCE: 199
gcacgaacga tttttggagt ggttcttacc tttgactac                           39

<210> SEQ ID NO 200
<211> LENGTH: 13
<212> TYPE: PRT
<213> ORGANISM: Artificial Sequence
<220> FEATURE:
<223> OTHER INFORMATION: synthetic

<400> SEQUENCE: 200

Ala Arg Thr Ile Phe Gly Val Val Leu Thr Phe Asp Tyr
1               5                   10

<210> SEQ ID NO 201
<211> LENGTH: 324
<212> TYPE: DNA
<213> ORGANISM: Artificial Sequence
<220> FEATURE:
<223> OTHER INFORMATION: synthetic
```

<400> SEQUENCE: 201
gacatccaga tgacccagtc tccatcctcc ctgtctgcat ctgtaggaga cagagtcacc    60
atcacttgcc gggcaagtca gagcattagc agctctttaa attggtatca gcagaaacca   120
gggaaagccc ctaagctcct gatctatgct gcatccagtt tgcacagtgg ggtcccatca   180
aggttcagtg gcagtggatc tgggacagat ttcactctca ccatcagcag tctgcaacct   240
gaagattttg caacttacta ctgtcaacag acttacagta tccctccgac caccttcggc   300
caagggacca aggtggaaat caaa                                          324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ile Pro Pro
                85                  90                  95

Thr Thr Phe Gly Gln Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagagcatta gcagctct                                                  18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Ser Ile Ser Ser Ser
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                                    9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
1

<210> SEQ ID NO 207
<211> LENGTH: 30
<212> TYPE: DNA
<213> ORGANISM: Artificial Sequence
<220> FEATURE:
<223> OTHER INFORMATION: synthetic

<400> SEQUENCE: 207
caacagactt acagtatccc tccgaccacc                                             30

<210> SEQ ID NO 208
<211> LENGTH: 10
<212> TYPE: PRT
<213> ORGANISM: Artificial Sequence
<220> FEATURE:
<223> OTHER INFORMATION: synthetic

<400> SEQUENCE: 208

Gln Gln Thr Tyr Ser Ile Pro Pro Thr Thr
1               5                   10

<210> SEQ ID NO 209
<211> LENGTH: 384
<212> TYPE: DNA
<213> ORGANISM: Artificial Sequence
<220> FEATURE:
<223> OTHER INFORMATION: synthetic

<400> SEQUENCE: 209
gaggtgcagc tggtggagtc tgggggaggc ttggtacagc ctgggggtc cctgagactc             60 tcctgtgcag cctctggatt cacctttagc aactatgcca tgatctgggt ccgccaggct           120
ccagggaagg gctggagtg gtctcaggt attagtggta gtggtggcag tatatactac             180
gcagactccg tgaagggccg gttcaccatc tccagagaca attccaagaa cacgctgtat           240
ctgcaaatga acagcctgag agccgaggac acggccgtat attactgtgc gaaagaagga           300
attattagta tggttcgggg acttatcaac tactaccacg gtatggacgt ctggggccaa           360
gggaccacgg tcaccgtctc ctca                                                 384

<210> SEQ ID NO 210
<211> LENGTH: 128
<212> TYPE: PRT
<213> ORGANISM: Artificial Sequence
<220> FEATURE:
<223> OTHER INFORMATION: synthetic

<400> SEQUENCE: 210

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asn Tyr
         20                  25                  30

Ala Met Ile Trp Val Arg Gln Ala Pro Gly Lys Gly Leu Glu Trp Val
         35                  40                  45

Ser Gly Ile Ser Gly Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Ile Ile Ser Met Val Arg Gly Leu Ile Asn Tyr Tyr
            100                 105                 110

His Gly Met Asp Val Trp Gly Gln Gly Thr Thr Val Thr Val Ser Ser
        115                 120                 125
```

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct ttagcaacta tgcc                                     24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

```
Gly Phe Thr Phe Ser Asn Tyr Ala
 1               5
```

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
attagtggta gtggtggcag tata                                     24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

```
Ile Ser Gly Ser Gly Gly Ser Ile
 1               5
```

<210> SEQ ID NO 215
<211> LENGTH: 63
<212> TYPE: DNA
<213> ORGANISM: Artificial Sequence
<220> FEATURE:
<223> OTHER INFORMATION: synthetic

<400> SEQUENCE: 215
gcgaaagaag gaattattag tatggttcgg ggacttatca actactacca cggtatggac    60
gtc    63

<210> SEQ ID NO 216
<211> LENGTH: 21
<212> TYPE: PRT
<213> ORGANISM: Artificial Sequence
<220> FEATURE:
<223> OTHER INFORMATION: synthetic

<400> SEQUENCE: 216

Ala Lys Glu Gly Ile Ile Ser Met Val Arg Gly Leu Ile Asn Tyr Tyr
1               5                   10                  15

His Gly Met Asp Val
            20

<210> SEQ ID NO 217
<211> LENGTH: 324
<212> TYPE: DNA
<213> ORGANISM: Artificial Sequence
<220> FEATURE:
<223> OTHER INFORMATION: synthetic

<400> SEQUENCE: 217
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccttg gacgttcggc   300
caagggacca aggtggaaat caaa   324

<210> SEQ ID NO 218
<211> LENGTH: 108
<212> TYPE: PRT
<213> ORGANISM: Artificial Sequence
<220> FEATURE:
<223> OTHER INFORMATION: synthetic

<400> SEQUENCE: 218

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 219
<211> LENGTH: 21
<212> TYPE: DNA

```
<213> ORGANISM: Artificial Sequence
<220> FEATURE:
<223> OTHER INFORMATION: synthetic

<400> SEQUENCE: 219
cagagtgtta gcagcagcta c                                      21

<210> SEQ ID NO 220
<211> LENGTH: 7
<212> TYPE: PRT
<213> ORGANISM: Artificial Sequence
<220> FEATURE:
<223> OTHER INFORMATION: synthetic

<400> SEQUENCE: 220

Gln Ser Val Ser Ser Ser Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 ggtgcatcc                                                     9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
cagcagtatg gtagctcacc ttggacg                                27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Tyr Gly Ser Ser Pro Trp Thr
1               5

<210> SEQ ID NO 225
<211> LENGTH: 360
<212> TYPE: DNA
<213> ORGANISM: Artificial Sequence
<220> FEATURE:
<223> OTHER INFORMATION: synthetic
```

<400> SEQUENCE: 225
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gttgggaata atcaaccctagt ggtggtag cacaagctac   180 gcacagaagt tccagggcag agtcaccatg accagggaca cgtccacgag cacagtctac   240
atggagctga gcagcctgag atctgaggac acggccgtgt attactgtgc gagagagaca   300
ggagaagctg gtgaggtttt taactactgg ggccaggaa cccaggtcac cgtctcctca    360

<210> SEQ ID NO 226
<211> LENGTH: 120
<212> TYPE: PRT
<213> ORGANISM: Artificial Sequence
<220> FEATURE:
<223> OTHER INFORMATION: synthetic

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Leu
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Gly Glu Ala Gly Glu Val Phe Asn Tyr Trp Gly Gln
            100                 105                 110

Gly Thr Gln Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggatacacct tcaccagcta ctat                                           24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gly Tyr Thr Phe Thr Ser Tyr Tyr
1               5

<210> SEQ ID NO 229
<211> LENGTH: 24
<212> TYPE: DNA
<213> ORGANISM: Artificial Sequence
<220> FEATURE:

<223> OTHER INFORMATION: synthetic

<400> SEQUENCE: 229
atcaacccta gtggtggtag caca                                              24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Asn Pro Ser Gly Gly Ser Thr
1               5

<210> SEQ ID NO 231
<211> LENGTH: 39
<212> TYPE: DNA
<213> ORGANISM: Artificial Sequence
<220> FEATURE:
<223> OTHER INFORMATION: synthetic

<400> SEQUENCE: 231
gcgagagaga caggagaagc tggtgaggtt tttaactac                              39

<210> SEQ ID NO 232
<211> LENGTH: 13
<212> TYPE: PRT
<213> ORGANISM: Artificial Sequence
<220> FEATURE:
<223> OTHER INFORMATION: synthetic

<400> SEQUENCE: 232

Ala Arg Glu Thr Gly Glu Ala Gly Glu Val Phe Asn Tyr
1               5                   10

<210> SEQ ID NO 233
<211> LENGTH: 324
<212> TYPE: DNA
<213> ORGANISM: Artificial Sequence
<220> FEATURE:
<223> OTHER INFORMATION: synthetic

<400> SEQUENCE: 233
gacatccaga tgacccagtc tccatcctcc ctgtctgcat ctgtaggaga cagagtcacc        60
atcacttgcc gggcaagtca gatcattagc aggtatttaa attggtatca gcataaacca      120
gggaaagccc ctaaggtcct gatctatgct gcctccactt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 234
<211> LENGTH: 108
<212> TYPE: PRT
<213> ORGANISM: Artificial Sequence
<220> FEATURE:
<223> OTHER INFORMATION: synthetic

<400> SEQUENCE: 234

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ile Ile Ser Arg Tyr
            20                  25                  30

Leu Asn Trp Tyr Gln His Lys Pro Gly Lys Ala Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235
cagatcatta gcaggtat                                               18

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

```
Gln Ile Ile Ser Arg Tyr
1               5
```

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcctcc                                                          9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

```
Ala Ala Ser
1
```

<210> SEQ ID NO 239
<211> LENGTH: 30
<212> TYPE: DNA
<213> ORGANISM: Artificial Sequence
<220> FEATURE:
<223> OTHER INFORMATION: synthetic

<400> SEQUENCE: 239
caacagagtt acagtacccc tccgatcacc                                  30

<210> SEQ ID NO 240
<211> LENGTH: 10
<212> TYPE: PRT
<213> ORGANISM: Artificial Sequence
<220> FEATURE:
<223> OTHER INFORMATION: synthetic

<400> SEQUENCE: 240

Gln Gln Ser Tyr Ser Thr Pro Pro Ile Thr
1               5                   10

<210> SEQ ID NO 241
<211> LENGTH: 381
<212> TYPE: DNA
<213> ORGANISM: Artificial Sequence
<220> FEATURE:
<223> OTHER INFORMATION: synthetic

<400> SEQUENCE: 241
gaggtgcagc tggtggagtc tgggggaggc ttggtacagc ctggagggtc cctgagactc      60
tcctgtgcag cctctggatt caccttcagt agttatgaaa tgaactgggt ccgccaggct     120
ccagggaagg ggctggagtg ggtttcatac attggtagta gtggtcgtgc cacatactac     180
gcagactctg tgaagggccg attcaccatc tccagagaca acgccaaaaa ctcactgtat     240
ctgcaaatga acagcctgag agccgaggac acggctgttt attactgtgc gagaccttcg     300
agcatagcag ctctgttacg gaaccagtac cacttcggta tggacgtctg gggccaaggg     360
accacggtca ccgtctcctc a                                               381

<210> SEQ ID NO 242
<211> LENGTH: 127
<212> TYPE: PRT
<213> ORGANISM: Artificial Sequence
<220> FEATURE:
<223> OTHER INFORMATION: synthetic

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Gly Ser Ser Gly Arg Ala Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Ser Ser Ile Ala Ala Leu Leu Arg Asn Gln Tyr His Phe
            100                 105                 110

Gly Met Asp Val Trp Gly Gln Gly Thr Thr Val Thr Val Ser Ser
        115                 120                 125

<210> SEQ ID NO 243
<211> LENGTH: 24
<212> TYPE: DNA
<213> ORGANISM: Artificial Sequence
<220> FEATURE:
<223> OTHER INFORMATION: synthetic

```
<400> SEQUENCE: 243
ggattcacct tcagtagtta tgaa                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Ser Ser Tyr Glu
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
attggtagta gtggtcgtgc caca                                          24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Gly Ser Ser Gly Arg Ala Thr
1               5

<210> SEQ ID NO 247
<211> LENGTH: 60
<212> TYPE: DNA
<213> ORGANISM: Artificial Sequence
<220> FEATURE:
<223> OTHER INFORMATION: synthetic

<400> SEQUENCE: 247
gcgagacctt cgagcatagc agctctgtta cggaaccagt accacttcgg tatggacgtc   60

<210> SEQ ID NO 248
<211> LENGTH: 20
<212> TYPE: PRT
<213> ORGANISM: Artificial Sequence
<220> FEATURE:
<223> OTHER INFORMATION: synthetic

<400> SEQUENCE: 248

Ala Arg Pro Ser Ser Ile Ala Ala Leu Leu Arg Asn Gln Tyr His Phe
1               5                   10                  15

Gly Met Asp Val
            20

<210> SEQ ID NO 249
<211> LENGTH: 324
<212> TYPE: DNA
<213> ORGANISM: Artificial Sequence
<220> FEATURE:
<223> OTHER INFORMATION: synthetic
```

<400> SEQUENCE: 249

```
gacatccaga tgacccagtc tccatcctcc ctgtctgcat ctgtaggaga cagagtcacc      60
atcacttgcc gggcaagtca gagcattacc agctatttaa attggtatca gcagaaacca    120
gggaaagccc ctaagctcct gatctatgct gcatccagtt tgcaaggtgg ggtcccatca    180
aggttcagtg gcagtggatc tgggacagat tcactctca ccatcagcag tctgcaacct    240
gaagattttg caacttacta ctgtcaacag agttacagta cccctccgat caccttcggc    300
caagggacac gactggagat taaa                                            324
```

<210> SEQ ID NO 250
<211> LENGTH: 108
<212> TYPE: PRT
<213> ORGANISM: Artificial Sequence
<220> FEATURE:
<223> OTHER INFORMATION: synthetic

<400> SEQUENCE: 250

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251

```
cagagcatta ccagctat                                                    18
```

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

```
Gln Ser Ile Thr Ser Tyr
1               5
```

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gctgcatcc                                                                  9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Ala Ala Ser
1

<210> SEQ ID NO 255
<211> LENGTH: 30
<212> TYPE: DNA
<213> ORGANISM: Artificial Sequence
<220> FEATURE:
<223> OTHER INFORMATION: synthetic

<400> SEQUENCE: 255
caacagagtt acagtacccc tccgatcacc                                           30

<210> SEQ ID NO 256
<211> LENGTH: 10
<212> TYPE: PRT
<213> ORGANISM: Artificial Sequence
<220> FEATURE:
<223> OTHER INFORMATION: synthetic

<400> SEQUENCE: 256

Gln Gln Ser Tyr Ser Thr Pro Pro Ile Thr
1               5                   10

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257
caggtgcagc tggtgcagtc tggggctgag gtgaagaagc ctggggcctc agtgaaggtt          60
tcctgcaagg catctggata caccttcacc agctactata tgcactgggt gcgacaggcc         120
cctggacaag gcttgagtg gatgggaata tcaaccccta gtggtggtag cacaagctac          180
gcacagaagt tccagggcag agtcaccatg accagggaca cgtccacgag cacagtctac         240
atggagctga gcagcctgag atctgaggac acggccgtgt attactgtgc gagagagata         300
ggagaagctg gtgaagtttt taactactgg ggccagggaa ccctggtcac cgtctcctca         360

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ile Gly Glu Ala Gly Val Phe Asn Tyr Trp Gly Gln
             100                 105                 110

Gly Thr Leu Val Thr Val Ser Ser
         115                 120

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259
ggatacacct tcaccagcta ctat                                         24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gly Tyr Thr Phe Thr Ser Tyr Tyr
 1               5

<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261
atcaacccta gtggtggtag caca                                         24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Ile Asn Pro Ser Gly Gly Ser Thr
 1               5

<210> SEQ ID NO 263
<211> LENGTH: 39
<212> TYPE: DNA
<213> ORGANISM: Artificial Sequence
<220> FEATURE:
<223> OTHER INFORMATION: synthetic

<400> SEQUENCE: 263
gcgagagaga taggagaagc tggtgaagtt tttaactac                         39

<210> SEQ ID NO 264
<211> LENGTH: 13
<212> TYPE: PRT
<213> ORGANISM: Artificial Sequence
<220> FEATURE:
<223> OTHER INFORMATION: synthetic

<400> SEQUENCE: 264

Ala Arg Glu Ile Gly Glu Ala Gly Glu Val Phe Asn Tyr
1               5                   10

<210> SEQ ID NO 265
<211> LENGTH: 324
<212> TYPE: DNA
<213> ORGANISM: Artificial Sequence
<220> FEATURE:
<223> OTHER INFORMATION: synthetic

<400> SEQUENCE: 265
gacatccaga tgacccagtc tccatcctcc ctgtctgcat ctgtaggaga cagagtcacc    60
atcacttgcc gggcaagtca gagcattagc aggtatttaa attggtatca gcataaacca   120
gggaaagccc ctaaggtcct gatctatgct gcatccattt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 266
<211> LENGTH: 108
<212> TYPE: PRT
<213> ORGANISM: Artificial Sequence
<220> FEATURE:
<223> OTHER INFORMATION: synthetic

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln His Lys Pro Gly Lys Ala Pro Lys Val Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
cagagcatta gcaggtat                                                  18

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

Gln Ser Ile Ser Arg Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gctgcatcc                                                                 9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Ala Ala Ser
1

<210> SEQ ID NO 271
<211> LENGTH: 30
<212> TYPE: DNA
<213> ORGANISM: Artificial Sequence
<220> FEATURE:
<223> OTHER INFORMATION: synthetic

<400> SEQUENCE: 271
caacagagtt acagtacccc tccgatcacc                                         30

<210> SEQ ID NO 272
<211> LENGTH: 10
<212> TYPE: PRT
<213> ORGANISM: Artificial Sequence
<220> FEATURE:
<223> OTHER INFORMATION: synthetic

<400> SEQUENCE: 272

Gln Gln Ser Tyr Ser Thr Pro Pro Ile Thr
1               5                   10

<210> SEQ ID NO 273
<211> LENGTH: 381
<212> TYPE: DNA
<213> ORGANISM: Artificial Sequence
<220> FEATURE:
<223> OTHER INFORMATION: synthetic

<400> SEQUENCE: 273
gaggtgcagc tggtggagtc tgggggaggc ttggtacagc ctggagggtc cctgagactc        60
tcctgtgcag cctctggatt caccttcagt acttatgaaa tgaactgggt ccgccaggct      120
ccagggaagg ggctggagtg ggtttcatat agtagtagta gtggtagaac catatactac      180

```
gcagactctg tgaagggccg attcaccatc tccagagaca acgccaagaa ctcactgttt    240
ctgcaaatga acagcctgag agccgaggac acggctgttt attactgtgc gagaccttcg    300
agtatagaga ctctgttacg gaatcagtac cactacggtg tggacgtctg gggccaaggg    360
accacggtca ccgtctcctc a                                              381

<210> SEQ ID NO 274
<211> LENGTH: 127
<212> TYPE: PRT
<213> ORGANISM: Artificial Sequence
<220> FEATURE:
<223> OTHER INFORMATION: synthetic

<400> SEQUENCE: 274

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Lys Gly Leu Glu Trp Val
        35                  40                  45

Ser Tyr Ser Ser Ser Ser Gly Arg Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Pro Ser Ser Ile Glu Thr Leu Leu Arg Asn Gln Tyr His Tyr
            100                 105                 110

Gly Val Asp Val Trp Gly Gln Gly Thr Thr Val Thr Val Ser Ser
        115                 120                 125

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
ggattcacct tcagtactta tgaa                                            24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Phe Thr Phe Ser Thr Tyr Glu
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
agtagtagta gtggtagaac cata                                            24
```

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ser Ser Ser Ser Gly Arg Thr Ile
1               5

<210> SEQ ID NO 279
<211> LENGTH: 60
<212> TYPE: DNA
<213> ORGANISM: Artificial Sequence
<220> FEATURE:
<223> OTHER INFORMATION: synthetic

<400> SEQUENCE: 279
gcgagacctt cgagtataga gactctgtta cggaatcagt accactacgg tgtggacgtc    60

<210> SEQ ID NO 280
<211> LENGTH: 20
<212> TYPE: PRT
<213> ORGANISM: Artificial Sequence
<220> FEATURE:
<223> OTHER INFORMATION: synthetic

<400> SEQUENCE: 280

Ala Arg Pro Ser Ser Ile Glu Thr Leu Leu Arg Asn Gln Tyr His Tyr
1               5                   10                  15

Gly Val Asp Val
            20

<210> SEQ ID NO 281
<211> LENGTH: 324
<212> TYPE: DNA
<213> ORGANISM: Artificial Sequence
<220> FEATURE:
<223> OTHER INFORMATION: synthetic

<400> SEQUENCE: 281
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 282
<211> LENGTH: 108
<212> TYPE: PRT
<213> ORGANISM: Artificial Sequence
<220> FEATURE:
<223> OTHER INFORMATION: synthetic

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
             35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Pro
                 85                  90                  95
Ile Thr Phe Gly Gln Gly Thr Arg Leu Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: synthetic

<400> SEQUENCE: 283
cagagcatta gcagctat            18

<210> SEQ ID NO 284
<211> LENGTH: 6
<212> TYPE: PRT
<213> ORGANISM: Artificial Sequence
<220> FEATURE:
<223> OTHER INFORMATION: synthetic

<400> SEQUENCE: 284

```
Gln Ser Ile Ser Ser Tyr
 1               5
```

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 gctgcatcc            9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

```
Ala Ala Ser
 1
```

<210> SEQ ID NO 287
<211> LENGTH: 30
<212> TYPE: DNA
<213> ORGANISM: Artificial Sequence
<220> FEATURE:
<223> OTHER INFORMATION: synthetic

<400> SEQUENCE: 287
caacagagtt acagtacccc tccgatcacc            30

<210> SEQ ID NO 288

<210> SEQ ID NO 288
<211> LENGTH: 10
<212> TYPE: PRT
<213> ORGANISM: Artificial Sequence
<220> FEATURE:
<223> OTHER INFORMATION: synthetic

<400> SEQUENCE: 288

Gln Gln Ser Tyr Ser Thr Pro Pro Ile Thr
1               5                   10

<210> SEQ ID NO 289
<211> LENGTH: 384
<212> TYPE: DNA
<213> ORGANISM: Artificial Sequence
<220> FEATURE:
<223> OTHER INFORMATION: synthetic

<400> SEQUENCE: 289
gaggtgcagc tggtggagtc tgggggaggc ttggcacagc ctggagggtc cctgagactc    60
tcctgtgcag cctctggatt caccttcagt agtcatgaaa tgaactgggt ccgccaggct   120
ccagggaagg ggctggagtg ggtttcatac attagtcgta gtggtagaat cataaactac   180
gcagactctg tgaagggccg attcaccatc tccagagaca acgccaagaa ctcactgtat   240
ctgcaaatga acagcctgag agccgaggac acggctgttt attactgtgc gagagagaga   300
ggctcgtatt acgatatttt gactggttcc caggactacg gtatggacgt ctggggccaa   360
gggaccacgg tcaccgtctc ctca                                           384

<210> SEQ ID NO 290
<211> LENGTH: 128
<212> TYPE: PRT
<213> ORGANISM: Artificial Sequence
<220> FEATURE:
<223> OTHER INFORMATION: synthetic

<400> SEQUENCE: 290

Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Thr Phe Ser Ser His
            20                  25                  30

Glu Met Asn Trp Val Arg Gln Ala Pro Gly Lys Gly Leu Glu Trp Val
        35                  40                  45

Ser Tyr Ile Ser Arg Ser Gly Arg Ile Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Tyr Tyr Asp Ile Leu Thr Gly Ser Gln Asp
            100                 105                 110

Tyr Gly Met Asp Val Trp Gly Gln Gly Thr Thr Val Thr Val Ser Ser
        115                 120                 125

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct tcagtagtca tgaa                                              24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Ser Ser His Glu
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
attagtcgta gtggtagaat cata                                              24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Ser Arg Ser Gly Arg Ile Ile
1               5

<210> SEQ ID NO 295
<211> LENGTH: 63
<212> TYPE: DNA
<213> ORGANISM: Artificial Sequence
<220> FEATURE:
<223> OTHER INFORMATION: synthetic

<400> SEQUENCE: 295
gcgagagaga gaggctcgta ttacgatatt tgactggtt cccaggacta cggtatggac       60
gtc                                                                     63

<210> SEQ ID NO 296
<211> LENGTH: 21
<212> TYPE: PRT
<213> ORGANISM: Artificial Sequence
<220> FEATURE:
<223> OTHER INFORMATION: synthetic

<400> SEQUENCE: 296

Ala Arg Glu Arg Gly Ser Tyr Tyr Asp Ile Leu Thr Gly Ser Gln Asp
1               5                   10                  15

Tyr Gly Met Asp Val
            20

<210> SEQ ID NO 297
<211> LENGTH: 324
<212> TYPE: DNA
<213> ORGANISM: Artificial Sequence
<220> FEATURE:
<223> OTHER INFORMATION: synthetic

<400> SEQUENCE: 297

```
gacatccaga tgacccagtc tccatcctcc ctgtctgcat ctgtaggaga cagagtcacc    60
atcacttgcc gggcaagtca gaccattagc acctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 298
<211> LENGTH: 108
<212> TYPE: PRT
<213> ORGANISM: Artificial Sequence
<220> FEATURE:
<223> OTHER INFORMATION: synthetic

<400> SEQUENCE: 298

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299

```
cagaccatta gcacctat                                                  18
```

<210> SEQ ID NO 300
<211> LENGTH: 6
<212> TYPE: PRT
<213> ORGANISM: Artificial Sequence
<220> FEATURE:
<223> OTHER INFORMATION: synthetic

<400> SEQUENCE: 300

```
Gln Thr Ile Ser Thr Tyr
1               5
```

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 gctgcatcc					9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Ala Ala Ser
1

<210> SEQ ID NO 303
<211> LENGTH: 30
<212> TYPE: DNA
<213> ORGANISM: Artificial Sequence
<220> FEATURE:
<223> OTHER INFORMATION: synthetic

<400> SEQUENCE: 303
caacagagtt acagtacccc tccgatcacc					30

<210> SEQ ID NO 304
<211> LENGTH: 10
<212> TYPE: PRT
<213> ORGANISM: Artificial Sequence
<220> FEATURE:
<223> OTHER INFORMATION: synthetic

<400> SEQUENCE: 304

Gln Gln Ser Tyr Ser Thr Pro Pro Ile Thr
1               5                   10

<210> SEQ ID NO 305
<211> LENGTH: 381
<212> TYPE: DNA
<213> ORGANISM: Artificial Sequence
<220> FEATURE:
<223> OTHER INFORMATION: synthetic

<400> SEQUENCE: 305
gaggtgcagc tggtggagtc tgggggaggc ttggtacagc ctggagggtc cctgagactc					60 tcctgtgcag cctctggatt caccttcagt agttatgaaa tgaactgggt ccgccaggct					120 ccagggaagg ggctggagtg ggtttcatac attagtagta gtggtagtac caaatactac					180 gcagactctg tgaagggccg attcaccatc tccagagaca acgccaagaa ctcactgtat					240 ctgcaaatga acagcctgag agccgaggac acggctgttt attactgtgc gagaccttcg					300 agtataccag ctctgttacg gaaccagtac cactacggta tggacgtctg gggccaaggg					360 accacggtca ccgtctcctc a					381

<210> SEQ ID NO 306
<211> LENGTH: 127
<212> TYPE: PRT
<213> ORGANISM: Artificial Sequence
<220> FEATURE:
<223> OTHER INFORMATION: synthetic

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Glu Met Asn Trp Val Arg Gln Ala Pro Gly Lys Gly Leu Glu Trp Val
        35                  40                  45

Ser Tyr Ile Ser Ser Ser Gly Ser Thr Lys Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Pro Ser Ser Ile Pro Ala Leu Leu Arg Asn Gln Tyr His Tyr
            100                 105                 110

Gly Met Asp Val Trp Gly Gln Gly Thr Thr Val Thr Val Ser Ser
            115                 120                 125

<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307
ggattcacct tcagtagtta tgaa                                          24

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

Gly Phe Thr Phe Ser Ser Tyr Glu
 1               5

<210> SEQ ID NO 309
<211> LENGTH: 24
<212> TYPE: DNA
<213> ORGANISM: Artificial Sequence
<220> FEATURE:
<223> OTHER INFORMATION: synthetic

<400> SEQUENCE: 309
attagtagta gtggtagtac caaa                                          24

<210> SEQ ID NO 310
<211> LENGTH: 8
<212> TYPE: PRT
<213> ORGANISM: Artificial Sequence
<220> FEATURE:
<223> OTHER INFORMATION: synthetic

<400> SEQUENCE: 310

Ile Ser Ser Ser Gly Ser Thr Lys
 1               5

<210> SEQ ID NO 311
<211> LENGTH: 60
<212> TYPE: DNA
<213> ORGANISM: Artificial Sequence
<220> FEATURE:
<223> OTHER INFORMATION: synthetic

<400> SEQUENCE: 311
```

```
gcgagacctt cgagtatacc agctctgtta cggaaccagt accactacgg tatggacgtc    60
```

<210> SEQ ID NO 312
<211> LENGTH: 20
<212> TYPE: PRT
<213> ORGANISM: Artificial Sequence
<220> FEATURE:
<223> OTHER INFORMATION: synthetic

<400> SEQUENCE: 312

Ala Arg Pro Ser Ser Ile Pro Ala Leu Leu Arg Asn Gln Tyr His Tyr
1               5                   10                  15

Gly Met Asp Val
            20

<210> SEQ ID NO 313
<211> LENGTH: 2051
<212> TYPE: DNA
<213> ORGANISM: Ebola virus

<400> SEQUENCE: 313

```
gaattcgcca ccatgggcgt gaccggcatc ctgcagctgc cccgggacag attcaagcgg     60
accagcttct tcctgtgggt catcatcctg ttccagcgga ccttcagcat cccccctggg    120
gtgatccaca cagcaccct gcaggtgtcc gacgtggaca agctcgtgtg ccgggacaag    180
ctgagcagca ccaaccagct gagaagcgtg ggcctgaacc tggaaggcaa tggcgtggcc    240
accgatgtgc ctagcgccac caagagatgg ggcttcagat ccggcgtgcc ccccaaggtc    300
gtgaattatg aggccggcga gtgggccgag aactgctaca acctggaaat caagaagccc    360
gacggcagcg agtgcctgcc tgctgccct gatggcatca gaggcttccc ccggtgcaga    420
tacgtgcaca aggtgtccgg cacaggcccc tgcgctggcg atttcgcctt cacaaagag    480
ggcgcctttt tcctgtacga ccggctggcc tccaccgtga tctacagagg caccaccttt    540
gccgagggc tggtggcctt tctgatcctg cctcaggcca agaaggactt cttcagcagc    600
caccccctgc gcgagcctgt gaatgccaca gaggatccca gcagcggcta ctacagcacc    660
accatcagat accaggccac cggcttcggc accaacgaga cagagtacct gttcgaggtg    720
gacaacctga cctacgtgca gctggaaagc cggttcaccc ccagtttct gctgcagctg    780
aacgagacaa tctacgccag cggcaagcgg agcaacacca ccgcaagct gatctggaaa    840
gtgaacccg agatcgatac acaatcgga gagtgggcct ctgggagac aaagaagaac    900
ctgacccgga gatcagaag cgaggaactg agcttccccg ccgtgtccaa cggccccaag    960
aacatcagcg acagagccc cgccagaacc agcagcgacc ccgagacaaa caccaccaat   1020
gaggaccaca gatcatggc cagcgagaac agcagcgcca tggtgcaggt gcacagccag   1080
ggaagaaagg ccgctgtgtc ccacctgacc accctggcca aatctccac cagccctcag   1140
agcctgacca caaagcctgg ccccgacaac tccacccaca caccccccgt gtacaagctg   1200
gacatcagcg aggccacaca agtgggccag caccacagaa gggccgacaa cgatagcacc   1260
gccagcgata ccctccagc cacaactgct gccggacctc tgaaggccga aataccaac   1320
accagcaaga cgccgacag cctggatctg gccaccacca aagcccccca gaactactct   1380
gagacagccg gcaacaacaa cacccaccac caggataccg gcgaggaaag cgccagctct   1440
ggcaagctgg gactgatcac caacacaatc gccggcgtgg ccggcctgat tacggggggg   1500
agaagaacca cacgggaagt gatcgtgaac gcccagccca gtgcaaccc caacctgcac   1560
tactggacca cccaggatga gggcgctgct atcggactgg cctggatccc ttactttggc   1620
```

```
cctgccgccg agggcatcta caccgaggga ctgatgcaca accaggacgg cctgatctgc    1680
ggactgaggc agctggccaa cgaaaccaca caggctctgc agctgttcct gagagccacc    1740
accgagctga ggaccttctc catcctgaac agaaaggcta tcgacttcct gctgcagcgc    1800
tggggcggca cctgtcacat tctgggccct gactgctgca tcgagcccca cgactggacc    1860
aagaatatca ccgacaagat cgaccagatc atccacgact tgtggacaa gaccctgccc    1920 gaccagggcg acaatgacaa ctggtggaca ggctggcggc agtggattcc tgccggcatt    1980
ggagtgaccg gcgtgatcat tgccgtgatc gccctgttct gcatctgcaa gttcgtgttc    2040
tgagcggccg c                                                         2051
```

<210> SEQ ID NO 314
<211> LENGTH: 676
<212> TYPE: PRT
<213> ORGANISM: Ebola virus

<400> SEQUENCE: 314

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285
```

| | | | | | | | | | | | | | | |
|---|---|---|---|---|---|---|---|---|---|---|---|---|---|---|
|Ala|Phe|Trp|Glu|Thr|Lys|Lys|Asn|Leu|Thr|Arg|Lys|Ile|Arg|Ser|Glu|
| |290| | | |295| | | |300| | | | | |

Glu Leu Ser Phe Thr Ala Val Ser Asn Gly Pro Lys Asn Ile Ser Gly
305             310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Ala Ala Gly Pro Leu Lys Ala
            420                 425                 430

Glu Asn Thr Asn Thr Ser Lys Ser Ala Asp Ser Leu Asp Leu Ala Thr
                435                 440                 445

Thr Thr Ser Pro Gln Asn Tyr Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 315
<211> LENGTH: 676
<212> TYPE: PRT

<213> ORGANISM: Ebola virus

<400> SEQUENCE: 315

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400
```

Ala Thr Gln Val Gly Gln His His Arg Arg Ala Asp Asn Asp Ser Thr
                405                 410                 415

Ala Ser Asp Thr Pro Pro Ala Thr Ala Ala Gly Pro Leu Lys Ala
        420                 425                 430

Glu Asn Thr Asn Thr Ser Lys Ser Ala Asp Ser Leu Asp Leu Ala Thr
                435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Thr
        530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
        610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
        675

<210> SEQ ID NO 316
<211> LENGTH: 364
<212> TYPE: PRT
<213> ORGANISM: Ebola virus

<400> SEQUENCE: 316

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

```
Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Thr Ser Leu Glu Lys Phe Ala Val Lys
            290                 295                 300

Ser Cys Leu Ser Gln Leu Tyr Gln Thr Asp Pro Lys Thr Ser Val Val
305                 310                 315                 320

Arg Val Arg Arg Glu Leu Leu Pro Thr Gln Arg Pro Thr Gln Gln Met
                325                 330                 335

Lys Thr Thr Lys Ser Trp Leu Gln Lys Ile Pro Leu Gln Trp Phe Lys
            340                 345                 350

Cys Thr Val Lys Glu Gly Lys Leu Gln Cys Arg Ile
        355                 360

<210> SEQ ID NO 317
<211> LENGTH: 360
<212> TYPE: PRT
<213> ORGANISM: Artificial Sequence
<220> FEATURE:
<223> OTHER INFORMATION: aa 1-332: Zaire_Ebola_GP aa 33 through 364 of
      AHX24650
      aa 333-360: myc-myc-hexahistidine tag

<400> SEQUENCE: 317

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80
```

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
            180                 185                 190

Phe Gly Thr Asn Glu Thr Glu Tyr Leu Phe Glu Val Asp Asn Leu Thr
        195                 200                 205

Tyr Val Gln Leu Glu Ser Arg Phe Thr Pro Gln Phe Leu Leu Gln Leu
    210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Thr Ser Leu Glu Lys Phe Ala Val Lys
            260                 265                 270

Ser Cys Leu Ser Gln Leu Tyr Gln Thr Asp Pro Lys Thr Ser Val Val
        275                 280                 285

Arg Val Arg Arg Glu Leu Leu Pro Thr Gln Arg Pro Thr Gln Gln Met
    290                 295                 300

Lys Thr Thr Lys Ser Trp Leu Gln Lys Ile Pro Leu Gln Trp Phe Lys
305                 310                 315                 320

Cys Thr Val Lys Glu Gly Lys Leu Gln Cys Arg Ile Glu Gln Lys Leu
                325                 330                 335

Ile Ser Glu Glu Asp Leu Gly Gly Glu Gln Lys Leu Ile Ser Glu Glu
            340                 345                 350

Asp Leu His His His His His His
        355                 360

<210> SEQ ID NO 318
<211> LENGTH: 628
<212> TYPE: PRT
<213> ORGANISM: Artificial Sequence
<220> FEATURE:
<223> OTHER INFORMATION: aa 1-618: Zaire ebolavirus (strain
      H.sapiens-wt/GIN/2014/Kissidougou-C15) GP (aa 33
      through 650  (AHX24649.1))
      aa 619-628: decahistidine tag

<400> SEQUENCE: 318

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

```
Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Ala Pro Asp Gly
                 85                  90                  95

Ile Arg Gly Phe Pro Arg Cys Arg Tyr Val His Lys Val Ser Gly Thr
                100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
        130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
        210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Val Val Ser Asn Gly Ala Lys Asn Ile Ser Gly
            275                 280                 285

Gln Ser Pro Ala Arg Thr Ser Ser Asp Pro Gly Thr Asn Thr Thr Thr
        290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
            355                 360                 365

Ala Thr Gln Val Glu Gln His His Arg Arg Thr Asp Asn Asp Ser Thr
        370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
            435                 440                 445

Leu Ile Thr Asn Thr Ile Ala Gly Val Ala Gly Leu Ile Thr Gly Gly
        450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
```

-continued

```
                         485                 490                 495
Leu Ala Trp Ile Pro Tyr Phe Gly Pro Ala Ala Glu Gly Ile Tyr Ile
            500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
        530                 535                 540

Thr Glu Leu Arg Thr Phe Ser Ile Leu Asn Arg Lys Ala Ile Asp Phe
545                 550                 555                 560

Leu Leu Gln Arg Trp Gly Gly Thr Cys His Ile Leu Gly Pro Asp Cys
                565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly Trp Arg Gln His His His His His
        610                 615                 620

His His His His
625
```

HUMAN ANTIBODIES TO EBOLA VIRUS GLYCOPROTEIN

CROSS-REFERENCE TO RELATED APPLICATIONS

This application is a continuation of U.S. patent application Ser. No. 16/663,261, filed Oct. 24, 2019, which is a continuation of U.S. patent application Ser. No. 16/108,096, filed Aug. 22, 2018, now U.S. Pat. No. 10,501,526, which is a continuation of U.S. patent application Ser. No. 15/688,474, filed Aug. 28, 2017, now U.S. Pat. No. 10,081,670, which is a divisional of U.S. patent application Ser. No. 15/005,334, filed Jan. 25, 2016, now U.S. Pat. No. 9,771,414, which claims the benefit under 35 U.S.C § 119(e) of U.S. Provisional Application Ser. No. 62/107,581, filed Jan. 26, 2015; 62/161,356, filed May 14, 2015; and 62/245,703, filed Oct. 23, 2015, all of which are herein specifically incorporated by reference in their entireties.

FIELD OF THE INVENTION

The present invention relates to antibodies that bind to Ebola virus glycoprotein, pharmaceutical compositions comprising these antibodies and methods of use thereof.

BACKGROUND

Ebola virus (EBOV) and related filoviruses cause severe viral hemorrhagic fever in humans and non-human primates, with a fatality rate of up to about 90% in human outbreaks. (Murin, C. D. et al., (2014), Proc Natl Acad Sci USA, 111(48):17182-17187). The immune mechanisms that mediate protection are under investigation, but to date, no treatments have been approved for human use.

The Ebola virus glycoprotein (GP) is the only protein present on the surface of the virus and on infected cells. It is presumed to be responsible for binding and fusion of the virus with host cells. The GP exists in several forms. These GPs are encoded in two open reading frames. The unedited GP mRNA produces a non-structural secreted, soluble GP (sGP) that is synthesized early in the course of infection (Volchkova, et al. (1995), Virology 214:421-430; Volchkova, V A et al., (1998), Virology 250:408-414; Sanchez, et al. (1996), Proc Natl Acad Sci USA, 93:3602-3607; Sanchez, et al. (1999) J. Infect. Dis. 179 (suppl. 1, S164)). The sGP forms dimers (Volchkova, et al. (1995), Virology 214:421-430; Falzarano, D. et al., Chembiochem (2006), 7:1605-1611) and high amounts are detected in the blood of patients and experimentally infected animals (Sanchez, et al. (1996), Proc Natl Acad Sci USA, 93:3602-3607; Dolnik, O. et al., (2004), EMBO J 23:2175-2184).

Later in infection, an edited mRNA is generated, acquiring coding capacity from a second open reading frame. This edited mRNA encodes a form of GP that contains a transmembrane (TM) domain that permits this form of GP to be tethered to the plasma membrane of the cell, and incorporated into virions where it serves as the functional host cell receptor-binding protein/fusion protein. During biosynthesis of this form of GP, the protein is proteolytically processed into two products that are held together by disulfide bonds. The amino terminal product is referred to as GP1 (140 kDa) and the carboxy-terminal cleavage product is referred to as GP2 (26 kDa) (Sanchez, et al. (1998), J. Virol. 72:6442-6447).

The Ebola virus GP (EBOV GP) may be a target for protective antibodies, but the role of antibodies in disease resistance has been controversial. Negligible serum titers of neutralizing antibodies in convalescent patients together with inconsistent results in achieving protection with experimental transfer of immune sera to animals has resulted in speculation as to the role of neutralizing antibodies in recovery from infection (Peters, C J and LeDuc, J W, (1999), J. Infect. Dis. 179 Suppl 1; Mikhailov, V V, (1994), Vopr. Virusol. 39:82; Xu, L. et al., (1998), Nature Med. 4: 37). However, in the more recent outbreak of Ebola virus, a few patients who contracted the disease and who were treated with a cocktail of monoclonal antibodies (ZMapp) specific for the viral GP recovered from the disease. Moreover, other patients that were treated with the serum from these patients and from other patients who survived after acquiring the infection, also had positive outcomes.

Several antibodies that bind Ebola virus GP have been described (See for example, U.S. Pat. Nos. 6,630,144, 6,875,433, 7,335,356 and 8,513,391. See also EP1539238, EP2350270 and EP8513391).

While technological advances have improved the ability to produce improved Ebola virus antigen(s) vaccine compositions, there remains a need to provide additional sources of protection to address emerging strains of Ebola virus. Several candidate therapeutics against Ebola virus are currently under evaluation, including post exposure vaccines (Feldman, H, et al. (2007), PLos Pathog 3(1):e2), small molecule inhibitors (Cote, M. et al. (2011), Nature, 477 (7364):344-348; Johansen, L M, et al. (2013), Sci Transl Med 5(190):190ra179; Warren, T K, et al., (2014), Nature, 508(7496):402-405), siRNA-based therapeutics (Geisbert, T W, et al., (2006), J. Infect Dis. 193(12):1650-1657; Geisbert, T W et al., (2010), Lancet 375(9729):1896-1905), and monoclonal antibodies (Saphire, E O, (2013), Immunotherapy 5(11):1221-1233; Wong, G. et al. (2014), Trends Microbiol. 22(8):456-463; Qiu, X et al., (2014), Hum. Vaccin. Immunother. 10(4):964-967). Passive administration of antibodies to non-human primates has proven to be efficacious (Dye, J M., et al., (2012), Proc Natl Acad Sci USA 109(13):5034-5039). More recently, a cocktail of three antibodies (ZMapp) is currently being produced in tobacco plants and is in development for human use (Qiu, X. et al., (2014), Nature 514(7520):47-53).

While the idea of a vaccine composition comprising the antigen of interest (e.g. the GP) to generate neutralizing antibodies in a patient is generally thought to be a good approach, it may not be advantageous to use in patients who have already been exposed to the virus, since it would take several weeks for the body to respond to the vaccine composition. By that point in time, the patient may have already succumbed to the viral infection, depending on the level of care and palliative therapy available. In these patients, or in any patient who is not able to mount an effective antibody response, it may be more beneficial to provide a composition already containing protective antibodies that may target epitopes common to a particular strain of EBOV, or to a variety of strains.

Accordingly, there is still a need in the art to identify new antibodies, which can be used to prevent or treat an Ebola virus infection.

BRIEF SUMMARY OF THE INVENTION

The present invention provides antibodies and antigen-binding fragments thereof that bind Ebola virus (EBOV) glycoprotein (GP). The antibodies of the present invention are useful for inhibiting or neutralizing the activity of Ebola virus. In some embodiments, the antibodies are useful for blocking attachment of the Ebola virus to the host cell and/or for preventing the entry of the Ebola virus into host cells. In some embodiments, the antibodies function by inhibiting the cell-to-cell transmission of the virus, or by killing Ebola virus-infected cells, reducing production of pathogenic virus. In certain embodiments, the antibodies are useful in preventing, treating or ameliorating at least one symptom of Ebola virus infection in a subject. In certain embodiments, the antibodies may be administered prophylactically or therapeutically to a subject having, or at risk of acquiring, an Ebola virus infection. In certain embodiments, compositions containing at least one antibody of the invention may be administered to a subject for whom a vaccine is contraindicated, or for whom a vaccine is less efficacious, for example, an elderly patient, a very young patient, a patient who may be allergic to any one or more components of a vaccine, or an immunocompromised patient who may be non-responsive to the immunogens in a vaccine. In certain embodiments, compositions containing at least one antibody of the invention may be administered to medical staff, hospitalized patients or nursing home residents or other high-risk patients during an Ebola virus outbreak. In certain embodiments, compositions containing at least one antibody of the invention may be administered as a first line treatment to patients who have already been exposed to an Ebola virus.

The antibodies of the invention can be full-length (for example, an IgG1 or IgG4 antibody) or may comprise only an antigen-binding portion (for example, a Fab, F(ab')2 or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to the EBOV GP.

In one embodiment, the present invention provides an isolated recombinant antibody or antigen-binding fragment thereof that specifically binds to Ebola virus (EBOV) and/or an Ebola virus glycoprotein (EBOV-GP), wherein the antibody has one or more of the following characteristics:
 (a) comprises three heavy chain complementarity determining regions (CDRs) (HCDR1, HCDR2 and HCDR3) contained within any one of the heavy chain variable region (HCVR) sequences selected from the group consisting of SEQ ID NOs: 18, 66, 146, 2, 34, 50, 82, 98, 114, 130, 162, 178, 194, 210, 226, 242, 258, 274, 290, and 306; and three light chain CDRs (LCDR1, LCDR2 and LCDR3) contained within any one of the light chain variable region (LCVR) sequences selected from the group consisting of SEQ ID NOs: 26, 74, 154, 10, 42, 58, 90, 106, 122, 138, 170, 186, 202, 218, 234, 250, 266, 282, and 298;
 (b) is a fully human monoclonal antibody;
 (c) binds to EBOV, or a virus like particle (VLP) expressing an EBOV-GP with a dissociation constant ($K_D$) of less than $10^{-7}$M, as measured in a surface plasmon resonance assay;
 (d) demonstrates at least a 3 fold increase in dissociative half-life (t½) at pH 5 or pH 6 relative to pH 7.4;
 (e) demonstrates neutralization of Zaire Ebola virus with an 1050 ranging from about $10^{-11}$ M to about $10^{-9}$M;
 (f) demonstrates binding to cells expressing the EBOV-GP triggering antibody-dependent cellular cytotoxicity;
 (g) cross reacts with one or more strains of EBOV selected from the group consisting of Zaire.2014, Zaire.1995, Sudan, Bundibugyo and Cote d'Ivoire;
 (h) binds to soluble GP (sGP);
 (i) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

In one embodiment, the present invention provides an isolated recombinant antibody or antigen-binding fragment thereof that specifically binds to EBOV and/or an Ebola virus glycoprotein (EBOV GP), wherein the antibody has two or more of the following characteristics:
 (a) is a fully human monoclonal antibody;
 (b) binds to EBOV, or a virus like particle (VLP) expressing an EBOV GP with a dissociation constant ($K_D$) of less than $10^{-7}$M, as measured in a surface plasmon resonance assay;
 (c) demonstrates at least a 3 fold increase in dissociative half-life (t½) at pH 5 or pH 6 relative to pH 7.4;
 (d) demonstrates neutralization of Zaire Ebola virus with an $IC_{50}$ ranging from about $10^{-11}$ M to about $10^{-9}$M;
 (e) demonstrates binding to cells expressing the EBOV GP triggering antibody-dependent cellular cytotoxicity;
 (f) cross reacts with one or more strains of EBOV selected from the group consisting of Zaire.2014, Zaire.1995, Sudan, Bundibugyo and Cote d'Ivoire;
 (g) binds to soluble GP (sGP);
 (h) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

Exemplary anti-Ebola virus GP antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-Ebola virus GP antibodies. Table 2 sets forth the nucleic acid sequence identifiers of the HCVRs, LCVRs, HCDR1, HCDR2 HCDR3, LCDR1, LCDR2 and LCDR3 of the exemplary anti-Ebola virus GP antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-Ebola virus GP antibodies listed in Table 1.

In one embodiment, the isolated antibody or antigen-binding fragment comprises a HCVR/LCVR amino acid sequence pair selected from the group consisting of SEQ ID NOs: 18/26, 66/74, 146/154, 2/10, 34/42, 50/58, 82/90, 98/106, 114/122, 130/138, 162/170, 178/186, 194/202, 210/218, 226/234, 242/250, 258/266, 274/282, 290/298 and 306/282.

In one embodiment, the isolated antibody or antigen-binding fragment comprises:

(a) a HCDR1 domain having an amino acid sequence selected from the group consisting of SEQ ID NOs: 20, 68, 148, 4, 36, 52, 84, 100, 116, 132, 164, 180, 196, 212, 228, 244, 260, 276, 292 and 308;

(b) a HCDR2 domain having an amino acid sequence selected from the group consisting of SEQ ID NOs: 22, 70, 150, 6, 38, 54, 86, 102, 118, 134, 166, 182, 198, 214, 230, 246, 262, 278, 294 and 310;

(c) a HCDR3 domain having an amino acid sequence selected from the group consisting of SEQ ID NOs: 24, 72, 152, 8, 40, 56, 88, 104, 120, 136, 168, 184, 200, 216, 232, 248, 264, 280, 296 and 312;

(d) a LCDR1 domain having an amino acid sequence selected from the group consisting of SEQ ID NOs: 28, 76, 156, 12, 44, 60, 92, 108, 124, 140, 172, 188, 204, 220, 236, 252, 268, 284 and 300;

(e) a LCDR2 domain having an amino acid sequence selected from the group consisting of SEQ ID NOs: 30, 78, 158, 14, 46, 62, 94, 110, 126, 142, 174, 190, 206, 222, 238, 254, 270, 286 and 302;

(f) a LCDR3 domain having an amino acid sequence selected from the group consisting of SEQ ID NOs: 32, 80, 160, 16, 48, 64, 96, 112, 128, 144, 176, 192, 208, 224, 240, 256, 272, 288 and 304.

In certain embodiments, the HCVR/LCVR amino acid sequence pair is selected from the group consisting of SEQ ID NOs: 18/26 (H1H17139P), 66/74 (H1H17161P) and 146/154 (H1H17203P).

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-Ebola virus GP antibodies listed in Table 1. In certain embodiments, the HCDR3/LCDR3 amino acid sequence pair is selected from the group consisting of SEQ ID NOs: 24/32 (e.g., H1H17139P), 72/80 (e.g., H1H17161P), and 152/160 (e.g., H1H17203P).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-Ebola virus GP antibodies listed in Table 1. In certain embodiments, the HCDR1-HCDR2-HCDR3-LCDR1-LCDR2-LCDR3 amino acid sequence set is selected from the group consisting of SEQ ID NOs: 20-22-24-28-30-32 (e.g., H1H17139P), 68-70-72-76-78-80 (e.g., H1H17161P); and 148-150-152-156-158-160 (e.g., H1H17203P).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-Ebola virus GP antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 18/26 (e.g., H1H17139P), 66/74 (e.g., H1H17161P); and 146/154 (e.g., H1H17203P). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-Ebola virus antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides for antibodies and antigen-binding fragments thereof that compete for specific binding to Ebola virus with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to Ebola virus with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block Ebola virus attachment to, and/or entry into a host cell.

In certain embodiments, the antibodies or antigen-binding fragments of the present invention are bispecific comprising a first binding specificity to a first epitope in the Ebola virus and a second binding specificity to a second epitope in the Ebola virus, wherein the first and second epitopes are distinct and non-overlapping. In certain embodiments the bispecific may comprise a first arm that binds to an epitope in the viral glycoprotein and a second arm that binds to an epitope in a different viral antigen.

In a second aspect, the present invention provides nucleic acid molecules encoding anti-Ebola virus antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-Ebola virus GP antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-Ebola virus GP antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-Ebola virus GP antibody listed in Table 1.

The present invention provides nucleic acid molecules encoding any of the heavy chain amino acid sequences listed in Table 1. The present invention also provides nucleic acid molecules encoding any of the light chain amino acid sequences listed in Table 1.

In a related aspect, the present invention provides recombinant expression vectors capable of expressing a polypeptide comprising a heavy or light chain variable region of an anti-Ebola virus GP antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the invention provides a pharmaceutical composition comprising one or more isolated monoclonal antibodies or antigen-binding fragments thereof which specifically bind to Ebola virus GP and a pharmaceutically acceptable carrier or diluent. The one or more isolated antibodies comprise an HCVR/LCVR amino acid sequence pair selected from the group consisting of the HCVR and LCVR sequences listed in Table 1. In one embodiment, the HCVR/LCVR amino acid sequence pair is selected from the group consisting of SEQ ID NOs: 18/26, 66/74, 146/154, 2/10, 34/42, 50/58, 82/90, 98/106, 114/122, 130/138, 162/170, 178/186, 194/202, 210/218, 226/234, 242/250, 258/266, 274/282, 290/298 and 306/282. In one embodiment, the HCVR/LCVR amino acid sequence pair is selected from the group consisting of SEQ ID NOs:18/26, 66/74 and 146/154.

In a related aspect, the invention features a composition, which is a combination of at least two antibodies of the invention and a pharmaceutically acceptable carrier or diluent.

In a related aspect, the invention features a composition, which is a combination/cocktail of at least three antibodies of the invention and a pharmaceutically acceptable carrier or diluent.

In one embodiment, the pharmaceutical composition comprises (a) a first anti-Ebola virus antibody, comprising an HCVR/LCVR amino acid sequence pair as described in Table 1, or an antigen-binding fragment thereof; (b) a second anti-Ebola virus antibody, comprising an HCVR/LCVR amino acid sequence pair as described in Table 1, or antigen-binding fragment thereof; and (c) a third anti-Ebola virus antibody, comprising an HCVR/LCVR amino acid sequence pair as described in Table 1, or antigen-binding fragment thereof, wherein the first antibody binds to, or interacts with, a first epitope on Ebola virus GP and the second and/or third antibody binds to, or interact(s) with a different epitope on Ebola virus GP, and (d) a pharmaceutically acceptable carrier or diluent.

In another related aspect, the invention features a composition, which is a combination of an anti-Ebola virus GP antibody and a second therapeutic agent.

In one embodiment, the second therapeutic agent is any agent that is advantageously combined with an anti-Ebola virus GP antibody. Exemplary agents that may be advantageously combined with an anti-Ebola virus antibody include, without limitation, other agents that bind and/or inhibit Ebola virus activity (including other antibodies or antigen-binding fragments thereof, etc.) and/or agents, which do not directly bind Ebola virus but nonetheless inhibit viral activity including infectivity of host cells.

In certain embodiments, the invention provides for a pharmaceutical composition comprising: (a) a first anti-Ebola virus antibody comprising an HCVR/LCVR amino acid sequence pair as described in Table 1, or antigen-binding fragment thereof; (b) a second anti-Ebola virus antibody comprising an HCVR/LCVR amino acid sequence pair as described in Table 1, or antigen-binding fragment thereof, wherein the first antibody binds to a first epitope on Ebola virus GP and the second antibody binds to a second epitope on Ebola virus GP wherein the first and second epitopes are distinct and non-overlapping; and (c) a pharmaceutically acceptable carrier or diluent.

In certain embodiments, the invention provides for a pharmaceutical composition comprising: (a) a first anti-Ebola virus antibody or antigen-binding fragment thereof; (b) a second anti-Ebola virus antibody or antigen-binding fragment thereof, wherein the first antibody does not cross-compete with the second antibody for binding to Ebola virus; and (c) a pharmaceutically acceptable carrier or diluent.

In certain embodiments, the invention provides for a pharmaceutical composition comprising: (a) a first anti-Ebola virus antibody or antigen-binding fragment thereof; (b) a second anti-Ebola virus antibody or antigen-binding fragment thereof, which interacts with a different Ebola virus antigen, wherein the first antibody binds to an epitope on Ebola virus GP and the second antibody binds to an epitope on a different Ebola virus antigen; and (c) a pharmaceutically acceptable carrier or diluent.

In certain embodiments, the invention provides for a pharmaceutical composition comprising: (a) a first anti-Ebola virus antibody or antigen-binding fragment thereof; (b) a second anti-Ebola virus antibody or antigen-binding fragment thereof; (c) a third anti-Ebola virus antibody or antigen-binding fragment thereof, wherein the first antibody binds to a first epitope on Ebola virus GP and the second and/or third antibody binds to a different epitope on Ebola virus GP wherein the first, second and third epitopes are distinct and non-overlapping; and (d) a pharmaceutically acceptable carrier or diluent.

In certain embodiments, the invention provides for a pharmaceutical composition comprising: (a) a first anti-Ebola virus antibody or antigen-binding fragment thereof; (b) a second anti-Ebola virus antibody or antigen-binding fragment thereof; (c) a third anti-Ebola virus antibody or an antigen-binding fragment thereof, wherein the first antibody may or may not cross-compete with the second, and/or third antibody for binding to Ebola virus; and (d) a pharmaceutically acceptable carrier or diluent.

In certain embodiments, the invention provides for a pharmaceutical composition comprising: (a) a first anti-Ebola virus antibody or antigen-binding fragment thereof; (b) a second and/or third anti-Ebola virus antibody or antigen-binding fragment thereof, which interacts with a different Ebola virus antigen, wherein the first antibody binds to an epitope on Ebola virus and the second and/or third antibody binds to an epitope on a different Ebola virus antigen; and (c) a pharmaceutically acceptable carrier or diluent.

In one embodiment, the pharmaceutical composition comprises a first anti-Ebola virus antibody or an antigen-binding fragment thereof that binds to, or interacts with one epitope on one strain of Ebola virus and the second and/or third anti-Ebola virus antibody or an antigen-binding fragment thereof that binds to, or interacts with a second and/or a third epitope on the same strain or on a different strain of Ebola virus. The Ebola virus strains that interact with an antibody of the invention may be selected from the group consisting of the Zaire.2014, Zaire.1995, Sudan, Bundibugyo, and Cote d'lvoire strains, or variants thereof.

In a related aspect, the invention provides a pharmaceutical composition comprising a first isolated monoclonal antibody or an antigen-binding fragment thereof that binds specifically to Ebola virus GP, wherein the first isolated monoclonal antibody or an antigen-binding fragment thereof comprises an HCDR1 amino acid sequence of SEQ ID NO: 20; an HCDR2 amino acid sequence of SEQ ID NO: 22; an HCDR3 amino acid sequence of SEQ ID NO: 24; an LCDR1 amino acid sequence of SEQ ID NO: 28; an LCDR2 amino acid sequence of SEQ ID NO: 30 and an LCDR3 amino acid sequence of SEQ ID NO: 32, and a pharmaceutically acceptable carrier or diluent. The pharmaceutical composition may further comprise a second isolated monoclonal antibody or an antigen-binding fragment thereof that binds specifically to Ebola virus GP, wherein the second isolated monoclonal antibody or an antigen-binding fragment thereof comprises an HCDR1 amino acid sequence of SEQ ID NO: 68; an HCDR2 amino acid sequence of SEQ ID NO: 70; an HCDR3 amino acid sequence of SEQ ID NO: 72; an LCDR1 amino acid sequence of SEQ ID NO: 76; an LCDR2 amino acid sequence of SEQ ID NO: 78 and an LCDR3 amino acid sequence of SEQ ID NO: 80. The pharmaceutical composition may further comprise a third isolated monoclonal antibody or an antigen-binding fragment thereof that binds specifically to Ebola virus GP, wherein the third isolated monoclonal antibody or an antigen-binding fragment thereof comprises an HCDR1 amino acid sequence of SEQ ID NO: 148; an HCDR2 amino acid sequence of SEQ ID NO: 150; an HCDR3 amino acid sequence of SEQ ID NO: 152; an LCDR1 amino acid sequence of SEQ ID NO: 156; an LCDR2 amino acid sequence of SEQ ID NO: 158 and an LCDR3 amino acid sequence of SEQ ID NO: 160.

In certain embodiments, each antibody may be formulated as a separate formulation and if it is determined that more than one antibody is needed to achieve maximal therapeutic efficacy, each of the antibody formulations may be co-administered (concurrently, or sequentially), as needed. Alternatively, the antibody cocktail may be co-formulated.

In certain embodiments, when two or more antibodies are combined together in one pharmaceutical composition, they may or may not bind the same or overlapping epitopes on the Ebola virus protein. Additional combination therapies and co-formulations involving the anti-Ebola virus antibodies of the present invention are disclosed elsewhere herein.

In a fourth aspect, the invention provides therapeutic methods for treating a disease or disorder associated with Ebola virus (such as viral infection in a subject), or at least one symptom associated with the viral infection, or the frequency or severity of at least one symptom associated with EBOV infection, using an anti-Ebola virus GP antibody or antigen-binding portion of an antibody of the invention, or a cocktail of at least two or more antibodies of the invention, wherein the therapeutic methods comprise administering a therapeutically effective amount of at least two or more antibodies or antigen-binding fragments of the invention to the subject in need thereof. In one embodiment, the methods comprise administering a combination (cocktail) of at least three antibodies of the invention. In one embodiment, the antibody cocktail comprises three anti-EBOV antibodies having the amino acid sequence pairs as set forth in SEQ ID NOs: 18/26, 66/74 and 146/154. The disorder treated is any disease or condition, which is improved, ameliorated, inhibited or prevented by inhibition of Ebola virus activity. In certain embodiments, the invention provides methods to prevent, treat or ameliorate at least one symptom of Ebola virus infection, the method comprising administering a therapeutically effective amount of at least one or more anti-Ebola virus GP antibodies or antigen-binding fragments thereof of the invention to a subject in need thereof.

In a related aspect, the invention provides a method of neutralizing infectious EBOV, the method comprising exposing a cell infected with EBOV to a composition comprising one or more anti-EBOV antibodies or antigen-binding fragments thereof, wherein the exposing results in enhanced protection of the cell from virus infection, or from cell death. In certain embodiments, the exposing may be in vitro or in vivo. In one embodiment, the methods comprise administering one or more antibodies of the invention. In one embodiment, the methods comprise administering a combination (cocktail) of at least three antibodies of the invention. In one embodiment, the antibody cocktail comprises three anti-EBOV antibodies having the amino acid sequence pairs as set forth in SEQ ID NOs: 18/26, 66/74 and 146/154.

In some embodiments, the present invention provides methods to ameliorate or reduce the severity, duration, or frequency of occurrence, of at least one symptom of Ebola virus infection in a subject by administering one or more anti-Ebola virus GP antibodies of the invention, wherein the at least one symptom is selected from the group consisting of fever, headache, fatigue, loss of appetite, myalgia, diarrhea, vomiting, abdominal pain, dehydration and unexplained bleeding.

In certain embodiments, the invention provides methods to decrease viral load in a subject, the methods comprising administering to the subject an effective amount of one or more antibodies or fragments thereof of the invention that binds Ebola virus GP and blocks Ebola virus binding and/or entry into the host cell.

In a related aspect, the invention provides a method of increasing the survival, or the likelihood of survival of a subject suffering from infection with EBOV, or a subject exposed to EBOV, or at risk for exposure to, or for acquiring EBOV, the method comprising administering at least one antibody or antigen-binding fragment of the invention, or a pharmaceutical composition comprising at least one antibody of the invention to a subject in need thereof.

In one embodiment, the invention provides a method of increasing the survival, or the likelihood of survival of a subject suffering from infection with EBOV, or a subject exposed to EBOV, or at risk for exposure to, or for acquiring EBOV, the method comprising administering an antibody cocktail comprising a mixture of at least two anti-EBOV antibodies of the invention. In one embodiment, the method comprises administering an antibody cocktail comprising a mixture of at least three anti-EBOV antibodies of the invention. In one embodiment, the antibody cocktail to be administered comprises a mixture of at least three anti-EBOV antibodies of the invention, wherein the at least three antibodies comprise HCVR/LCVR amino acid sequence pairs as set forth in SEQ ID NOs: 18/26, 66/74 and 146/154.

In one embodiment, the subject in need thereof is a subject at risk for exposure to, or for acquiring an Ebola virus infection, wherein the subject is selected from the group consisting of an immunocompromised individual, a healthcare worker, a person who is suspected of having been exposed to a person harboring the Ebola virus, a person who comes into physical contact or close physical proximity with an infected individual, a hospital employee, a pharmaceutical researcher, maintenance personnel responsible for cleaning a hospital facility or institution where an Ebola patient has been treated, individuals who have visited or are planning to visit an area or country known to have or suspected to have an outbreak of Ebola virus and a frequent flyer.

In one embodiment, the subject in need thereof may be administered at least one anti-EBOV antibody of the invention or an antigen-binding fragment thereof, or a pharmaceutical composition comprising at least one antibody or antigen-binding fragment thereof of the invention in combination with a second therapeutic agent. The second therapeutic agent may be selected from the group consisting of an anti-viral drug, an anti-inflammatory drug (such as corticosteroids, and non-steroidal anti-inflammatory drugs), a different antibody to EBOV, a vaccine for EBOV, TKM Ebola (small interfering RNAs that target viral RNA polymerase) brincidofovir (CMX-001), favipiravir (T-705), BCX-4430, AVI-7537 (antisense phosphorodiamidate morpholino oligomers that target Ebola virus VP24 gene) and interferons.

In one embodiment, the pharmaceutical composition may be administered subcutaneously, intravenously, intradermally, intramuscularly, intranasally, or orally.

In a related embodiment, enhanced protection may be observed in a mammal exposed to, or infected with EBOV when the mammal is treated with a pharmaceutical composition comprising an antibody cocktail, which comprises at least three antibodies of the invention.

In one embodiment, the enhanced protection observed may be measured by a decrease in the severity or frequency of at least one symptom associated with EBOV infection, by a decrease in viral load, or by an increase in survival of a mammal infected with EBOV. The at least one symptom may be selected from the group consisting of fever, headache, fatigue, loss of appetite, myalgia, diarrhea, vomiting, abdominal pain, dehydration and unexplained bleeding.

The enhanced protection may be observed when the antibody is used alone, or when it is used in combination with one or more additional therapeutic agents or anti-EBOV treatment modalities.

The one or more additional therapeutic agents may be selected from the group consisting of an anti-viral drug, an anti-inflammatory drug (such as corticosteroids, and non-steroidal anti-inflammatory drugs), a different antibody to Ebola virus, a vaccine for Ebola virus, TKM Ebola (small interfering RNAs that target viral RNA polymerase) brincidofovir (CMX-001), favipiravir (T-705), BCX-4430, AVI-7537 (antisense phosphorodiamidate morpholino oligomers that target Ebola virus VP24 gene) and interferons.

In one embodiment, the one or more additional therapeutic agents comprise one or more anti-EBOV antibodies.

In one embodiment, the one or more anti-EBOV antibodies comprise a heavy chain variable region (HCVR) and a light chain variable region (LCVR) amino acid sequence selected from the group consisting of any of the HCVR and LCVR amino acid sequences of Table 1.

In a related embodiment, the one or more anti-EBOV antibodies comprise a heavy chain variable region (HCVR) and a light chain variable region (LCVR) amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298 and 306/282.

In another related embodiment, the one or more anti-EBOV antibodies comprise a heavy chain variable region (HCVR) and a light chain variable region (LCVR) amino acid sequence pair selected from the group consisting of SEQ ID NOs: 18/26, 66/74 and 146/154.

In certain embodiments, the one or more antibodies or antigen-binding fragments thereof may be administered prophylactically or therapeutically to a subject having, or at risk of having, or pre-disposed to developing an Ebola virus infection. The subjects at risk include, but are not limited to, an immunocompromised person, for example, a person who is immunocompromised because of autoimmune disease, or those persons receiving immunosuppressive therapy (for example, following organ transplant), or those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Other subjects at risk for acquiring an Ebola virus infection include healthcare workers, or any person who comes into physical contact or close physical proximity with an infected individual, or is exposed to bodily fluids or tissues from infected individuals, also has an increased risk of developing an Ebola virus infection. Moreover, a subject is at risk of contracting an Ebola virus infection due to proximity to an outbreak of the disease, e.g. a subject resides in a densely-populated city or in close proximity to subjects having confirmed or suspected Ebola virus infections, or choice of employment, e.g. maintenance personnel responsible for cleaning a hospital facility or institution where an Ebola patient has been treated, a hospital employee, a pharmaceutical researcher, an individual who has visited or who is planning to visit an area or country known to have or suspected to have an outbreak of Ebola virus, or a frequent flyer.

In certain embodiments, the antibody or antigen-binding fragment thereof of the invention is administered in combination with a second therapeutic agent to the subject in need thereof. The second therapeutic agent may be selected from the group consisting of an anti-inflammatory drug (such as corticosteroids, and non-steroidal anti-inflammatory drugs), an anti-infective drug, an anti-viral drug, a different antibody to Ebola virus, a vaccine for Ebola virus, TKM Ebola (small interfering RNAs that target viral RNA polymerase) brincidofovir (CMX-001), favipiravir (T-705), BCX-4430, AVI-7537 (antisense phosphorodiamidate morpholino oligomers that target Ebola virus VP24 gene), interferons, a dietary supplement such as anti-oxidants and any other drug or therapy known in the art useful for ameliorating at least one symptom of the Ebola virus infection, or for reducing the viral load in a patient. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, intranasally, intramuscularly, or intracranially. In one embodiment, the antibody may be administered as a single intravenous infusion for maximum concentration of the antibody in the serum of the subject. The antibody or fragment thereof may be administered at a dose of about 0.1 mg/kg of body weight to about 100 mg/kg of body weight of the subject. In certain embodiments, an antibody of the present invention may be administered at one or more doses comprising between 50 mg to 600 mg.

The present invention also includes an anti-Ebola virus antibody or antigen-binding fragment thereof of the invention for use in treating a subject who has, or is suspected of having, or has been exposed to EBOV, or for use in the manufacture of a medicament for the treatment of a disease or disorder that would benefit from the blockade of Ebola virus binding and/or activity.

Other embodiments will become apparent from a review of the ensuing detailed description.

DETAILED DESCRIPTION

Figure 1:
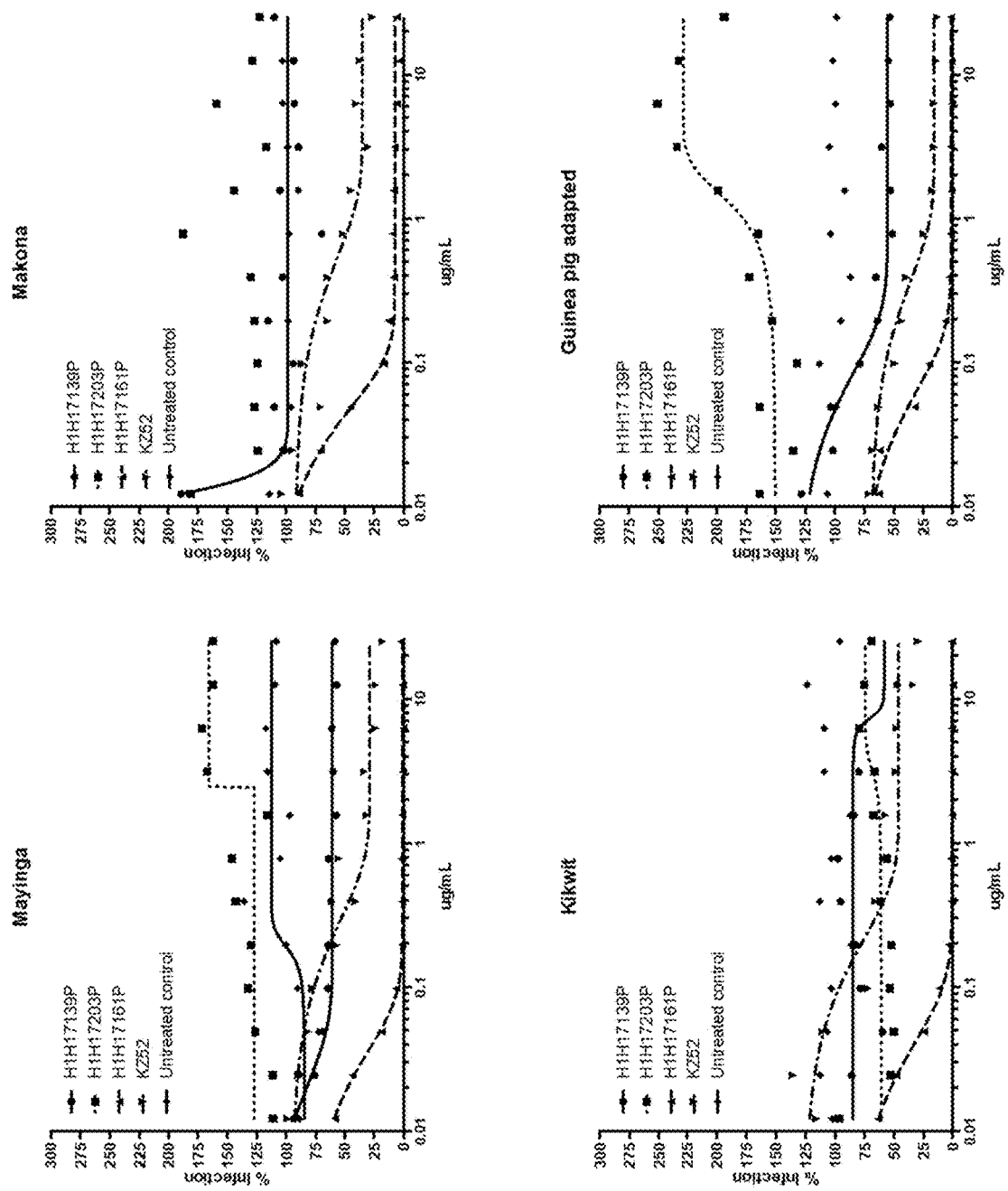
FIG. 1: H1H17161P potently neutralizes live EBOV.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All patents, applications and non-patent publications mentioned in this specification are incorporated herein by reference in their entireties.

Definitions

"Ebola virus" or "EBOV" is a genus of the Filoviridae family, which is known to cause severe and rapidly progressing hemorrhagic fever. There are many different Ebola virus species and strains based on nucleotide sequence and outbreak location, for example, Zaire, Tai Forest (previously known as Cote d'Ivoire or Ivory Coast), Sudan, Reston, and Bundibugyo. The most lethal forms of the virus are the Zaire and Sudan strains. The Reston strain is the only strain known to infect only non-human primates. The term "Ebola virus" also includes variants of Ebola virus isolated from different Ebola virus isolates.

The amino acid sequence of full-length Ebola virus glycoprotein, noted herein as "EBOV GP" or "Ebola virus GP" is exemplified by the amino acid sequences found in GenBank as accession numbers AHX24649.1 (See also SEQ ID NO: 314) and AHX24649.2 (See also SEQ ID NO: 315). The term also encompasses Ebola virus GP or a fragment thereof coupled to, for example, a histidine tag (e.g. see accession number AHX24649.1 with a decahistidine tag (SEQ ID NO: 318)), mouse or human Fc, or a signal sequence. The amino acid sequence of the "soluble GP" or "sGP" is shown in accession number AHX24650 and as SEQ ID NO 316 (with a signal sequence) and also SEQ ID NO: 317 (without the signal sequence but with a myc-myc-hexahistidine tag). The amino acid sequence of "GP1" starts at the amino terminal end of full length GP at residue 1 and ends at residue 501 of SEQ ID NO: 315. The amino acid sequence of "GP2" spans residues 502 through 676 of full length GP shown as SEQ ID NO: 315.

The term "Ebola virus infection", or "EBOV infection", as used herein refers to the severe hemorrhagic fever resulting from exposure to the virus, or to an infected animal, or to an infected human patient, or contact with the bodily fluids or tissues from an animal or human patient having an Ebola virus infection. The "symptoms associated with an Ebola virus infection" include fever, headache, fatigue, loss of appetite, myalgia, diarrhea, vomiting, abdominal pain, dehydration and unexplained bleeding.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-Ebola virus monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-Ebola virus monoclonal antibodies comprising variants of any of the HCVR, LCVR, and/or CDR amino acid sequences disclosed herein having one or more conservative substitutions. For example, the present invention includes anti-Ebola virus antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-7}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to Ebola virus. Moreover, multi-specific antibodies that bind to one domain in Ebola virus and one or more additional antigens or a bi-specific that binds to two different regions of Ebola virus are nonetheless considered antibodies that "specifically bind", as used herein.

The term "high affinity" antibody refers to those mAbs having a binding affinity to Ebola virus, expressed as $K_D$, of at least $10^{-7}$ M; preferably $10^{-8}$ M; more preferably $10^{-8}$ M, even more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from Ebola virus, or a virus like particle expressing the Ebola virus GP, with a rate constant of $1 \times 10^{-3}$ $s^{-1}$ or less, preferably $1 \times 10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to Ebola virus.

In specific embodiments, antibody or antibody fragments of the invention may be conjugated to a moiety such a ligand or a therapeutic moiety ("immunoconjugate"), such as an anti-viral drug, a second anti-Ebola virus antibody, or any other therapeutic moiety useful for treating an infection caused by Ebola virus.

An "isolated antibody", as used herein, is intended to refer to an antibody that is substantially free of other antibodies (Abs) having different antigenic specificities (e.g., an isolated antibody that specifically binds Ebola virus, or a fragment thereof, is substantially free of Abs that specifically bind antigens other than Ebola virus.

A "blocking antibody" or a "neutralizing antibody", as used herein (or an "antibody that neutralizes Ebola virus activity" or "antagonist antibody"), is intended to refer to an antibody whose binding to Ebola virus results in inhibition of at least one biological activity of Ebola virus. For example, an antibody of the invention may prevent or block Ebola virus attachment to, or entry into a host cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool.

"Antibody-dependent cell-mediated cytotoxicity" or "ADCC" is a mechanism of cell-mediated immune defense whereby an effector cell of the immune system actively lyses a target cell, whose membrane-surface antigens have been bound by specific antibodies, such as by those described herein. As such, it is one mechanism through which, for example, a virus specific antibody can act to limit the spread of infection. Classical ADCC is mediated by natural killer cells (NK cells), macrophages, neutrophils and in certain instances, eosinophils.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference anti-Ebola virus antibody of the invention, the reference antibody is allowed to bind to an Ebola virus GP or peptide under saturating conditions. Next, the ability of a test antibody to bind to the Ebola virus GP is assessed. If the test antibody is able to bind to Ebola virus GP following saturation binding with the reference anti-Ebola virus GP antibody, it can be concluded that the test antibody binds to a different epitope than the reference anti-Ebola virus antibody. On the other hand, if the test antibody is not able to bind to the Ebola virus GP following saturation binding with the reference anti-Ebola virus GP antibody, then the test antibody may bind to the same epitope as the epitope bound by the reference anti-Ebola virus GP antibody of the invention.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as viral infection. The subject may have an Ebola virus infection or is predisposed to developing an Ebola virus infection. Subjects "predisposed to developing an Ebola virus infection", or subjects "who may be at elevated risk for contracting an Ebola virus infection", are those subjects with compromised immune systems because of autoimmune disease, those persons receiving immunosuppressive therapy (for example, following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subjects of extreme young or old age are at increased risk. Any person who comes into physical contact or close physical proximity with an infected animal, or human patient, or is exposed to bodily fluids or tissues from an infected animal or human patient, has an increased risk of developing an Ebola virus infection. Moreover, a subject is at risk of contracting an Ebola virus infection due to proximity to an outbreak of the disease, e.g. subject resides in a densely-populated city or in close proximity to subjects having confirmed or suspected infections of Ebola virus, or choice of employment, e.g. hospital worker, pharmaceutical researcher, an individual who has visited or who is planning to visit an area or country known to have or suspected to have an outbreak of Ebola virus, or a frequent flyer.

As used herein, the terms "treat", "treating", or "treatment" refer to the reduction or amelioration of the severity of at least one symptom or indication of Ebola virus infection due to the administration of a therapeutic agent such as an antibody of the present invention to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of Ebola virus infection or any symptoms or indications of Ebola virus infection upon administration of an antibody of the present invention. The term includes prevention of spread of infection in a subject exposed to the virus or at risk of having Ebola virus infection.

As used herein, the term "anti-viral drug" refers to any anti-infective agent or therapy, whether it be a chemical moiety, or a biological therapy, used to treat, prevent, or ameliorate a viral infection in a subject. For example, in the present invention an anti-viral drug may include, but not be limited to, an antibody to Ebola virus (in one embodiment the antibody to Ebola virus may be different than those described herein), a vaccine for Ebola virus, TKM Ebola (small interfering RNAs that target viral RNA polymerase) brincidofovir (CMX-001), favipiravir (T-705), BCX-4430, AVI-7537 (antisense phosphorodiamidate morpholino oligomers that target Ebola virus VP24 gene) and interferons. In the present invention, the infection to be treated is caused by an Ebola virus.

General Description

Ebola virus disease is a severe, often fatal disease caused by filamentous viral particles that are members of the family Filoviridae. There are several known species of the genus Ebola virus that are capable of causing disease in humans. These include Zaire, Sudan, Tai Forest (formerly Ivory Coast) and Bundibugyo. The natural reservoir for the virus is unknown and to date there are no approved therapies or vaccines.

The genome of the virus consists of a single strand of negative sense RNA of approximately 19 kb in length. Ebola virions contain seven proteins: a surface glycoprotein (GP), a nucleoprotein (NP), four virion structural proteins (VP40, VP35, VP30, and VP24), and an RNA-dependent RNA polymerase (L). (Feldman, et al. (1992) Virus Res. 24, 1-19).

The only protein present on the surface of the virus is the glycoprotein. Due to RNA editing, the transcription of the GP gene results in the synthesis of several GP gene specific mRNAs coding for viral GPs including non-structural soluble GP (sGP) and surface virion GP (Volchkova, V A et al., (1998), Virology 250:408-414). Both GPs are synthesized as a precursor molecule that is proteolytically cleaved by the cellular protease furin during intracellular processing (Volchkov, V E, et al., ((1998), Proc Natl Acad Sci USA 95:5762-5767). sGP forms dimers, whereas the cleaved carboxy-terminus fragment is a monomer. Viral surface spikes are formed as a trimer of $GP_{1,2}$ made up of two subunits GP1 and GP2 linked by a disulfide bond (Volchkova, V A et al., (1998), Virology 250:408-414; Falzarano, D. et al., (2006), Chembiochem 7:1605-1611). GP1 is known to mediate viral attachment to the host cell and GP2 is involved in membrane fusion (Sanchez, A. et al., (1996), Proc Natl Acad Sci USA 93:3602-3607; Alazard-Dany, N., et al. (2006), J. Gen. Virol. 87:1247-1257).

During infection with EBOV, significant amounts of soluble glycoproteins (sGP) are released from virus-infected cells. This form of GP has been shown to bind to and sequester virus-neutralizing antibodies directed against surface or virion GP (Dolnik, O. et al., (2004), EMBO J 23:2175-2184). Other than this antibody-blockade, the role of soluble GP in terms of viral replication and/or pathogenicity has not been well defined. More recent studies by Escudero-Perez, et al., have shown that sGP may bind to and activate non-infected dendritic cells and macrophages and induce the secretion of pro- and anti-inflammatory cytokines. In addition, they demonstrated that sGP affects endothelial cell function and may affect vascular permeability. (Escudero-Perez, et al., (2014), PLOS Pathogens, Vol. 10, Issue 11:1-17). This may explain the dysregulated inflammatory host reaction following infection and may contribute to virus pathogenicity.

Passive immunotherapy for prophylaxis or treatment of infectious diseases has been used for more than a century, usually in the form of convalescent human sera that contains high titers of neutralizing antibodies (Good et al., (1991); Cancer 68: 1415-1421). Today, multiple purified monoclonal antibodies are currently in preclinical and clinical development for use as anti-microbials (Marasco et al 2007; Nature Biotechnology 25: 1421-1434). Certain antibodies have been described that bind to the Ebola virus glycoprotein. (See e.g. Audet et. al. (2014), Scientific Reports 4:6881; Chen, et. al. (2014), ACS Chem Biol. October 17; 9(10): 2263-73; Koellhoffer J F, et al., (2012), Chembiochem November 26; 13(17):2549-57; Qiu, X., et. al., Nature (2014) October 2; 514(7520):47-53).

The inventors have described herein fully human antibodies and antigen-binding fragments thereof that specifically bind to Ebola virus GP and modulate the interaction of Ebola virus with those cells. The anti-Ebola virus GP antibodies may bind to the Ebola virus with high affinity. In certain embodiments, the antibodies of the present invention are blocking antibodies wherein the antibodies may bind to Ebola virus GP and block the attachment to and/or entry of the virus into host cells. In certain embodiments, the antibodies of the invention may block the binding of Ebola virus to cells and as such may inhibit or neutralize viral infection of host cells. In certain embodiments, the antibodies of the invention may mediate antibody dependent cell-mediated cytotoxicity (ADCC) and as such, may aid in destroying cells that harbor the virus. In certain embodiments, the antibodies may act in both fashions, e.g. they may neutralize viral infectivity and may mediate ADCC. In some embodiments, the antibodies may be useful for treating a subject suffering from an Ebola virus infection. The antibodies when administered to a subject in need thereof may reduce the infection by a virus such as Ebola virus in the subject. They may be used to decrease viral loads in a subject. They may be used alone or as adjunct therapy with other therapeutic moieties or modalities known in the art for treating a viral infection. In certain embodiments, these antibodies may bind to an epitope in the amino terminus of the Ebola virus GP. In certain embodiments, these antibodies may bind to an epitope in the carboxy terminus of the Ebola virus GP. Furthermore, the identified antibodies can be used prophylactically (before infection) to protect a mammal from infection, or can be used therapeutically (after infection is established) to ameliorate a previously established infection, or to ameliorate at least one symptom associated with the infection.

The full-length amino acid sequence of an exemplary Ebola virus GP is shown in GenBank as accession numbers AHX24649.1 and AHX24649.2 and also in SEQ ID NOs: 314 and 315, respectively. GP1 spans from amino acid residue 1-501 of the full length GP and GP2 spans from amino acid residue 502 through 676 of the full length GP shown in SEQ ID NOs 314 or SEQ ID NO: 315). The full length EBOV GP, also shown in accession number AHX24649.1, may be coupled to a decahistidine tag, such as shown in SEQ ID NO: 318. Soluble GP (sGP) is shown as GenBank accession number AHX24650.1 and also as SEQ ID NO: 316 (with the signal sequence attached) and also as SEQ ID NO: 317 (without the signal sequence, but containing a myc-myc-his tag).

In certain embodiments, the antibodies of the invention are obtained from mice immunized with a primary immunogen, such as a full-length Ebola virus GP, or with a recombinant form of Ebola virus GP or fragments thereof followed by immunization with a secondary immunogen, or with an immunogenically active fragment of Ebola virus GP. In certain embodiments, the antibodies are obtained from mice immunized with DNA encoding the full-length Ebola virus GP (Zaire.2014, see GenBank KJ660346.2; also SEQ ID NO: 313). The immunogen may be a biologically active and/or immunogenic fragment of Ebola virus GP or DNA encoding the active fragment thereof. The fragment may be derived from any region of the viral GP, including the amino-terminal fragment (e.g. GP1), or the carboxy-terminal fragment (e.g. GP2). The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-Ebola virus antibodies of the present invention are able to bind to and neutralize the activity of Ebola virus, as determined by in vitro or in vivo assays. The ability of the antibodies of the invention to bind to and neutralize the activity of Ebola virus and thus the attachment and/or entry of the virus into a host cell followed by the ensuing viral infection, may be measured using any standard method known to those skilled in the art, including binding assays, or activity assays, as described herein.

Non-limiting, exemplary in vitro assays for measuring binding activity are illustrated in Example 3, herein. In Example 3, the binding affinity and dissociation constants of anti-Ebola virus GP antibodies for Ebola virus were determined by Biacore. In Examples 4 and 7, neutralization assays were used to determine infectivity of diverse strains of Ebola virus.

The antibodies specific for Ebola virus GP may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to Ebola virus. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$—$C_L$; (viii) $V_L$—$C_H1$; (ix) $V_L$-$C_H2$; (x) $V_L$-$C_H3$; (xi) $V_L$-$C_H1$-$C_H2$; (Xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to Ebola virus GP. An immunogen comprising any one of the following can be used to generate antibodies to Ebola virus. In certain embodiments, the antibodies of the invention are obtained from mice immunized with a full-length, native Ebola virus GP (See, for example, GenBank accession numbers AHX24649.1 (SEQ ID NO: 314) and AHX24649.2 (SEQ ID NO: 315) or with DNA encoding the glycoprotein or fragment thereof. Alternatively, the Ebola virus GP or a fragment thereof may be produced using standard biochemical techniques and modified and used as immunogen. In one embodiment, the immunogen is a recombinantly produced Ebola virus GP or fragment thereof. In certain embodiments of the invention, the immunogen may be a commercially available Ebola virus GP. In certain embodiments, one or more booster injections may be administered. In certain embodiments, the booster injections may comprise one or more commercially available Ebola virus GPs. In certain embodiments, the immunogen may be a recombinant Ebola virus GP expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to Ebola virus GP are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-Ebola virus GP antibodies and antibody fragments of the present invention encompass proteins having amino acid sequences that vary from those of the described antibodies, but that retain the ability to bind Ebola virus. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-Ebola Virus Antibodies Comprising Fc Variants

According to certain embodiments of the present invention, anti-Ebola virus antibodies are provided comprising an Fc domain comprising one or more mutations that enhance or diminish antibody binding to the FcRn receptor, e.g., at acidic pH as compared to neutral pH. For example, the present invention includes anti-Ebola virus GP antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-Ebola virus antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein are contemplated within the scope of the present invention.

The present invention also includes anti-Ebola virus antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention function by binding to Ebola virus GP. For example, the present invention includes antibodies and antigen-binding fragments of antibodies that bind Ebola virus GP (e.g., at 25° C. or at 37° C.) with a $K_D$ of less than $10^{-7}$M, as measured by surface plasmon resonance, e.g., using the assay format as described herein. In certain embodiments, the antibodies or antigen-binding fragments thereof bind Ebola virus GP with a $K_D$ of less than about 10 nM, less than about 5 nM, less than about 1 nM, less than about 500 pM, less than 250 pM, or less than 100 pM, as measured by surface plasmon resonance, e.g., using the assay format as described herein, or a substantially similar assay.

The present invention also includes antibodies and antigen-binding fragments thereof that bind Ebola virus with a dissociative half-life (t½) of greater than about 3 minutes as measured by surface plasmon resonance at 25° C., or greater than about 1 minute as measured by surface plasmon resonance at 37° C. e.g., and at least a 3-fold increase in dissociative half-life (t½) at pH 5 or pH 6; using an assay format as defined herein, or a substantially similar assay. In certain embodiments, the antibodies or antigen-binding fragments of the present invention bind Ebola virus with a t½ of greater than about 10 minutes, of greater than about 30 minutes, of greater than about 60 minutes, of greater than about 100 minutes, of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., or at 37° C. e.g., using an assay format as defined herein (e.g., mAb-capture or antigen-capture format), or a substantially similar assay.

The present invention also includes antibodies or antigen-binding fragments thereof that neutralize the infectivity of Ebola virus for its host cells. In some embodiments, the antibodies exhibit a neutralization potency against Zaire.2014 VLPs with an $IC_{50}$ ranging from about $10^{-11}$ M to about $10^{-9}$ M. The antibodies of the invention also cross react with Ebola virus VLPs containing GPs from various strains of EBOV, including Zaire.1995, Zaire.2014, Ebola Sudan, Bundibugyo and Cote d'lvoire (Ivory Coast). The antibodies of the invention also mediate ADCC as shown in Example 5. Furthermore, the antibodies of the invention cross-compete with other antibodies that bind EBOV GP, as shown in Example 6.

In one embodiment, the invention provides an isolated recombinant antibody or antigen-binding fragment thereof that binds specifically to Ebola virus GP, wherein the antibody or fragment thereof exhibits one or more of the following characteristics: (a) is a fully human monoclonal antibody; (b) binds to EBOV, or a virus like particle (VLP) expressing an Ebola virus glycoprotein with a dissociation constant ($K_D$) of less than $10^{-7}$M, as measured in a surface plasmon resonance assay; (c) demonstrates at least a 3 fold increase in dissociative half-life (t½) at pH 5 or pH 6 relative to pH 7.4; (d) demonstrates neutralization of Zaire Ebola virus with an $IC_{50}$ ranging from about $10^{-11}$ M to about $10^{-9}$M; (e) demonstrates antibody dependent cellular cytotoxicity of Ebola virus infected cells; (f) cross reacts with one or more strains of Ebola virus VLPs selected from the group consisting of Zaire.2014, Zaire.1995, Sudan, Bundibugyo and Cote d'lvoire; (g) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

The antibodies of the present invention may possess one or more of the aforementioned biological characteristics, or any combinations thereof. Certain of the properties of the antibodies of the invention are summarized below. Other biological characteristics of the antibodies of the present invention will be evident to a person of ordinary skill in the art from a review of the present disclosure including the working Examples herein.

| mAb | mAb Properties | Pseudo-virus neutralization IC50 (M) | Live Virus Neutralization | ADCC | sGP Binding |
|---|---|---|---|---|---|
| H1H17161P | Neutralizer, ADCC−, sGP− | 8.3E−11 | Yes | No | No |
| H1H17139P | Non Neutralizer, ADCC+, sGP+ | No | No | Yes | Yes |
| H1H17203P | Neutralizer, ADCC+, sGP− | 2E−10 | No | Yes | No |

Epitope Mapping and Related Technologies

The present invention includes anti-Ebola virus antibodies that interact with one or more amino acids found within the GP of Ebola virus. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the Ebola virus GP molecule (e.g. a linear epitope in a domain). Alternatively, the epitope may consist of a plurality of noncontiguous amino acids (or amino acid sequences) located within the Ebola virus GP (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the Ebola virus antibodies or antigen-binding fragments thereof bind an epitope within any one or more of the regions exemplified in Ebola virus GP, either in natural form, or recombinantly produced, or to a fragment thereof.

The present invention includes anti-Ebola virus GP antibodies that bind to the same epitope, or a portion of the epitope. Likewise, the present invention also includes anti-Ebola virus GP antibodies that compete for binding to Ebola virus GP or a fragment thereof with any of the specific exemplary antibodies described herein. For example, the present invention includes anti-Ebola virus GPP antibodies that cross-compete for binding to Ebola virus with one or more antibodies obtained from those antibodies described in Tables 1 and 2.

One can easily determine whether an antibody binds to the same epitope as, or competes for binding with, a reference anti-Ebola virus GP antibody by using routine methods known in the art. For example, to determine if a test antibody binds to the same epitope as a reference anti-Ebola virus GP antibody of the invention, the reference antibody is allowed to bind to a Ebola virus GP or peptide under saturating conditions. Next, the ability of a test antibody to bind to the Ebola virus GP is assessed. If the test antibody is able to bind to Ebola virus GP following saturation binding with the reference anti-Ebola virus GP antibody, it can be concluded that the test antibody binds to a different epitope than the reference anti-Ebola virus antibody. On the other hand, if the test antibody is not able to bind to the Ebola virus GP following saturation binding with the reference anti-Ebola virus GP antibody, then the test antibody may bind to the same epitope as the epitope bound by the reference anti-Ebola virus GP antibody of the invention.

To determine if an antibody competes for binding with a reference anti-Ebola virus GP antibody, the above-described binding methodology is performed in two orientations: In a first orientation, the reference antibody is allowed to bind to a Ebola virus GP under saturating conditions followed by assessment of binding of the test antibody to the Ebola virus GP. In a second orientation, the test antibody is allowed to bind to an Ebola virus GP under saturating conditions followed by assessment of binding of the reference antibody to the Ebola virus GP. If, in both orientations, only the first (saturating) antibody is capable of binding to the Ebola virus GP, then it is concluded that the test antibody and the reference antibody compete for binding to Ebola virus GP. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-Ebola virus GP monoclonal antibody conjugated to a therapeutic moiety ("immunoconjugate"), such as an anti-viral drug to treat Ebola virus infection. As used herein, the term "immunoconjugate" refers to an antibody, which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to Ebola virus, or Ebola virus GP. In certain embodiments, the antibody may be conjugated to an agent specific for a virally infected cell. The type of therapeutic moiety that may be conjugated to the anti-Ebola virus antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, Ebola virus-specific antibodies are generated in a bi-specific format (a "bi-specific") in which variable regions binding to distinct domains of Ebola virus are linked together to confer dual-domain specificity within a single binding molecule. Appropriately designed bi-specifics may enhance overall Ebola virus-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different anti-Ebola virus antibody, may be prepared in a bi-specific format using techniques described herein, or other techniques known to those skilled in the art. Antibody variable regions binding to distinct regions may be linked together with variable regions that bind to relevant sites on, for example, Ebola virus, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

Therapeutic Administration and Formulations

The invention provides therapeutic compositions comprising the anti-Ebola virus GP antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the present invention are useful for the treatment, and/or prevention of a disease or disorder or condition associated with Ebola virus infection and/or for ameliorating at least one symptom associated with such disease, disorder or condition.

In certain embodiments, the antibodies of the invention are useful to treat subjects suffering from the severe and acute respiratory infection caused by Ebola virus. In some embodiments, the antibodies of the invention are useful in decreasing viral titers or reducing viral load in the host. In one embodiment, an antibody or antigen-binding fragment thereof the invention may be administered at a therapeutic dose to a patient with Ebola virus infection.

One or more antibodies of the present invention may be administered to relieve or prevent or decrease the severity of one or more of the symptoms or conditions of the disease or disorder. The antibodies may be used to ameliorate or reduce the severity of at least one symptom of Ebola virus infection including, but not limited to fever, headache, fatigue, loss of appetite, myalgia, diarrhea, vomiting, abdominal pain, dehydration and unexplained bleeding.

It is also contemplated herein to use one or more antibodies of the present invention prophylactically to subjects at risk for developing an Ebola virus infection such as an immunocompromised individual, a healthcare worker, a person who is suspected of having been exposed to a person harboring the Ebola virus, a person who comes into physical contact or close physical proximity with an infected individual, a hospital employee, a pharmaceutical researcher, maintenance personnel responsible for cleaning a hospital facility or institution where an Ebola patient has been treated, individuals who have visited or are planning to visit an area or country known to have or suspected to have an outbreak of Ebola virus or a frequent flyer.

In a further embodiment of the invention the present antibodies are used for the preparation of a pharmaceutical composition for treating patients suffering from an Ebola virus infection. In another embodiment of the invention, the present antibodies are used as adjunct therapy with any other agent or any other therapy known to those skilled in the art useful for treating or ameliorating an Ebola virus infection.

Combination Therapies

Combination therapies may include an anti-Ebola virus GP antibody of the invention and any additional therapeutic agent that may be advantageously combined with an antibody of the invention, or with a biologically active fragment of an antibody of the invention. The antibodies of the present invention may be combined synergistically with one or more drugs or agents used to treat Ebola virus infection.

For example, exemplary agents for treating a viral infection may include, e.g., anti-viral drug, an anti-inflammatory drug (such as corticosteroids, and non-steroidal anti-inflammatory drugs), a different antibody to Ebola virus, a vaccine for Ebola virus, TKM Ebola (small interfering RNAs that target viral RNA polymerase) brincidofovir (CMX-001), favipiravir (T-705), BCX-4430, AVI-7537 (antisense phosphorodiamidate morpholino oligomers that target Ebola virus VP24 gene), interferons, or any other palliative therapy to treat an Ebola virus infection.

In some embodiments, the antibodies of the invention may be combined with a second therapeutic agent to reduce the viral load in a patient with an Ebola virus infection, or to ameliorate one or more symptoms of the infection.

In certain embodiments, the second therapeutic agent is another different antibody, or antibody cocktail specific for Ebola virus GP, wherein the different antibody or antibodies within the cocktail may or may not bind to the same epitope, or an overlapping epitope, as an antibody of the present invention. In certain embodiments, the second therapeutic agent is an antibody to a different Ebola virus protein. The second antibody may be specific for one or more different Ebola virus proteins from different strains of the virus. It is contemplated herein to use a combination ("cocktail") of the antibodies of the invention with neutralization or inhibitory activity against Ebola virus. In some embodiments, non-competing antibodies may be combined and administered to a subject in need thereof, to reduce the ability of Ebola virus to escape due to mutation. In some embodiments, the antibodies comprising the combination bind to distinct non-overlapping epitopes on the GP. The antibodies comprising the combination may block the virus attachment and/or entry into and/or fusion with host cells. The antibodies may interact with the GP from a strain of EBOV selected from Zaire, Sudan, Bundibugyo, or Cote d'lvoire, and when used alone, or in combination with any one or more of the agents noted above, may neutralize any one or more of the Ebola virus strains noted.

It is also contemplated herein to use a combination of anti-Ebola virus GP antibodies of the present invention, wherein the combination comprises one or more antibodies that do not cross-compete. In certain embodiments, the combination includes a cocktail comprising a mixture of at least three antibodies of the invention. The antibodies within the cocktail may differ in their ability to neutralize virus or virus infected cells, or in their ability to mediate antibody-dependent cellular cytotoxicity (ADCC), or in their ability to bind EBOV soluble glycoprotein (sGP).

As used herein, the term "in combination with" means that additional therapeutically active component(s) may be administered prior to, concurrent with, or after the administration of at least one anti-Ebola virus GP antibody of the invention, or a cocktail comprising one or more of the antibodies the present invention. The term "in combination with" also includes sequential or concomitant administration of an anti-Ebola virus GP antibody and a second therapeutic agent.

The additional therapeutically active component(s) may be administered to a subject prior to administration of an anti-Ebola virus GP antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-Ebola virus GP antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-Ebola virus GP antibody of the present invention. "Concurrent" administration, for purposes of the present invention, includes, e.g., administration of an anti-Ebola virus GP antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-Ebola virus GP antibody and the additional therapeutically active component may be administered intravenously, etc.); alternatively, each dosage form may be administered via a different route (e.g., the anti-Ebola virus GP antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-Ebola virus GP antibody "prior to", "concurrent with," or "after" (as those terms are defined herein above) administration of an additional therapeutically active component is considered administration of an anti-Ebola virus GP antibody "in combination with" an additional therapeutically active component.

The present invention includes pharmaceutical compositions in which an anti-Ebola virus GP antibody of the present invention is co-formulated with one or more of the additional therapeutically active component(s) as described elsewhere herein.

Administration Regimens

According to certain embodiments, a single dose of an anti-Ebola virus GP antibody of the invention (or a pharmaceutical composition comprising a combination of an anti-Ebola virus GP antibody and any of the additional therapeutically active agents mentioned herein) may be administered to a subject in need thereof. According to certain embodiments of the present invention, multiple doses of an anti-Ebola virus GP antibody (or a pharmaceutical composition comprising a combination of an anti-Ebola virus GP antibody and any of the additional therapeutically active agents mentioned herein) may be administered to a subject over a defined time course. The methods according to this aspect of the invention comprise sequentially administering to a subject multiple doses of an anti-Ebola virus GP antibody of the invention. As used herein, "sequentially administering" means that each dose of anti-Ebola virus GP antibody is administered to the subject at a different point in time, e.g., on different days separated by a predetermined interval (e.g., hours, days, weeks or months). The present invention includes methods which comprise sequentially administering to the patient a single initial dose of an anti-Ebola virus GP antibody, followed by one or more secondary doses of the anti-Ebola virus GP antibody, and optionally followed by one or more tertiary doses of the anti-Ebola virus GP antibody.

The terms "initial dose," "secondary doses," and "tertiary doses," refer to the temporal sequence of administration of the anti-Ebola virus GP antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-Ebola virus GP antibody, but generally may differ from one another in terms of frequency of administration. In certain embodiments, however, the amount of anti-Ebola virus GP antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-Ebola virus GP antibody, which is administered to a patient prior to the administration of the very next dose in the sequence with no intervening doses.

The methods according to this aspect of the invention may comprise administering to a patient any number of secondary and/or tertiary doses of an anti-Ebola virus GP antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-Ebola virus GP antibodies of the present invention may be used to detect and/or measure Ebola virus in a sample, e.g., for diagnostic purposes. Some embodiments contemplate the use of one or more antibodies of the present invention in assays to detect a disease or disorder such as viral infection. Exemplary diagnostic assays for Ebola virus may comprise, e.g., contacting a sample, obtained from a patient, with an anti-Ebola virus GP antibody of the invention, wherein the anti-Ebola virus GP antibody is labeled with a detectable label or reporter molecule or used as a capture ligand to selectively isolate Ebola virus from patient samples. Alternatively, an unlabeled anti-Ebola virus GP antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Ebola virus in a sample include enzyme-linked immunosorbent assay (ELISA), radioimmunoassay (RIA), and fluorescence-activated cell sorting (FACS).

Samples that can be used in Ebola virus diagnostic assays according to the present invention include any tissue or fluid sample obtainable from a patient, which contains detectable quantities of either Ebola virus, or fragments thereof, under normal or pathological conditions. Generally, levels of Ebola virus in a particular sample obtained from a healthy patient (e.g., a patient not afflicted with a disease associated with Ebola virus will be measured to initially establish a baseline, or standard, level of Ebola virus. This baseline level of Ebola virus can then be compared against the levels of Ebola virus measured in samples obtained from individuals suspected of having a Ebola virus-associated condition, or symptoms associated with such condition.

The antibodies specific for Ebola virus may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Ebola Virus

Human antibodies to Ebola virus were generated in a mouse comprising DNA encoding human immunoglobulin heavy and kappa light chain variable regions. In one embodiment, the human antibodies to Ebola virus were generated in a VELOCIMMUNE® mouse. In one embodiment, VelocImmune® (VI) mice were immunized with DNA encoding the full-length Ebola virus GP [Zaire ebolavirus 2014 (GenBank: KJ660346.2)]. Antibodies were generated following an accelerated regimen comprising 2 immunizations separated by 2 weeks. The antibody immune response was monitored by an Ebola virus GP-specific immunoassay. For example, sera were assayed for specific antibody titers to purified full-length EBOV GP, subunit GP proteins (GP1 and GP2), and virus-like particles (VLPs) expressing EBOV GP. Antibody-producing clones were isolated using both B-cell Sorting Technology (BST) and hybridoma methods. For example, when a desired immune response was achieved, splenocytes were harvested and fused with mouse myeloma cells to preserve their viability and form hybridoma cell lines. The hybridoma cell lines were screened and selected to identify cell lines that produce Ebola virus GP-specific antibodies. Using this technique, and the various immunogens described above, several chimeric antibodies (i.e., antibodies possessing human variable domains and mouse constant domains) were obtained; exemplary antibodies generated in this manner were designated as H1M17354N, H2aM17356N, H1M17357N, H2aM17358N, H2aM17359N and H2aM17360N.

Anti-Ebola virus antibodies were also isolated directly from antigen-positive mouse B cells without fusion to myeloma cells, as described in U.S. Pat. No. 7,582,298, herein specifically incorporated by reference in its entirety. Using this method, several fully human anti-Ebola virus GP antibodies (i.e., antibodies possessing human variable domains and human constant domains) were obtained; exemplary antibodies generated in this manner were designated as H1H17134P, H1H17139P, H1H17142P, H1H17151P, H1H17161P, H1H17162P, H1H17193P, H1H17196P, H1H17199P, H1H17203P, H1H17214P, H1H17219P, H1H17223P and H1H17228P.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-Ebola virus antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H17134P | 2 | 4 | 6 | 8 | 10 | 12 | 14 | 16 |
| H1H17139P | 18 | 20 | 22 | 24 | 26 | 28 | 30 | 32 |
| H1H17142P | 34 | 36 | 38 | 40 | 42 | 44 | 46 | 48 |
| H1H17151P | 50 | 52 | 54 | 56 | 58 | 60 | 62 | 64 |
| H1H17161P | 66 | 68 | 70 | 72 | 74 | 76 | 78 | 80 |
| H1H17162P | 82 | 84 | 86 | 88 | 90 | 92 | 94 | 96 |
| H1H17193P | 98 | 100 | 102 | 104 | 106 | 108 | 110 | 112 |
| H1H17196P | 114 | 116 | 118 | 120 | 122 | 124 | 126 | 128 |
| H1H17199P | 130 | 132 | 134 | 136 | 138 | 140 | 142 | 144 |
| H1H17203P | 146 | 148 | 150 | 152 | 154 | 156 | 158 | 160 |
| H1H17214P | 162 | 164 | 166 | 168 | 170 | 172 | 174 | 176 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H17219P | 178 | 180 | 182 | 184 | 186 | 188 | 190 | 192 |
| H1H17223P | 194 | 196 | 198 | 200 | 202 | 204 | 206 | 208 |
| H1H17228P | 210 | 212 | 214 | 216 | 218 | 220 | 222 | 224 |
| H1H17354N | 226 | 228 | 230 | 232 | 234 | 236 | 238 | 240 |
| H1H17356N | 242 | 244 | 246 | 248 | 250 | 252 | 254 | 256 |
| H1H17357N | 258 | 260 | 262 | 264 | 266 | 268 | 270 | 272 |
| H1H17358N2 | 274 | 276 | 278 | 280 | 282 | 284 | 286 | 288 |
| H1H17359N | 290 | 292 | 294 | 296 | 298 | 300 | 302 | 304 |
| H1H17360N | 306 | 308 | 310 | 312 | 282 | 284 | 286 | 288 |
| H1M17354N | 226 | 228 | 230 | 232 | 234 | 236 | 238 | 240 |
| H2aM17356N | 242 | 244 | 246 | 248 | 250 | 252 | 254 | 256 |
| H1M17357N | 258 | 260 | 262 | 264 | 266 | 268 | 270 | 272 |
| H2aM17358N | 274 | 276 | 278 | 280 | 282 | 284 | 286 | 288 |
| H2aM17359N | 290 | 292 | 294 | 296 | 298 | 300 | 302 | 304 |
| H2aM17360N | 306 | 308 | 310 | 312 | 282 | 284 | 286 | 288 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H17134P | 1 | 3 | 5 | 7 | 9 | 11 | 13 | 15 |
| H1H17139P | 17 | 19 | 21 | 23 | 25 | 27 | 29 | 31 |
| H1H17142P | 33 | 35 | 37 | 39 | 41 | 43 | 45 | 47 |
| H1H17151P | 49 | 51 | 53 | 55 | 57 | 59 | 61 | 63 |
| H1H17161P | 65 | 67 | 69 | 71 | 73 | 75 | 77 | 79 |
| H1H17162P | 81 | 83 | 85 | 87 | 89 | 91 | 93 | 95 |
| H1H17193P | 97 | 99 | 101 | 103 | 105 | 107 | 109 | 111 |
| H1H17196P | 113 | 115 | 117 | 119 | 121 | 123 | 125 | 127 |
| H1H17199P | 129 | 131 | 133 | 135 | 137 | 139 | 141 | 143 |
| H1H17203P | 145 | 147 | 149 | 151 | 153 | 155 | 157 | 159 |
| H1H17214P | 161 | 163 | 165 | 167 | 169 | 171 | 173 | 175 |
| H1H17219P | 177 | 179 | 181 | 183 | 185 | 187 | 189 | 191 |
| H1H17223P | 193 | 195 | 197 | 199 | 201 | 203 | 205 | 207 |
| H1H17228P | 209 | 211 | 213 | 215 | 217 | 219 | 221 | 223 |
| H1H17354N | 225 | 227 | 229 | 231 | 233 | 235 | 237 | 239 |
| H1H17356N | 241 | 243 | 245 | 247 | 249 | 251 | 253 | 255 |
| H1H17357N | 257 | 259 | 261 | 263 | 265 | 267 | 269 | 271 |
| H1H17358N2 | 273 | 275 | 277 | 279 | 281 | 283 | 285 | 287 |
| H1H17359N | 289 | 291 | 293 | 295 | 297 | 299 | 301 | 303 |
| H1H17360N | 305 | 307 | 309 | 311 | 281 | 283 | 285 | 287 |
| H1M17354N | 225 | 227 | 229 | 231 | 233 | 235 | 237 | 239 |
| H2aM17356N | 241 | 243 | 245 | 247 | 249 | 251 | 253 | 255 |
| H1M17357N | 257 | 259 | 261 | 263 | 265 | 267 | 269 | 271 |
| H2aM17358N | 273 | 275 | 277 | 279 | 281 | 283 | 285 | 287 |
| H2aM17359N | 289 | 291 | 293 | 295 | 297 | 299 | 301 | 303 |
| H2aM17360N | 305 | 307 | 309 | 311 | 281 | 283 | 285 | 287 |

Antibodies are typically referred to herein according to the following nomenclature: Fc prefix (e.g. "H1H," "H2M," etc.), followed by a numerical identifier (e.g. "17139," "17161," etc., as shown in Table 1 or 2), followed by a "P," "P2," "N", N2, or "B" suffix. The H1H and H2M prefixes on the antibody designations used herein indicate the particular Fc region isotype of the antibody. Thus, according to this nomenclature, an antibody may be referred to herein as, e.g., "H1H17359N," "H2aM17359N," etc. For example, an "H1M" antibody has a mouse IgG1 Fc, and an "H2M" antibody has a mouse IgG2 Fc (a or b isotype) (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1 or 2—will remain the same, and the binding properties to antigen are expected to be identical or substantially similar regardless of the nature of the Fc domain.

Example 3: Antibody Binding to Ebola Virus GP as Determined by Surface Plasmon Resonance A. pH Dependent Dissociation Rate Constant at 37° C.

Binding dissociation rate constants ($k_d$) and dissociation half-lives ($t_{1/2}$) for Ebola virus GP binding to purified anti-Ebola virus GP monoclonal antibodies at 37° C. were determined using a real-time surface plasmon resonance biosensor assay on a Biacore T200 instrument. The CM4

Biacore sensor surface was derivatized by amine coupling with a monoclonal mouse anti-human Fc antibody (GE, #BR-1008-39) or monoclonal goat anti-mouse Fc antibody (GE, #BR-1008-38) to capture purified anti-Ebola virus GP mAbs. All Biacore binding studies in Example 3A were performed in a buffer composed of 0.01M $Na_2HPO_4/NaH_2PO_4$, 0.15M NaCl, 0.05% v/v Surfactant P20 (PBS-P running buffer) at pHs 7.4, 6.0 and 5.0. The low pH chase was performed to assess whether the antibodies maintain binding at low pH. This would mimic the conditions that the virus will encounter during membrane fusion, upon acidification of the endosome. Different concentrations of Ebola virus GP with a C-terminal polyhistidine tag (EbolaGP.his; Sino Biologicals, Catalog #40442-V08131) prepared in PBS-P running buffer (ranging from 90 nM to 11.1 nM, 3-fold dilutions) were injected over the anti-Ebola virus GP mAb captured surface at a flow rate of 25 µL/minute. Association of Ebola virus GP to the captured monoclonal antibody was monitored for 5 minutes and the dissociation of Ebola virus GP in PBS-P running buffer was monitored for 6 minutes. All of the dissociation rate constant experiments were performed at 37° C. Kinetic dissociation ($k_d$) rate constants were determined by fitting the real-time sensorgrams to a 1:1 binding model using Scrubber 2.0c curve fitting software. The dissociative half-lives (t½) were calculated from the kinetic rate constants as:

$$t1/2 \text{ (min)} = \frac{\ln(2)}{60*kd}$$

Dissociation rate parameters for Ebola virus GP binding to purified anti-Ebola virus GP mAbs at 37° C. are shown in Table 3.

TABLE 3 pH dependence of dissociative half-lives at 37° C.

| mAb Captured | t½ Ratio pH7.4/pH6.0 | pH7.4/pH5.0 |
|---|---|---|
| H1H1238N(−) control | NB | NB |
| H1H17162P | 0.3 | 0.3 |
| H1H17177P | 0.2 | 0.2 |
| H1H17193P | 1.1 | 0.8 |
| H1H17196P | 1.0 | 1.0 |
| H1H17150P | 0.2 | 0.2 |
| H1H17151P | 0.03 | 0.01 |
| H1H17160P | 0.2 | 0.4 |
| H1H17161P | 0.2 | 0.2 |
| H1H17214P | 1.0 | 1.0 |
| H1H17219P | 1.0 | 1.0 |
| H1H17223P | 0.4 | 0.4 |
| H1H17228P | 0.6 | 0.5 |
| H1H17142P | 0.5 | 0.5 |
| H1H17141P | 0.3 | 0.3 |
| H1H17139P | 0.2 | 0.2 |
| H1H17134P | 0.6 | 0.6 |
| H1H17211P | 6.7 | 3.0 |
| H1H17210P | 0.2 | 0.2 |
| H1H17203P | 0.2 | 0.1 |
| H1H17199P | 0.4 | 0.1 |
| H1M17348N | 0.3 | 0.4 |
| H1M17349N | 2.7 | 6.9 |
| H1M17350N | 0.1 | 1.1 |
| H1M17351N | NB | NB |
| H1M17352N | 1.1 | 1.1 |

TABLE 3-continued pH dependence of dissociative half-lives at 37° C.

| mAb Captured | t½ Ratio pH7.4/pH6.0 | pH7.4/pH5.0 |
|---|---|---|
| H1M17353N | 1.6 | 0.3 |
| H1M17354N | 1.3 | 1.3 |
| H1M17357N | 0.8 | 0.5 |
| H2aM17355N | 0.5 | 0.6 |
| H2aM17356N | 0.9 | 0.9 |
| H2aM17358N | 0.7 | 0.4 |
| H2aM17359N | 0.8 | 0.7 |
| H2aM17360N | 0.2 | 0.5 |
| H2aM17361N | 0.2 | 0.5 |

NB-No detectable binding under assays conditions tested

B. Binding Affinity and Kinetics at 25° C. and 37° C.

Equilibrium dissociation constants ($K_D$ values) for Ebola virus GP binding to purified anti-Ebola virus GP mAbs were determined using a real-time surface plasmon resonance biosensor using a Biacore 4000 instrument. The CM4 Biacore sensor surface was derivatized by amine coupling with a monoclonal mouse anti-human Fc antibody (GE, #BR-1008-39) or monoclonal goat anti-mouse Fc antibody (GE, #BR-1008-38) to capture purified anti-Ebola virus GP mAbs. All Biacore binding studies in Example 3B were performed in a buffer composed of 0.01M HEPES pH 7.4, 0.15M NaCl, 3 mM EDTA, 0.05% v/v Surfactant P20 (HBS-ET running buffer). Different concentrations of Ebola virus GP with a C-terminal polyhistidine tag (Sino Biologicals, Catalog #40442-V08131) prepared in HBS-ET running buffer (ranging from 90 nM to 3.3 nM, 3-fold dilutions) were injected over the anti-Ebola virus GP mAb captured surface at a flow rate of 304/minute. Association of Ebola virus GP to the captured monoclonal antibody was monitored for 5 minutes and the dissociation of Ebola virus GP in HBS-ET running buffer was monitored for 10 minutes. All of the binding kinetics experiments were performed at 25° C. and 37° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D (M) = \frac{kd}{ka}, \text{ and } t1/2 \text{ (min)} = \frac{\ln(2)}{60*kd}$$

Binding kinetic parameters for Ebola virus GP binding to purified anti-Ebola virus GP mAbs at 25° C. and 37° C. are shown in Tables 4A and 4B.

TABLE 4A

Binding Kinetics at 25° C.

| mAb | ka (1/Ms) | kd (1/s) | KD (M) | t1/2 (min) |
|---|---|---|---|---|
| H1H17162P | 2.18E+04 | ≤1E−5 | 4.60E−10 | ≥1155 |
| H1H17177P | 3.18E+03 | 1.12E−05 | 3.53E−09 | 1030.3 |
| H1H17193P | 4.58E+03 | 1.08E−04 | 2.36E−08 | 106.6 |
| H1H17196P | 2.56E+04 | ≤1E−5 | 3.91E−10 | ≥1155 |
| H1H17150P | 2.16E+04 | 5.42E−05 | 2.51E−09 | 213.1 |
| H1H17151P | 1.26E+04 | 9.44E−05 | 7.49E−09 | 122.3 |

TABLE 4A-continued

Binding Kinetics at 25° C.

| mAb | ka (1/Ms) | kd (1/s) | KD (M) | t1/2 (min) |
|---|---|---|---|---|
| H1H17160P | 6.85E+04 | 3.76E-03 | 5.48E-08 | 3.1 |
| H1H17161P | 5.29E+04 | ≤1E-5 | 1.89E-10 | ≥1155 |
| H1H17214P | 3.76E+04 | ≤1E-5 | 2.66E-10 | ≥1155 |
| H1H17219P | 3.11E+04 | 2.90E-05 | 9.34E-10 | 398.3 |
| H1H17223P | 3.00E+04 | 6.08E-05 | 2.03E-09 | 190.0 |
| H1H17228P | 4.49E+04 | 1.69E-03 | 3.76E-08 | 6.9 |
| H1H17142P | 2.00E+04 | 2.81E-05 | 1.41E-09 | 410.7 |
| H1H17141P | 1.98E+04 | 9.69E-05 | 4.90E-09 | 119.2 |
| H1H17139P | 2.29E+04 | 1.63E-04 | 7.13E-09 | 70.8 |
| H1H17134P | 7.65E+04 | 9.41E-04 | 1.23E-08 | 12.3 |
| H1H17211P | 3.33E+04 | 2.14E-04 | 6.43E-09 | 54.0 |
| H1H17210P | 1.09E+02 | 2.06E-04 | 1.89E-06 | 56.0 |
| H1H17203P | 2.78E+04 | 1.68E-04 | 6.04E-09 | 68.7 |
| H1H17199P | 1.25E+04 | 2.36E-04 | 1.89E-08 | 49.0 |
| H1M17348N | IC | IC | IC | IC |
| H1M17349N | 7.03E+04 | 8.69E-04 | 1.24E-08 | 13.3 |
| H1M17350N | IC | IC | IC | IC |
| H1M17351N | NB | NB | NB | NB |
| H1M17352N | IC | IC | IC | IC |
| H1M17353N | IC | IC | IC | IC |
| H1M17354N | 4.94E+04 | 3.16E-03 | 6.39E-08 | 3.7 |
| H1M17357N | IC | IC | IC | IC |
| H2aM17355N | 1.44E+04 | ≤1E-5 | 6.96E-10 | ≥1155 |
| H2aM17356N | 2.18E+04 | 9.57E-05 | 4.40E-09 | 120.7 |
| H2aM17358N | 3.22E+02 | 2.01E-04 | 6.23E-07 | 57.5 |
| H2aM17359N | 3.82E+03 | 1.95E-04 | 5.09E-08 | 59.4 |
| H2aM17360N | 2.30E+04 | 1.06E-05 | 4.63E-10 | 1086.5 |
| H2aM17361N | 1.22E+02 | 1.25E-04 | 1.02E-06 | 92.5 |

NB-No detectable binding under assays conditions tested
IC-Inconclusive binding sensogram for fitting

TABLE 4B

Binding Kinetics at 37° C.

| mAb | ka (1/Ms) | kd (1/s) | KD (M) | t1/2 (min) |
|---|---|---|---|---|
| H1H17162P | 3.47E+04 | ≤1E-5 | 2.88E-10 | ≥1155 |
| H1H17177P | 1.68E+04 | 1.62E-04 | 9.62E-09 | 71.3 |
| H1H17193P | 1.58E+04 | 5.03E-04 | 3.18E-08 | 22.9 |
| H1H17196P | 3.16E+04 | ≤1E-5 | 3.17E-10 | ≥1155 |
| H1H17150P | 3.18E+04 | 3.94E-05 | 1.24E-09 | 292.8 |
| H1H17151P | 2.26E+04 | 3.83E-04 | 1.70E-08 | 30.2 |
| H1H17160P | 5.72E+04 | 5.63E-03 | 9.85E-08 | 2.1 |
| H1H17161P | 4.39E+04 | ≤1E-5 | 2.28E-10 | ≥1155 |
| H1H17214P | 3.67E+04 | 1.54E-04 | 4.20E-09 | 74.9 |
| H1H17219P | 4.41E+04 | ≤1E-5 | 2.27E-10 | ≥1155 |
| H1H17223P | 3.51E+04 | 2.42E-04 | 6.89E-09 | 47.7 |
| H1H17228P | 7.32E+04 | 3.83E-03 | 5.23E-08 | 3 |
| H1H17142P | 2.60E+04 | 1.74E-04 | 6.68E-09 | 66.6 |
| H1H17141P | 2.65E+04 | 2.92E-04 | 1.10E-08 | 39.6 |
| H1H17139P | 2.48E+04 | 5.12E-04 | 2.06E-08 | 22.5 |
| H1H17134P | 6.99E+04 | 4.69E-04 | 6.70E-09 | 24.6 |
| H1H17211P | 1.90E+04 | 7.31E-04 | 3.84E-08 | 15.8 |
| H1H17210P | 6.19E+02 | 6.12E-04 | 9.89E-07 | 18.9 |
| H1H17203P | 3.85E+04 | 1.19E-03 | 3.09E-08 | 9.7 |
| H1H17199P | 3.04E+04 | 1.28E-03 | 4.22E-08 | 9 |
| H1M17348N | IC | IC | IC | IC |
| H1M17349N | 1.77E+04 | 1.93E-03 | 1.09E-07 | 6 |
| H1M17350N | 4.84E+02 | 1.00E-03 | 2.07E-06 | 11.5 |
| H1M17351N | NB | NB | NB | NB |
| H1M17352N | 4.09E+04 | 1.55E-03 | 3.80E-08 | 7.4 |
| H1M17353N | 2.33E+02 | 5.38E-04 | 2.31E-06 | 21.5 |
| H1M17354N | 5.08E+04 | 5.73E-03 | 1.13E-07 | 2 |
| H1M17357N | 2.35E+04 | 1.84E-03 | 7.81E-08 | 6.3 |
| H2aM17355N | 1.99E+04 | 2.06E-04 | 1.03E-08 | 56.2 |
| H2aM17356N | 7.26E+03 | 2.50E-04 | 3.44E-08 | 46.2 |
| H2aM17358N | 1.07E+04 | 5.67E-04 | 5.28E-08 | 20.4 |
| H2aM17359N | 1.54E+04 | 3.52E-04 | 2.29E-08 | 32.8 |

TABLE 4B-continued

Binding Kinetics at 37° C.

| mAb | ka (1/Ms) | kd (1/s) | KD (M) | t1/2 (min) |
|---|---|---|---|---|
| H2aM17360N | 2.43E+04 | 3.37E-04 | 1.39E-08 | 34.3 |
| H2aM17361N | 1.83E+04 | 4.15E-04 | 2.27E-08 | 27.8 |

NB-No detectable binding under assays conditions tested
IC-Inconclusive binding sensogram for fitting Results As shown in Tables 4A and 4B above, the antibodies bound to Ebola Virus GP with $K_D$ values ranging from 934 pM to 1890 nM at 25° C. and from 227 pM to 2310 nM at 37° C. At pH 7.4, the antibodies showed dissociative half-life (t½) values ranging from 3.0 minutes to greater than 1155 minutes at 25° C. and from 2.0 minutes to greater than 1155 minutes at 37° C. No loss in binding was observed at low pH. Several antibodies showed increased dissociative half-life (t½) values at low pH relative to pH 7.4. Antibodies with 3-fold or greater increases in dissociative half-life (t½) values at pH 5 and/or pH 6 include H1H17162P, H1H17177P, H1H17150P, H1H17151P, H1H17160P, H1H17161P, H1H17141P, H1H17139P, H1H17210P, H1H17203P, H1H17199P, H1M17348N, H1M17350N, H2aM17360N and H2aM17361N.

Example 4: Generation of Ebola Virus Pseudoparticles and Neutralization Studies

Ebola virus pseudoparticles (also called virus like particles, or VLPs) were generated by co-transfecting 293T cells with a mix of plasmid constructs expressing Ebola virus GP, HIV gag-pol, and an HIV proviral vector encoding for firefly luciferase. Supernatants containing Ebola virus pseudoparticles were harvested at 48 hours post transfection, clarified using centrifugation, aliquoted and frozen at −80° C. Control pseudoparticles were generated by substituting the plasmid expressing Ebola virus GP with a plasmid encoding for Vesicular Stomatitis virus glycoprotein (VSVg).

Ebola Pseudoparticle-Based Neutralization Assay

The pseudoparticles generated as described above were tested in neutralization assays. Specifically, dilutions of antibodies were incubated with Ebola virus pseudoparticles for 1 h at room temperature. Huh7 cells are detached using 0.02M EDTA, washed and incubated with the antibody/pseudoparticle mixtures for 72 h. Infection efficiency was quantitated by luciferase detection with the BrightGlo® luciferase assay (Promega, San Luis Obispo, Calif., USA) and read in a Victor® X3 plate reader (Perkin Elmer, Waltham, Mass., USA) for light production.

TABLE 5

Zaire 2014 VLP Neutralization

| AB ID | Corresponding Hybridoma Ab ID | Neutralizer of Zaire 2014 VLP | IC50 (M) |
|---|---|---|---|
| H1H17134P | | − | − |
| H1H17139P | | − | − |
| H1H17142P | | + | 1.59E-09 |
| H1H17151P | | + | 1.51E-09 |
| H1H17161P | | + | 2.55E-10 |
| H1H17162P | | + | 2.86E-10 |
| H1H17193P | | − | − |

TABLE 5-continued

Zaire 2014 VLP Neutralization

| AB ID | Corresponding Hybridoma Ab ID | Neutralizer of Zaire 2014 VLP | IC50 (M) |
|---|---|---|---|
| H1H17196P | | + | 1.68E-09 |
| H1H17199P | | − | − |
| H1H17203P | | + | 8.68E-10 |
| H1H17214P | | + | 8.99E-10 |
| H1H17219P | | + | 6.95E-10 |
| H1H17223P | | + | 1.58E-09 |
| H1H17228P | | + | 3.26E-09 |
| H1M17354N | H1M17354N | − | − |
| H2aM17356N | H2aM17356N | + | 4.77E-09 |
| H1M17357N | H1M17357N | − | − |
| H2aM17358N | H2aM17358N | + | 4.68E-09 |
| H2aM17359N | H2aM17359N | + | 3.36E-09 |
| H2aM17360N | H2aM17360N | + | 3.75E-09 |

The data shown above in Table 5 show that 14 out of the 20 anti-Ebola virus antibodies of the present invention, using the experimental design described herein, potently neutralize infectivity with an $IC_{50}$ ranging from about $10^{-11}$ M to about $10^{-9}$ M.

Example 5: Antibody-Dependent Cell-Mediated Cytotoxicity (ADCC) by Anti-Ebola Virus Antibodies Antibody-dependent cell-mediated cytotoxicity (ADCC) was tested by the ability of the antibodies to signal via a CD16 based reporter system (Promega ADCC reporter bioassay core kit, San Luis Obispo, Calif., USA). Ebola virus GP-expressing 293 cells were seeded. One day later, diluted antibodies produced in fuc⁻ cell lines (See U.S. Pat. No. 8,409,838) and effector cells (1.5:1 effector to target ratio) are added and incubated overnight. Reporter activity was measured with the BioGlo® luciferase assay (Promega, San Luis Obispo, Calif., USA) and read in a Victor® X3 plate reader (Perkin Elmer, Waltham, Mass., USA) for light production.

TABLE 6

ADCC Results

| | ADCC Reporter Bioassay | |
|---|---|---|
| Ab ID | Clone ID | ADCC Activity |
| H1H17134P | | + |
| H1H17139P | | + |
| H1H17142P | | + |
| H1H17151P | | + |
| H1H17161P | | − |
| H1H17162P | | − |
| H1H17193P | | + |
| H1H17196P | | + |
| H1H17199P | | + |
| H1H17203P | | + |
| H1H17214P | | + |
| H1H17219P | | − |
| H1H17223P | | + |
| H1H17228P | | + |
| H1M17354N | HCAF05C08-22 | + |
| H2aM17356N | HCAF08C07-09 | + |
| H1M17357N | HCAF09D11-13 | + |
| H2aM17358N | HCAF12C05-14 | + |
| H2aM17359N | HCAF12C06-26 | + |
| H2aM17360N | HCAF12G09-07 | + |

The ability of the antibodies to mediate ADCC was calculated on the basis of activity compared to an isotype (negative) control. Any value greater than 5 fold above the negative control was considered positive. The data above in Table 6 show that 17 out of the 20 anti-Ebola virus antibodies mediated ADCC.

Example 6: Octet Cross-Competition

Binding competition between anti-Ebola virus GP monoclonal antibodies that had been previously determined to bind to Ebola virus GP was determined using a real time, label-free bio-layer interferometry (BLI) assay on an Octet HTX biosensor (ForteBio Corp., A Division of Pall Life Sciences). The binding of relevant controls for soluble GP (sGP), GP1, or GP2, was measured in the same assay format and its response was subtracted from the Ebola virus GP reagent of interest for each mAb tested. The entire experiment was performed at 25° C. in buffer comprised of 0.01M HEPES pH7.4, 0.15M NaCl, 3 mM EDTA, 0.05% v/v Surfactant P20, 1.0 mg/mL BSA (Octet HBS-ET buffer) with the plate shaking at a speed of 1000 rpm. To assess whether two antibodies are able to compete with one another for binding to their respective epitopes on the Ebola virus GP expressed with a C-terminal polyhistidine tag (Ebola virus GP.h, Sino Biologicals Inc., also see GenBank AHX24649.1 and SEQ ID NO: 314), approximately ~1.0 nm of Ebola virus GP was first captured onto anti-penta-His antibody coated Octet biosensors (Fortebio Inc, #18-5079) by submerging the biosensors for 3 minutes into wells containing a 20 µg/mL solution of Ebola virus GP. The antigen-captured biosensors were then saturated with the first anti-Ebola virus GP monoclonal antibody (subsequently referred to as mAb-1) by immersion into wells containing a 50 µg/mL solution of mAb-1 for 5 minutes. The biosensors were then subsequently submerged into wells containing a 50 µg/mL solution of a second anti-Ebola virus GP monoclonal antibody (subsequently referred to as mAb-2) for 3 minutes. All the biosensors were washed in Octet HBS-ET buffer in between each step of the experiment. The real-time binding response was monitored during the course of the experiment and the binding response at the end of every step was recorded. The response of mAb-2 binding to Ebola virus GP pre-complexed with mAb-1 was compared and competitive/non-competitive behavior of different anti-Ebola virus GP monoclonal antibodies were determined using a 50% inhibition threshold. Table 7 explicitly defines the relationships of antibodies competing in both directions, independent of the order of binding.

As shown in Table 7, the column on the left shows the mAb1 antibodies that are captured using the AHC Octet biosensors and the column on the right demonstrates the antibodies (mAb2) that cross-compete with the mAb1 antibody.

TABLE 7

Cross-competition of anti-Ebola virus GP antibodies for binding to Ebola virus GP

| First mAb (mAb-1) Captured using AHC Octet Biosensors | mAb-2 Antibodies Shown to Compete with mAb-1 |
|---|---|
| H1H17160P | H1H17160P, H1M17354N, H1M17357N, H1H17228P, H1H17203P |
| H1M17354N | H1H17160P, H1M17354N, H1M17357N, H1H17228P, H1H17203P |
| H1M17357N | H1H17160P, H1M17354N, H1M17357N, H1H17228P, H1H17203P |
| H1H17228P | H1H17160P, H1M17354N, H1M17357N, H1H17228P, H1H17203P, H1H17151P, H1H17142P, H1H17177P, H2aM17359N |
| H1H17203P | H1H17160P, H1M17354N, H1M17357N, H1H17228P, H1H17203P, H1H17151P, H1H17142P, H1H17177P, H2aM17359N, H1H17214P, H1H17199P, H2aM17358N, H2aM17360N, H1M17352N |
| H1H17151P | H1H17228P, H1H17203P, H1H17151P, H1H17142P, H1H17177P, H2aM17359N, H1H17214P, H1H17199P, H2aM17358N, H2aM17360N, H1M17352N, H2aM17356N, H2aM17361N, H2aM17355N, H1H17211P, H1M17353N, H1H17223P, H1H17196P, H1H17193P |
| H1H17142P | H1H17228P, H1H17203P, H1H17151P, H1H17142P, H1H17177P, H2aM17359N, H1H17214P, H1H17199P, H2aM17358N, H2aM17360N, H1M17352N, H2aM17356N, H2aM17361N, H2aM17355N, H1M17353N, H1H17223P, H1H17196P, H1H17193P |
| H1H17177P | H1H17228P, H1H17203P, H1H17151P, H1H17142P, H1H17177P, H2aM17359N, H1H17214P, H1H17199P, H2aM17358N, H2aM17360N, H1M17352N, H2aM17356N, H2aM17361N, H2aM17355N, H1H17211P, H1M17348N, H1M17353N, H1H17141P, H1H17223P, H1H17196P, H1H17139P, H1H17193P, H1M17350N |
| H2aM17359N | H1H17228P, H1H17203P, H1H17151P, H1H17142P, H1H17177P, H2aM17359N, H1H17214P, H1H17199P, H2aM17358N, H2aM17360N, H1M17352N H2aM17356N, H2aM17361N, H2aM17355N, 1H17211P, H1M17348N, H1M17353N, H1H17141P, H1H17223P H1H17139P, H1H17193P, H1M17350N |
| H1H17214P | H1H17203P, H1H17151P, H1H17142P, H1H17177P, H2aM17359N, H1H17214P H1H17199P, H2aM17358N, H2aM17360N, H1M17352N, H2aM17356N H2aM17361N, H2aM17355N, H1H17211P, H1M17348N, H1M17353N H1H17141P, H1H17223P, H1H17139P H1H17193P, H1M17350N |
| H1H17199P | H1H17203P, H1H17151P, H1H17142P, H1H17177P, H2aM17359N, H1H17214P H1H17199P, H2aM17358N, H2aM17360N, H1M17352N, H2aM17356N, H2aM17361N, H2aM17355N, H1H17211P, H1M17348N, H1M17353N, H1H17141P, H1H17139P, H1H17193P, H1M17350N |
| H2aM17358N | H1H17203P, H1H17151P, H1H17142P, H1H17177P, H2aM17359N, H1H17214P, H1H17199P, H2aM17358N, H2aM17360N, H1M17352N, H2aM17356N H2aM17361N, H2aM17355N, H1H17211P, H1M17348N, H1M17353N H1H17139P, H1H17193P, H1M17350N |
| H2aM17360N | H1H17203P, H1H17151P, H1H17142P, H1H17177P, H2aM17359N H1H17214P, H1H17199P, H2aM17358N, H2aM17360N, H1M17352N H2aM17356N, H2aM17361N, H2aM17355N, H1H17211P, H1M17348N H1M17353N, H1H17139P, H1H17193P, H1M17350N |
| H1M17352N | H1H17203P, H1H17151P, H1H17142P, H1H17177P, H2aM17359N, H1H17214P, H1H17199P, H2aM17358N, H2aM17360N, H1M17352N, H2aM17356N, H2aM17361N, H2aM17355N, H1H17211P, H1M17348N, H1M17353N, H1H17139P, H1H17193P, H1M17350N |
| H2aM17356N | H1H17151P, H1H17142P, H1H17177P, H2aM17359N, H1H17214P H1H17199P, H2aM17358N, H2aM17360N, H1M17352N, H2aM17356N H2aM17361N, H2aM17355N, H1H17211P, H1M17348N H1M17353N, H1H17139P, H1H17193P, H1M17350N |
| H2aM17361N | H1H17151P, H1H17142P, H1H17177P, H2aM17359N, H1H17214P, H1H17199P, H2aM17358N, H2aM17360N, H1M17352N, H2aM17356N, H2aM17361N, H2aM17355N, H1H17211P, H1M17348N, H1M17353N, H1H17139P, H1H17193P, H1M17350N |
| H2aM17355N | H1H17203P, H1H17151P, H1H17142P, H1H17177P, H2aM17359N H1H17214P, H1H17199P, H2aM17358N, H2aM17360N, H1M17352N H2aM17356N, H2aM17361N, H2aM17355N, H1H17211P, H1M17348N H1M17353N, H1H17193P, H1M17350N |
| H1H17211P | H1H17151P, H1H17177P, H2aM17359N, H1H17214P, H1H17199P H2aM17358N, H2aM17360N, H1M17352N, H2aM17356N, H2aM17361N, H2aM17355N, H1H17211P, H1M17348N, H1M17353N H1H17193P, H1M17350N |
| H1M17348N | H1H17177P, H2aM17359N, H1H17214P, H1H17199P, H2aM17358N H2aM17360N, H1M17352N, H2aM17356N, H2aM17361N H2aM17355N, H1H17211P, H1M17348N, H1M17353N, H1H17193P H1M17350N |
| H1M17353N | H1H17151P, H1H17142P, H1H17177P, H2aM17359N, H1H17214P H1H17199P, H2aM17358N, H2aM17360N, H1M17352N H2aM17356N, H2aM17361N, H2aM17355N, H1H17211P, H1M17348N, H1M17353N, H1H17141P, H1H17223P, H1H17196P, H1H17139P, H1H17193P |

TABLE 7-continued

Cross-competition of anti-Ebola virus GP antibodies for binding to Ebola virus GP

| First mAb (mAb-1) Captured using AHC Octet Biosensors | mAb-2 Antibodies Shown to Compete with mAb-1 |
|---|---|
| H1H17141P | H1H17177P, H2aM17359N, H1H17214P, H1H17199P, H1M17353N H1H17141P, H1H17223P, H1H17196P, H1H17139P |
| H1H17223P | H1H17151P, H1H17142P, H1H17177P, H2aM17359N, H1H17214P, H1M17353N H1H17141P, H1H17223P, H1H17196P, H1H17139P |
| H1H17196P | H1H17151P, H1H17142P, H1H17177P, H1M17353N, H1H17141P, H1H17223P, H1H17196P, H1H17139P |
| H1H17139P | H1H17177P, H2aM17359N, H1H17214P, H1H17199P, H2aM17358N H2aM17360N, H1M17352N, H2aM17356N, H2aM17361N, H1M17353N H1H17141P, H1H17223P, H1H17196P, H1H17139P |
| H1H17193P | H1H17151P, H1H17142P, H1H17177P, H2aM17359N, H1H17214P, H1H17199P H2aM17358N, H2aM17360N, H1M17352N, H2aM17356N, H2aM17361N H2aM17355N, H1H17211P, H1M17348N, H1M17353N, H1H17193P, H1M17350N |
| H1M17350N | H1H17177P, H2aM17359N, H1H17214P, H1H17199P, H2aM17358N, H2aM17360N, H1M17352N, H2aM17356N, H2aM17361N, H2aM17355N H1H17211P, H1M17348N, H1H17193P, H1M17350N |
| H1H17219P | H1H17219P, H1H17150P, H1H17161P |
| H1H17150P | H1H17219P, H1H17150P, H1H17161P |
| H1H17161P | H1H17219P, H1H17150P, H1H17161P |
| H1M17349N | H1M17349N |
| H1H17134P | H1H17134P |
| H1H17162P | H1H17162P |
| H1H17210P | H1H17210P |

Example 7: Sequential Binding of H1H17203P, H1H17139P and H1H17161P to Ebola Virus Glycoprotein Taking the information obtained from the cross-competition experiments, a sequential binding study was done to determine if three individual candidate antibodies are capable of binding simultaneously to soluble Ebola virus glycoprotein (GP), thereby confirming that the binding sites on Ebola virus GP are independent for each monoclonal antibody. If so, this information would support the use of these antibodies in a therapeutic cocktail.

Accordingly, sequential binding experiments, for three anti-Ebola virus GP monoclonal antibodies to Ebola virus GP, H1H17203P, H1H17139P and H1H17161P were tested for binding independently and non-competitively to Ebola virus GP. This experiment was done using a real time, label-free bio-layer interferometry (BLI) assay on an Octet RED biosensor (ForteBio Corp., A Division of Pall Life Sciences). The entire experiment was performed at 25° C. in buffer comprised of 0.01M HEPES pH7.4, 0.15M NaCl, 3 mM EDTA, 0.05% v/v Surfactant P20, 1.0 mg/mL BSA (Octet HBS-ET buffer) with the plate shaking at a speed of 1000 rpm. To assess whether three antibodies are able to bind simultaneously to captured antigen Ebola virus GP expressed with a C-terminal polyhistidine tag (Ebola virus GP.his, Sino Biologicals), approximately ~0.6 nm of Ebola virus GP.h was first captured onto anti-penta-His antibody coated Octet biosensors (Fortebio Inc, #18-5079) by submerging the biosensors for 3 minutes into wells containing a 20 µg/mL solution of Ebola virus GP.h. The antigen-captured biosensors were then saturated with the first anti-Ebola virus GP monoclonal antibody (subsequently referred to as H1H17161P) by immersion into wells containing a 50 µg/mL solution of REGN H1H17161P for 5 minutes. The biosensors were then subsequently submerged into wells containing a 50 µg/mL solution of a second anti-Ebola virus GP monoclonal antibody (subsequently referred to as H1H17139P) for 5 minutes. Finally, 50 µg/mL of the third antibody (subsequently referred to as H1H17161P) was injected for 5 minutes to reach saturation. The real-time binding response was monitored during the course of the experiment and the binding response at the end of every step was recorded.

Results

The three candidate monoclonal antibodies tested were capable of binding simultaneously to Ebolavirus GP, indicating that each antibody did not interfere with the binding site on Ebolavirus GP of the other antibodies tested, suggesting that they each bound or interacted with different epitopes. This supports a role for use of these three antibodies in a therapeutic antibody cocktail.

Example 8: Binding of Anti-Ebola Antibodies to Different Ebola Virus Like Particle (VLP) Strains A study was done to determine whether the anti-Ebola virus GP antibodies would react with virus like particles (VLPs) containing GPs from other Ebola virus strains. Included in this study were VLPs containing GPs from Bundibugyo NC_014373, Cote d'Ivoire FJ217162, Sudan NC_006432, Zaire.1995, Zaire.2014 AY354458 and a negative control, VSV glycoprotein (VSVg). The study was done using "MesoScale Discovery" (MSD), a technology that allows binding/fixation of the Ebola strain VLPs (that express the Ebola glycoproteins/viral surface proteins) to a carbon surface followed by an ELISA-type binding assay. The purpose was to identify the binding profiles of the mAbs with respect to various Ebola strains.

The assay was performed in 96 well polypropylene microwell plates by first preparing a 1:10 dilution of the supernatants from the various VLPs/well (as noted in the following table) and adding the dilutions to PBS (50 µl/well) and incubating at 4° C. overnight.

The liquid in the wells was discarded followed by blocking with 150 µl/well in PBS+2% BSA and incubating for one hour at room temperature. The contents of each well were then discarded and the wells were washed with PBS using an AquaMax2000 plate washer designated for MSD. Fifty microliters of primary antibody was diluted in PBS+1% BSA and incubated at room temperature with shaking at an intermediate speed (5). The well contents were then discarded and the plates were washed with PBS. Fifty microliters of sulfo-TAG detection reagent (human or mouse Fc) at a concentration of 1 µg/ml in PBS+0.5% BSA was added to each well and incubated at room temperature for one hour with shaking at an intermediate speed (5). The well contents were discarded and the plates were washed with PBS+0.5% BSA. To each well was added 150 µl of 1× Read Buffer without surfactant and the plates were read on a SECTORImager6000 from barcode.

The results, which are shown in Table 8 below, demonstrate that all of the anti-Ebola virus GP antibodies tested bind to VLPs containing the Zaire 2014 and Zaire 1995 GPs. Certain of the antibodies tested bind to VLPs containing the GPs from other Ebola virus strains, in addition to binding the two Zaire strains noted in Table 8. In particular, in addition to binding to the VLPs containing the GPs from Zaire 2014 and Zaire 1995, the anti-Ebola virus antibodies designated as H1H17161P and H1H17162P bind to VLPs containing the GPs from Sudan and Bundibugyo strains, while the anti-Ebola virus antibodies designated as H2aM17356N and H1H17142P bind to Bundibugyo and Cote d'Ivoire strains.

TABLE 8

Cross Reactivity of anti-Ebola Virus Antibodies with GPs from Various Strains of Ebola Virus Anti-Ebola Virus Antibody Binding to VLPs containing GPs from Various Ebola Virus Strains

| AbPID | Sudan | Bundibugyo | Cote d'Ivoire | Zaire 2014 | Zaire 1995 |
|---|---|---|---|---|---|
| H1H17161P | + | + | − | + | + |
| H1H17139P | − | − | − | + | + |
| H1H17203P | − | − | − | + | + |
| H1H17219P | − | − | − | + | + |
| H1H17162P | + | + | − | + | + |
| H1H17199P | − | − | − | + | + |
| H1H17193P | − | − | − | + | + |
| H1M17354N | − | − | − | + | + |
| H1M17357N | − | − | − | + | + |
| H1H17134P | − | − | − | + | + |
| H1H17360N | − | − | − | + | + |
| H1H17358N2 | − | − | − | + | + |
| H2aM17356N | − | + | + | + | + |
| H1H17223P | − | − | − | + | + |
| H1H17196P | − | − | − | + | + |
| H1H17151P | − | − | − | + | + |
| H1H17142P | − | + | + | + | + |
| H1H17214P | − | − | − | + | + |
| H1H17228P | − | − | − | + | + |
| H2aM17359N | − | − | − | + | + |

Example 9: In Vitro Neutralization of Live/Infectious Ebola Virus (EBOV)

Antibodies designated as H1H17203P, H1H17139P and H1H17161P were analyzed for their ability to neutralize infectious EBOV in Vero cells. Vero cells were plated on 384-well plates in DMEM-10% FBS and allowed to grow to approximately 75% confluence at 37° C. H1H17203P, H1H17139P and H1H17161P were diluted as indicated. EBOV strains (Mayinga, Kikwit, Makona, and guinea pig-adapted Mayinga) were thawed and diluted appropriately to an MOI between 0.01-0.1. A commercially available anti-EBOV antibody designated KZ52 was used as a positive control. (See Maruyama, T. et al., J Virol 73, 6024-6030 (1999). Antibodies were incubated with the virus for 1 hour at 37° C. The antibody/virus mix was then added to the pre-plated cells and plates were incubated at 37° C. for 24 hours. After the incubation period, plates were removed from the incubator and inactivated by immersing in 10% neutral buffered formalin, placed in a heat sealed bag and stored at 4° C. overnight in BSL-4. Plates were washed 3 times in 1×-PBS and cells were permeabilized at room temperature (RT) with 25 µl of 0.1% Triton X-100 in 1×-PBS for 15-20 minutes. Triton-X was discarded and the plates were blocked with 3.5% BSA in 1×-PBS for 1 hour at RT. Plates were treated overnight at 4° C. with anti-EBOV GP primary antibody 4F3 (See IBT BIOSERVICES for mouse anti-EBOV GP monoclonal antibody 4F3, catalogue number 0201-020) diluted 1:1500 in 1×-PBS. Plates were washed in 1×-PBS for 10-15 minutes and repeated twice. Cells were incubated for 1 hour with Alexa-fluor-488 conjugated anti-mouse secondary antibody. Secondary antibody was discarded and plates were washed in 1×-PBS for 10-15 minutes and repeated twice. Plates were incubated with 25 µl/well of Hoechst (1:50,000 in 1×-PBS) for 30 minutes at RT. Plates were imaged by fluorescence microscopy using blue and green fluorescence channels.

Results

The results, shown in FIG. 1, demonstrated that the H1H17161P antibody neutralized live virus and was more potent than the positive control antibody KZ52, but the antibodies designated as H1H17203P and H1H17139P did not act as neutralizers.

Example 10: Binding of Anti-Ebola Antibodies to Soluble GP (sGP)

The fourth gene in the EBOV genome encodes two unique proteins, a non-structural, dimeric secreted glycoprotein, termed sGP, and a trimeric, virion-attached, envelope glycoprotein (GP). These two GPs share the first 295 amino acids, but have unique C termini. To determine if the Regeneron lead mAbs bind to sGP, a recombinant sGP.mmh protein was produced in-house (SEQ ID NO: 317). Interferometry based biosensor Octet HTX was used to determine if H1H17203P, H1H17139P, H1H17161P monoclonal antibodies can bind to the Ebola sGP.mmh protein. The format of the assay involved capturing H1H17203P, H1H17139P, H1H17161P, onto anti-hFc sensor tips, followed by submersion into 300 nM solutions of Ebola GP.10×his (SEQ ID NO: 318), sGP.mmh (SEQ ID NO: 317), or hCNTFR (ciliary neurotrophic factor receptor.mmh, which is a negative control protein). Each mAb was captured at a level between 0.94-1.36 nm.

Figure 2:
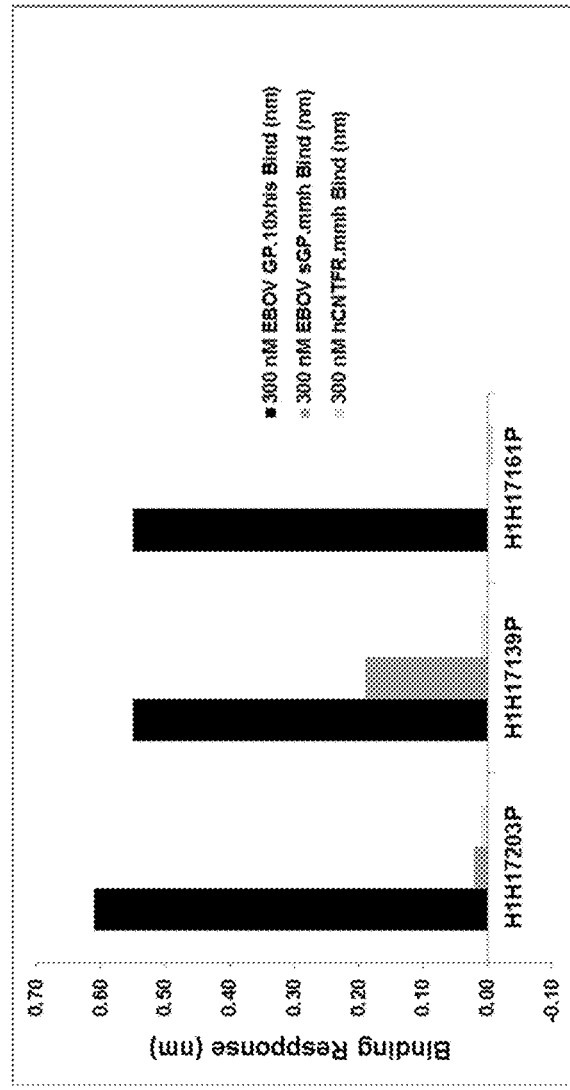
FIG. 2: Shows the interaction of three Anti-EBOV Antibodies with Ebola GP or Ebola soluble GP (sGP).

As shown in FIG. 2, all mAbs showed specific binding to Ebola GP.10×his and no binding to the negative control protein; whereas, only H1H17139 demonstrated specific binding to Ebola sGP.mmh. This finding suggests that the binding epitope of H1H17139 is likely located in a common region within the first 295 amino acids of both the sGP and GP; whereas the other mAbs possibly only recognize the C-terminus of Ebola GP.

Example 11: Binding of Additional Anti-EBOV GP Antibodies to Ebola GP.h, Ebola GP Soluble.mmh and hCNTFR.mmh A further study was done to determine the binding characteristics of additional anti-EBOV GP antibodies of the invention; in particular, the study was done to determine the ability of these additional antibodies to bind to soluble GP and GP. This study was done using a real time, label-free bio-layer interferometry (BLI) assay on an Octet HTX biosensor (ForteBio Corp., A Division of Pall Life Sciences). The entire experiment was performed at 25° C. in buffer comprised of 0.01M HEPES pH7.4, 0.15M NaCl, 3 mM EDTA, 0.05% v/v Surfactant P20, 1.0 mg/mL BSA (Octet HBS-ET buffer) with the plate shaking at a speed of 1000 rpm. To assess if antibodies were able to bind Ebola sGP or other Ebola GP reagents, approximately ~1.0 nm of anti-Ebola GP mAbs were captured onto anti-human Fc (Fortebio Inc, #18-5064) antibody coated Octet biosensors by submerging the biosensors for 3 minutes into wells containing 20 µg/mL solutions of mAbs. The mAb-captured biosensors were tested for binding to selected protein reagents by immersion into wells containing 300 nM solutions of Ebola GP proteins or irrelevant controls for 5 minutes. All the biosensors were washed in Octet HBS-ET buffer in between each step of the experiment. The real-time binding response was monitored during the course of the experiment and the binding response at the end of every step was recorded.

Results

As shown in Table 9, any value below 0.10 nm was determined to be a non-binding antibody. Based on the results to date, all but one of the antibodies (H1H17360N) tested showed binding to EBOV full length GP, and thirteen out of the twenty antibodies tested showed binding to soluble GP (sGP).

TABLE 9

Binding of anti-Ebola GP antibodies to Ebola GP.h., Ebola GP soluble.mmh, and hCNTFR.mmh

| Antibody Number | Binding to sGP | 300 nM Ebola sGP (F2) Bind (nm) | 300 nM Ebola GP.h Bind (nm) | 300 nM hCNTFR.mmh (Negative control) Bind (nm) |
|---|---|---|---|---|
| H1H17161P | No | 0.00 | 0.55 | −0.01 |
| H1H17139P | Yes | 0.19 | 0.55 | 0.01 |
| H1H17203P | No | 0.02 | 0.61 | 0.01 |
| H1H17219P | No | 0.01 | 0.68 | 0.01 |
| H1H17162P | No | 0.03 | 0.49 | 0.02 |
| H1H17199P | Yes | 0.33 | 0.38 | 0.00 |
| H1H17193P | Yes | 0.26 | 0.33 | 0.02 |
| H1M17354N | Yes | 0.18 | 0.71 | 0.02 |
| H1M17357N | No | 0.10 | 0.56 | 0.01 |
| H1H17134P | No | 0.01 | 0.70 | −0.01 |
| H1H17360N | No | 0.09 | 0.09 | 0.03 |
| H1H17358N2 | Yes | 0.30 | 0.35 | 0.01 |
| H1H17356N | Yes | 0.22 | 0.23 | 0.02 |
| H1H17223P | Yes | 0.31 | 0.61 | 0.02 |
| H1H17196P | Yes | 0.25 | 0.62 | 0.01 |
| H1H17151P | Yes | 0.33 | 0.43 | −0.02 |
| H1H17142P | Yes | 0.28 | 0.34 | 0.01 |
| H1H17214P | Yes | 0.38 | 0.52 | 0.01 |
| H1H17228P | Yes | 0.35 | 0.58 | 0.00 |
| H1H17359N | Yes | 0.39 | 0.51 | 0.00 |

What is claimed is:

1. An isolated recombinant antibody or antigen-binding fragment thereof that specifically binds to Ebola virus (EBOV) and/or an Ebola virus glycoprotein (EBOV-GP), comprising:
   (a) a heavy chain complementarity determining region 1 (HCDR1) amino acid sequence as set forth in SEQ ID NO: 20 with no more than one amino acid substitution; an HCDR2 amino acid sequence as set forth in SEQ ID NO: 22 with no more than one amino acid substitution; an HCDR3 amino acid sequence as set forth in SEQ ID NO: 24 with no more than one amino acid substitution; a light chain complementarity determining region LCDR1 amino acid sequence as set forth in SEQ ID NO: 28 with no more than one amino acid substitution; an LCDR2 amino acid sequence as set forth in SEQ ID NO: 30 with no more than one amino acid substitution; and an LCDR3 amino acid sequence as set forth in SEQ ID NO: 32 with no more than one amino acid substitution;
   (b) an HCDR1 amino acid sequence of SEQ ID NO: 68 with no more than one amino acid substitution; an HCDR2 amino acid sequence of SEQ ID NO: 70 with no more than one amino acid substitution; an HCDR3 amino acid sequence of SEQ ID NO: 72 with no more than one amino acid substitution; an LCDR1 amino acid sequence of SEQ ID NO: 76 with no more than one amino acid substitution; an LCDR2 amino acid sequence of SEQ ID NO: 78 with no more than one amino acid substitution; and an LCDR3 amino acid sequence of SEQ ID NO: 80 with no more than one amino acid substitution; or
   (c) an HCDR1 amino acid sequence of SEQ ID NO: 148 with no more than one amino acid substitution; an HCDR2 amino acid sequence of SEQ ID NO: 150 with no more than one amino acid substitution; an HCDR3 amino acid sequence of SEQ ID NO: 152 with no more than one amino acid substitution; an LCDR1 amino acid sequence of SEQ ID NO: 156 with no more than one amino acid substitution; an LCDR2 amino acid sequence of SEQ ID NO: 158 with no more than one amino acid substitution; and an LCDR3 amino acid sequence of SEQ ID NO: 160 with no more than one amino acid substitution.

2. The isolated recombinant antibody or antigen-binding fragment thereof of claim 1, comprising:
   (a) a heavy chain variable region (HCVR) amino acid sequence having 95% sequence identity to SEQ ID NO: 18; and a light chain variable region (LCVR) amino acid sequence having 95% sequence identity to SEQ ID NO: 26;
   (b) an HCVR amino acid sequence having 95% sequence identity to SEQ ID NO: 66; and an LCVR amino acid sequence having 95% sequence identity to SEQ ID NO: 74; or
   (c) an HCVR amino acid sequence having 95% sequence identity to SEQ ID NO: 146; and an LCVR amino acid sequence having 95% sequence identity to SEQ ID NO: 154.

3. The isolated recombinant antibody or antigen-binding fragment thereof of claim 1, comprising:
   (a) an HCVR amino acid sequence having 98% sequence identity to SEQ ID NO: 18; and an LCVR amino acid sequence having 98% sequence identity to SEQ ID NO: 26;
   (b) an HCVR amino acid sequence having 98% sequence identity to SEQ ID NO: 66; and an LCVR amino acid sequence having 98% sequence identity to SEQ ID NO: 74; or
   (c) an HCVR amino acid sequence having 98% sequence identity to SEQ ID NO: 146; and an LCVR amino acid sequence having 98% sequence identity to SEQ ID NO: 154.

4. The isolated recombinant antibody or antigen-binding fragment thereof of claim 1, comprising:
   (a) an HCVR amino acid sequence having 99% sequence identity to SEQ ID NO: 18; and an LCVR amino acid sequence having 99% sequence identity to SEQ ID NO: 26;

(b) an HCVR amino acid sequence having 99% sequence identity to SEQ ID NO: 66; and an LCVR amino acid sequence having 99% sequence identity to SEQ ID NO: 74; or (c) an HCVR amino acid sequence having 99% sequence identity to SEQ ID NO: 146; and an LCVR amino acid sequence having 99% sequence identity to SEQ ID NO: 154.

5. The isolated recombinant antibody or antigen-binding fragment thereof of claim 1, comprising:
an HCVR having an amino acid sequence of SEQ ID NO: 18 with no more than 3 amino acid substitutions; and an LCVR amino acid sequence of SEQ ID NO: 26 with no more than 3 amino acid substitutions.

6. The isolated recombinant antibody or antigen-binding fragment thereof of claim 1, comprising:
an HCVR having an amino acid sequence of SEQ ID NO: 66 with no more than 3 amino acid substitutions; and an LCVR amino acid sequence of SEQ ID NO: 74 with no more than 3 amino acid substitutions.

7. The isolated recombinant antibody or antigen-binding fragment thereof of claim 1, comprising:
an HCVR having an amino acid sequence of SEQ ID NO: 146 with no more than 3 amino acid substitutions; and an LCVR amino acid sequence of SEQ ID NO: 154 with no more than 3 amino acid substitutions.

8. The isolated recombinant antibody or antigen-binding fragment thereof of claim 1, comprising:
an HCVR having an amino acid sequence of SEQ ID NO: 18 with no more than 2 amino acid substitutions; and an LCVR amino acid sequence of SEQ ID NO: 26 with no more than 2 amino acid substitutions.

9. The isolated recombinant antibody or antigen-binding fragment thereof of claim 1, comprising:
an HCVR having an amino acid sequence of SEQ ID NO: 66 with no more than 2 amino acid substitutions; and an LCVR amino acid sequence of SEQ ID NO: 74 with no more than 2 amino acid substitutions.

10. The isolated recombinant antibody or antigen-binding fragment thereof of claim 1, comprising:
an HCVR having an amino acid sequence of SEQ ID NO: 146 with no more than 2 amino acid substitutions; and an LCVR amino acid sequence of SEQ ID NO: 154 with no more than 2 amino acid substitutions.

11. The isolated antibody of claim 1, wherein the antibody inhibits entry of Ebola virus into a host cell.

12. A pharmaceutical composition comprising one or more isolated monoclonal antibodies or antigen-binding fragments thereof that bind specifically to EBOV according to claim 1, and a pharmaceutically acceptable carrier or diluent.

13. The pharmaceutical composition of claim 12, wherein the isolated monoclonal antibody or an antigen-binding fragment thereof comprises an HCDR1 amino acid sequence of SEQ ID NO: 20 with no more than one amino acid substitution; an HCDR2 amino acid sequence of SEQ ID NO: 22 with no more than one amino acid substitution; an HCDR3 amino acid sequence of SEQ ID NO: 24 with no more than one amino acid substitution; an LCDR1 amino acid sequence of SEQ ID NO: 28 with no more than one amino acid substitution; an LCDR2 amino acid sequence of SEQ ID NO: 30 with no more than one amino acid substitution; and an LCDR3 amino acid sequence of SEQ ID NO: 32 with no more than one amino acid substitution, and a pharmaceutically acceptable carrier or diluent.

14. The pharmaceutical composition of claim 12, wherein the isolated monoclonal antibody or an antigen-binding fragment thereof comprises an HCDR1 amino acid sequence of SEQ ID NO: 68 with no more than one amino acid substitution; an HCDR2 amino acid sequence of SEQ ID NO: 70 with no more than one amino acid substitution; an HCDR3 amino acid sequence of SEQ ID NO: 72 with no more than one amino acid substitution; an LCDR1 amino acid sequence of SEQ ID NO: 76 with no more than one amino acid substitution; an LCDR2 amino acid sequence of SEQ ID NO: 78 with no more than one amino acid substitution; and an LCDR3 amino acid sequence of SEQ ID NO: 80 with no more than one amino acid substitution.

15. The pharmaceutical composition of claim 12, wherein the isolated monoclonal antibody or an antigen-binding fragment thereof comprises an HCDR1 amino acid sequence of SEQ ID NO: 148 with no more than one amino acid substitution; an HCDR2 amino acid sequence of SEQ ID NO: 150 with no more than one amino acid substitution; an HCDR3 amino acid sequence of SEQ ID NO: 152 with no more than one amino acid substitution; an LCDR1 amino acid sequence of SEQ ID NO: 156 with no more than one amino acid substitution; an LCDR2 amino acid sequence of SEQ ID NO: 158 with no more than one amino acid substitution; and an LCDR3 amino acid sequence of SEQ ID NO: 160 with no more than one amino acid substitution.

16. An isolated polynucleotide molecule comprising a polynucleotide sequence that encodes an HCVR, and/or an LCVR of an antibody as set forth in claim 1.

17. A vector comprising the polynucleotide sequence of claim 16.

18. An isolated cell expressing the vector of claim 17.

* * * * *

UNITED STATES PATENT AND TRADEMARK OFFICE
CERTIFICATE OF CORRECTION

PATENT NO. : 11,530,255 B2
APPLICATION NO. : 17/039557
DATED : December 20, 2022
INVENTOR(S) : Christos Kyratsous et al.

Page 1 of 4

It is certified that error appears in the above-identified patent and that said Letters Patent is hereby corrected as shown below:

In the Claims

Column 203, Line 34, Claim 1:
"1(HCDR1)"

Should read:
--(HCDR)1--

Column 203, Lines 41, Claim 1:
"LCDR1"

Should read:
--(LCDR)1--

Column 204, Line 35, Claim 2:
"having 95%"

Should read:
--having at least 95%--

Column 204, Line 37, Claim 2:
"having 95%"

Should read:
--having at least 95%--

Column 204, Line 39, Claim 2:
"having 95%"

Signed and Sealed this
Thirteenth Day of May, 2025

Coke Morgan Stewart
*Acting Director of the United States Patent and Trademark Office*

Should read:
--having at least 95%--

Column 204, Line 41, Claim 2:
"having 95%"

Should read:
--having at least 95%--

Column 204, Line 43, Claim 2:
"having 95%"

Should read:
--having at least 95%--

Column 204, Line 45, Claim 2:
"having 95%"

Should read:
--having at least 95%--

Column 204, Line 50, Claim 3:
"having 98%"

Should read:
--having at least 98%--

Column 204, Line 52, Claim 3:
"having 98%"

Should read:
--having at least 98%--

Column 204, Line 54, Claim 3:
"having 98%"

Should read:
--having at least 98%--

Column 204, Line 56, Claim 3:
"having 98%"

Should read:
--having at least 98%--

Column 204, Line 58, Claim 3:
"having 98%"

Should read:
--having at least 98%--

Column 204, Line 60, Claim 3:
"having 98%"

Should read:
--having at least 98%--

Column 204, Line 64, Claim 4:
"having 99%"

Should read:
--having at least 99%--

Column 204, Line 66, Claim 4:
"having 99%"

Should read:
--having at least 99%--

Column 205, Line 1, Claim 4:
"having 99%"

Should read:
--having at least 99%--

Column 205, Line 3, Claim 4:
"having 99%"

Should read:
--having at least 99%--

Column 205, Line 5, Claim 4:
"having 99%"

Should read:
--having at least 99%--

Column 205, Line 7, Claim 4:
"having 99%"

Should read:
--having at least 99%--

Column 205, Line 49, Claim 12:
"monoclonal"

Should read:
--recombinant--

Column 206, Line 5, Claim 13:
"monoclonal"

Should read:
--recombinant--

Column 206, Lines 15-16, Claim 13:
"substitution, and a pharmaceutically acceptable carrier or diluent."

Should read:
--substitution.--

Column 206, Line 18, Claim 14:
"monoclonal"

Should read:
--recombinant--

Column 206, Line 31, Claim 15:
"monoclonal"

Should read:
--recombinant--

Column 206, Line 45, Claim 16:
"An isolated"

Should read:
--The isolated--